US010857237B2

(12) United States Patent
Malik et al.

(10) Patent No.: US 10,857,237 B2
(45) Date of Patent: Dec. 8, 2020

(54) ANTI-NUCLEOLIN AGENT-CONJUGATED NANOPARTICLES AS RADIO-SENSITIZERS AND MRI AND/OR X-RAY CONTRAST AGENTS

(71) Applicant: University of Louisville Research Foundation, Inc., Louisville, KY (US)

(72) Inventors: Mohammad Tariq Malik, Prospect, KY (US); Martin G. O'Toole, Louisville, KY (US); Paula J. Bates, Louisville, KY (US)

(73) Assignee: University of Louisville Research Foundation, Inc., Louisville, KY (US)

(*) Notice: Subject to any disclaimer, the term of this patent is extended or adjusted under 35 U.S.C. 154(b) by 0 days.

(21) Appl. No.: 15/571,763

(22) PCT Filed: May 5, 2016

(86) PCT No.: PCT/US2016/030985
§ 371 (c)(1),
(2) Date: Nov. 3, 2017

(87) PCT Pub. No.: WO2016/179394
PCT Pub. Date: Nov. 10, 2016

(65) Prior Publication Data
US 2018/0200385 A1 Jul. 19, 2018

Related U.S. Application Data

(60) Provisional application No. 62/235,496, filed on Sep. 30, 2015, provisional application No. 62/157,243, filed on May 5, 2015.

(51) Int. Cl.
| | |
|---|---|
| *A61K 49/00* | (2006.01) |
| *A61K 47/69* | (2017.01) |
| *A61K 41/00* | (2020.01) |
| *A61K 49/04* | (2006.01) |
| *A61K 31/28* | (2006.01) |
| *A61K 45/06* | (2006.01) |
| *A61K 31/7105* | (2006.01) |
| *A61K 49/18* | (2006.01) |
| *A61K 9/00* | (2006.01) |
| *A61K 47/54* | (2017.01) |
| *A61P 35/00* | (2006.01) |
| *C07K 16/18* | (2006.01) |
| *C07K 16/30* | (2006.01) |
| *C12N 15/115* | (2010.01) |

(52) U.S. Cl.
CPC ........ *A61K 47/6923* (2017.08); *A61K 9/0019* (2013.01); *A61K 31/28* (2013.01); *A61K 31/7105* (2013.01); *A61K 41/0038* (2013.01); *A61K 45/06* (2013.01); *A61K 47/549* (2017.08); *A61K 47/6929* (2017.08); *A61K 49/0032* (2013.01); *A61K 49/0065* (2013.01); *A61K 49/0428* (2013.01); *A61K 49/1875* (2013.01); *A61K 49/1881* (2013.01); *A61P 35/00* (2018.01); *C07K 16/18* (2013.01); *C07K 16/30* (2013.01); *C12N 15/115* (2013.01)

(58) Field of Classification Search
CPC ....... A61P 35/00; C12N 15/115; C07K 16/30; C07K 16/18; A61K 47/00; A61K 47/6923; A61K 49/00; A61K 49/1875; A61K 47/6929; A61K 47/549; A61K 9/00; A61K 9/0019; A61K 49/0032; A61K 45/00; A61K 45/06; A61K 41/00; A61K 41/0038; A61K 31/00; A61K 31/7105; A61K 31/28; A61K 49/1881; A61K 49/0428; A61K 49/0065; A61K 2300/00
USPC ........ 424/1.11, 1.65, 1.69, 9.1, 9.2, 9.3, 9.4, 424/9.5, 9.6, 9.32; 977/773
See application file for complete search history.

(56) References Cited

U.S. PATENT DOCUMENTS

| | | |
|---|---|---|
| 4,474,892 A | 10/1984 | Murad et al. |
| 4,522,811 A | 6/1985 | Eppstein et al. |
| 4,665,897 A | 5/1987 | Lemelson |
| 5,055,459 A | 10/1991 | Andersson et al. |
| 5,093,246 A | 3/1992 | Cech et al. |
| 5,192,660 A | 3/1993 | Reed-Gitomer |
| 5,530,101 A | 6/1996 | Queen et al. |
| 5,545,807 A | 8/1996 | Surani et al. |
| 5,567,595 A | 10/1996 | Kok |

(Continued)

FOREIGN PATENT DOCUMENTS

| | | |
|---|---|---|
| AU | 762572 | 11/1999 |
| CA | 2 549 467 | 12/2012 |

(Continued)

OTHER PUBLICATIONS

Ma et al, Zhonghua Fangshe Yixue Yu Fanghu Zazhi, Nov. 2015, vol. 35, No. 11, pp. 809-814 (Year: 2015).*

(Continued)

*Primary Examiner* — D. L. Jones
(74) *Attorney, Agent, or Firm* — Evan Law Group LLC

(57) ABSTRACT

A composition comprises an anti-nucleolin agent conjugated to nanoparticles, and optionally containing gadolinium. Furthermore, a pharmaceutical composition for treating cancer comprises a composition including an anti-nucleolin agent conjugated to nanoparticles, and a pharmaceutically acceptable carrier. The composition enhances the effectiveness of radiation therapy, enhancing contrast in X-ray imaging techniques, and when gadolinium is present, provide cancer selective MRI contrast agents.

20 Claims, 26 Drawing Sheets

Specification includes a Sequence Listing.

(56) References Cited

U.S. PATENT DOCUMENTS

| | | | |
|---|---|---|---|
| 5,629,197 A | 5/1997 | Ring et al. | |
| 5,736,348 A | 4/1998 | Goldenberg et al. | |
| 5,739,306 A | 4/1998 | Fung et al. | |
| 5,770,429 A | 6/1998 | Lonberg et al. | |
| 5,869,045 A | 2/1999 | Hellstrom et al. | |
| 5,925,334 A | 7/1999 | Rubin et al. | |
| 5,932,475 A | 8/1999 | Bandman et al. | |
| 6,048,703 A | 4/2000 | Siman et al. | |
| 6,096,532 A | 8/2000 | Armstrong et al. | |
| 6,165,786 A | 12/2000 | Bennett et al. | |
| 6,291,643 B1 | 9/2001 | Zou et al. | |
| 6,306,404 B1 | 10/2001 | LaPosta et al. | |
| 6,325,785 B1 | 12/2001 | Babkes et al. | |
| 6,339,075 B1 | 1/2002 | King et al. | |
| 6,350,452 B1 | 2/2002 | Riss | |
| 6,462,189 B1 | 10/2002 | Koide | |
| 6,506,559 B1 | 1/2003 | Fire et al. | |
| 6,657,103 B1 | 12/2003 | Kucherlapati et al. | |
| 7,259,252 B2 | 8/2007 | Mirkin et al. | |
| 7,314,926 B1 | 1/2008 | Miller et al. | |
| 7,357,928 B2* | 4/2008 | Bates | C07K 14/47 424/1.11 |
| 7,541,150 B2 | 6/2009 | Miller et al. | |
| 7,960,540 B2* | 6/2011 | Trent | A61K 31/711 536/23.1 |
| 8,029,784 B2 | 10/2011 | Bates et al. | |
| 8,114,850 B2* | 2/2012 | Trent | A61K 31/711 435/375 |
| 8,586,717 B2 | 11/2013 | Bates et al. | |
| 8,648,051 B2 | 2/2014 | Miller | |
| 9,260,517 B2* | 2/2016 | Sutkowski | C07K 16/18 |
| 9,452,219 B2* | 9/2016 | Bates | A61K 49/04 |
| 2002/0028488 A1 | 3/2002 | Singh et al. | |
| 2002/0076693 A1 | 6/2002 | Hovanessian et al. | |
| 2003/0086930 A1 | 5/2003 | Mueller | |
| 2003/0194754 A1 | 10/2003 | Miller et al. | |
| 2004/0132049 A1 | 7/2004 | Bates et al. | |
| 2005/0026860 A1 | 2/2005 | Lin et al. | |
| 2005/0053607 A1 | 3/2005 | Bates et al. | |
| 2005/0187176 A1 | 8/2005 | Bates et al. | |
| 2006/0258605 A1 | 11/2006 | Luo et al. | |
| 2009/0017009 A1 | 1/2009 | Bates et al. | |
| 2009/0226914 A1 | 9/2009 | Bates et al. | |
| 2011/0065121 A1 | 3/2011 | Bates et al. | |
| 2011/0091373 A1 | 4/2011 | Pandey et al. | |
| 2011/0111002 A1 | 5/2011 | Pop | |
| 2012/0014942 A1 | 1/2012 | Bates et al. | |
| 2012/0107242 A1* | 5/2012 | Wang | A61K 31/7088 424/9.1 |
| 2013/0115674 A1 | 5/2013 | Sutkowski et al. | |
| 2014/0170076 A1 | 6/2014 | Bates et al. | |
| 2014/0220013 A1 | 8/2014 | Bates et al. | |
| 2016/0179394 A1 | 11/2016 | Malik et al. | |
| 2017/0095562 A1 | 4/2017 | Bates et al. | |
| 2018/0200385 A1 | 7/2018 | Malik et al. | |
| 2019/0192686 A1 | 6/2019 | Malik et al. | |

FOREIGN PATENT DOCUMENTS

| | | |
|---|---|---|
| CA | 2 542 691 | 9/2013 |
| CA | 2 545 806 | 9/2014 |
| DE | 10037861 | 2/2002 |
| JP | 1-503438 | 11/1989 |
| JP | 5-244988 | 9/1993 |
| JP | 07 242566 A | 9/1995 |
| JP | 1995/242566 | 9/1995 |
| JP | 2001-213804 | 8/2001 |
| WO | WO 88/07543 | 10/1988 |
| WO | WO 95/20401 | 8/1995 |
| WO | WO 97/22250 | 6/1997 |
| WO | WO 98/24893 | 6/1998 |
| WO | WO 98/40480 | 9/1998 |
| WO | WO 99/06588 | 2/1999 |
| WO | WO 99/053057 | 10/1999 |
| WO | WO 00/61597 | 10/2000 |
| WO | WO 00/63250 | 10/2000 |
| WO | WO 01/32832 | 5/2001 |
| WO | WO 01/35093 | 5/2001 |
| WO | WO 01/68836 | 9/2001 |
| WO | WO 01/75164 | 10/2001 |
| WO | WO 01/917871 | 12/2001 |
| WO | WO 02/12437 | 2/2002 |
| WO | WO 02/44321 | 6/2002 |
| WO | WO 03/029277 | 4/2003 |
| WO | WO 03/08617 | 10/2003 |
| WO | WO 03/086174 | 10/2003 |
| WO | WO 03/087124 | 10/2003 |
| WO | WO 04/003554 | 1/2004 |
| WO | WO 05/035579 | 4/2005 |
| WO | WO 2007/016466 | 2/2007 |
| WO | WO 09/088837 | 7/2009 |
| WO | WO 2011/062997 | 5/2011 |
| WO | WO 2011/119058 | 9/2011 |
| WO | WO 2012/167173 | 12/2012 |
| WO | 2016/179394 | 11/2016 |

OTHER PUBLICATIONS

16 Pages, Nov. 25, 2008, U.S. Appl. No. 10/607,455, US.
17 Pages, Feb. 6, 2008, U.S. Appl. No. 10/607,455, US.
18 Pages, Aug. 9, 2007, U.S. Appl. No. 10/607,455, US.
7 Pages, Feb. 7, 2007, U.S. Appl. No. 10/607,455, US.
3 Pages, Nov. 6, 2006, U.S. Appl. No. 10/607,455, US.
13 Pages, Jul. 28, 2006, U.S. Appl. No. 10/607,455, US.
19 Pages, Nov. 23, 2005, U.S. Appl. No. 10/607,455, US.
6 Pages, Jun. 29, 2005, U.S. Appl. No. 10/607,455, US.
5 Pages, Aug. 31, 2009, 2004-517874, JP.
4 Pages, Nov. 13, 2003, PCT/US2003/020167, PCT.
69 Pages, Jul. 21, 2009, 03 762 073.9, EP.
5 Pages, Dec. 29, 2008, 03 762 073.9, EP.
8 Pages, Feb. 20, 2008, 03 762 073.9, EP.
9 Pages, May 3, 2007, 03 762 073.9, EP.
5 Pages, Oct. 25, 2006, 03 762 073.9, EP.
3 Pages, Sep. 25, 2008, 2003248724, AU.
10 Pages, Jun. 11, 2008, 03 728 350.4, EP.
65 Pages, Nov. 15, 2007, 03 728 350.4, EP.
5 Pages, Sep. 26, 2005, 03 728 350.4, EP.
4 Pages, Jul. 12, 2005, 03 728 350.4, EP.
7 Pages, May 11, 2009, 2003-583205, JP.
6 Pages, Aug. 3, 2004, PCT/US2003/010745, PCT.
2 Pages, Apr. 18, 2007, 2003234694, AU.
3 Pages, May 6, 2008, 2003234694, AU.
3 Pages, Mar. 1, 2006, 2003234694, AU.
1 Page, Nov. 1, 2004, 2,490,724, CA.
16 Pages, Dec. 8, 2008, 04 785 392.4, EP.
2 Pages, Jun. 25, 2009, 2004279837, AU.
1 Page, Dec. 19, 2007, 2004279837, AU.
12 Pages, Apr. 20, 2006, PCT/US2004/033174, PCT.
22 Pages, Mar. 14, 2005, PCT/US2004/033174, PCT.
9 Pages, Jul. 21, 2009, 2006-534360, JP.
5 Pages, Apr. 16, 2008, U.S. Appl. No. 10/118,854, US.
6 Pages, Sep. 19, 2007, U.S. Appl. No. 10/118,854, US.
7 Pages, Jan. 3, 2007, U.S. Appl. No. 10/118,854, US.
3 Pages, Oct. 17, 2006, U.S. Appl. No. 10/118,854, US.
2 Pages, Aug. 8, 2006, U.S. Appl. No. 10/118,854, US.
12 Pages, Mar. 31, 2006, U.S. Appl. No. 10/118,854, US.
3 Pages, Dec. 15, 2005, U.S. Appl. No. 10/118,854, US.
5 Pages, Jul. 26, 2005, U.S. Appl. No. 10/118,854, US.
14 Pages, Nov. 4, 2004, U.S. Appl. No. 10/118,854, US.
8 Pages, Jul. 1, 2004, U.S. Appl. No. 10/118,854, US.
3 Pages, Sep. 6, 2006, U.S. Appl. No. 10/118,854, US.
4 Pages, Oct. 25, 2007, U.S. Appl. No. 10/683,480, US.
6 Pages, Jun. 1, 2007, U.S. Appl. No. 10/683,480, US.
4 Pages, Nov. 27, 2006, U.S. Appl. No. 10/683,480, US.
2 Pages, Aug. 8, 2006, U.S. Appl. No. 10/683,480, US.
10 Pages, Jun. 5, 2006, U.S. Appl. No. 10/683,480, US.
10 Pages, Feb. 23, 2006, U.S. Appl. No. 10/683,480, US.
33 Pages, Nov. 13, 2009, U.S. Appl. No. 12/041,969, US.

(56) References Cited

OTHER PUBLICATIONS

2 Pages, Dec. 29, 2009, 2,490,724, CA.
4 Pages, Apr. 12, 2010, 04 785 392.4, EP.
3 Pages, Apr. 14, 2010, 2003-583205, JP.
5 Pages, May 12, 2010, 2006-534360, JP.
10 Pages, Jun. 7, 2010, U.S. Appl. No. 12/041,969, US.
2 Pages, Jul. 20, 2010, 2,490,724, CA.
9 Pages, Sep. 28, 2010, U.S. Appl. No. 12/345,626, US.
3 Pages, Oct. 18, 2010, U.S. Appl. No. 12/041,969, US.
2 Pages, Feb. 1, 2010, U.S. Appl. No. 10/607,455, US.
2 Pages, Jun. 27, 2008, U.S. Appl. No. 10/607,455, US.
3 Pages, Sep. 18, 2006, U.S. Appl. No. 10/607,455, US.
9 Pages, Dec. 21, 2010, U.S. Appl. No. 12/604,212, US.
34 Pages, Mar. 30, 2011, U.S. Appl. No. 12/604,212, US.
3 Pages, May 21, 2010, 2,489,520, CA.
3 Pages, Mar. 15, 2011, 2,489,520, CA.
2 Pages, Jun. 15, 2010, 2,490,724, CA.
4 Pages, Nov. 23, 2010, U.S. Appl. No. 12/041,969, US.
3 Pages, Sep. 29, 2010, 2003-583205, JP.
6 Pages, Aug. 3, 2004, PCT/US03/10745, PCT.
33 Pages, Dec. 27, 2010, U.S. Appl. No. 12/345,626, US.
33 Pages, Jan. 7, 2011, U.S. Appl. No. 12/345,626, US.
7 Pages, Jul. 14, 2009, PCT/US2008/088491, PCT.
21 Pages, Sep. 21, 2009, PCT/US2008/088491, PCT.
11 Pages, Jul. 15, 2010, PCT/US2008/088491, PCT.
3 Pages, Jun. 15, 2011, U.S. Appl. No. 12/041,969, US.
6 Pages, Jun. 9, 2011, U.S. Appl. No. 12/041,969, US.
4 Pages, Jun. 3, 2011, 2,546,730, CA.
15 Pages, Jul. 28, 2011, U.S. Appl. No. 12/345,626, US.
14 Pages, Sep. 28, 2011, U.S. Appl. No. 12/604,212, US.
2 Pages, Jan. 26, 2012, U.S. Appl. No. 12/604,212, US.
5 Pages, Nov. 7, 2011, 04 785 392.4, EP.
5 Pages, Dec. 19, 2011, 2011-127396, JP.
3 Pages, Jan. 20, 2012, 2010202113, AU.
2 Pages, Jul. 18, 2012, 2,546,730, CA.
34 Pages, Jul. 10, 2012, U.S. Appl. No. 13/116,319, US.
4 Pages, Aug. 6, 2012, 2011-127396, JP.
4 Pages, Mar. 8, 2013, 2,546,730, CA.
17 Pages, Feb. 26, 2013, U.S. Appl. No. 13/116,319, US.
8 Pages, Apr. 26, 2013, 04 785 392.4, EP.
3 Pages, Jun. 18, 2013, U.S. Appl. No. 13/116,319, US.
52 Pages, Jul. 15, 2013, U.S. Appl. No. 12/604,212, US.
7 Pages, Jul. 6, 2013, U.S. Appl. No. 13/116,319, US.
15 Pages, Sep. 19, 2012, PCT/US2012/040577, PCT.
3 Pages, Sep. 12, 2013, 04 785 392.4, EP.
6 Pages, Oct. 14, 2013, 04 785 392.4, EP.
8 Pages, Dec. 12, 2013, PCT/US2012/040577, PCT.
7 Pages, Oct. 15, 2013, 04 785 392.4, EP.
2 Pages, Jan. 24, 2014, 12730288.3, EP.
5 Pages, Sep. 5, 2011, 2011-127396, JP.
6 Pages, Mar. 10, 2014, 2012-266961, JP.
4 Pages, Oct. 3, 2014, 12730288.3, EP.
5 Pages, Jan. 20, 2015, 12730288.3, EP.
5 Pages, Feb. 9, 2015, 2012-266961, JP.
5 Pages, Feb. 4, 2015, U.S. Appl. No. 14/059,211, US.
3 Pages, Mar. 6, 2015, 2,546,730, CA.
7 Pages, Mar. 30, 2015, 12730288.3, EP.
44 Pages, May 20, 2015, U.S. Appl. No. 14/059,211, US.
3 Pages, Jul. 15, 2015, U.S. Appl. No. 14/122,617, US.
14 Pages, Jul. 20, 2015, U.S. Appl. No. 14/122,617, US.
2 Pages, Sep. 17, 2015, U.S. Appl. No. 14/127,617, US.
56 Pages, Sep. 29, 2015, U.S. Appl. No. 14/122,617, US.
17 Pages, Dec. 8, 2015, U.S. Appl. No. 14/059,211, US.
15 Pages, Jan. 22, 2016, U.S. Appl. No. 17/122,617, US.
2 Pages, Jan. 28, 2016, 12730288.3, EP.
8 Pages, Mar. 2, 2016, 15182208.7, EP.
6 Pages, Mar. 29, 2016, U.S. Appl. No. 14/059,211, US.
3 Pages, Apr. 18, 2016, U.S. Appl. No. 14/122,617, US.
14 Pages, May 19, 2016, U.S. Appl. No. 14/122,617, US.
15 Pages, Jul. 19, 2016, U.S. Appl. No. 14/059,211, US.
12 Pages, Jul. 21, 2016, PCT/US2016/030985, WO.
1 Page, Aug. 17, 2016, 2,546,730, CA.
12 Pages, Mar. 17, 2017, U.S. Appl. No. 14/059,211, US.
4 Pages, May 15, 2017, 15182208.7, EP.
16 Pages, Oct. 19, 2017, PCT/US2017/045169, WO.
3 Pages, Jan. 3, 2018, 16723223.0, EP.
9 Pages, Jan. 12, 2018, U.S. Appl. No. 15/240,780, US.
U.S. Appl. No. 15/240,780, filed Aug. 18, 2016.
U.S. Appl. No. 16/322,369, filed Jan. 31, 2019, Aug. 2, 2017.
59 Pages, Jul. 27, 2018, U.S. Appl. No. 15/240,780, US.
25 Pages, Jan. 23, 2019, U.S. Appl. No. 15/240,780, US.
6 Pages, Jan. 28, 2019, 18185333.4, EP.
5 Pages, Mar. 20, 2019, U.S. Appl. No. 15/240,780, US.
4 Pages, Apr. 30, 2019, U.S. Appl. No. 15/240,780, US.
5 Pages, May 2, 2019, 16723223.0, EP.
Sawyers, C., "Targeted cancer therapy", Nature, vol. 432, pp. 294-297, (2004.).
Tacar, O. et al., "Doxorubicin: an update on anticancer molecular action, toxicity and novel drug delivery systems", Journal of Pharmacy and Pharmacology, vol. 65, pp. 157-170, (2013).
Kopechek, J.A. et al., "Accumulation of phase-shift nanoemulsions to enhance MR-guided ultrasound-mediated tumor ablation in vivo", Journal of Healthcare Engineering, vol. 4, No. 1, pp. 109-126, (2013).
Rapoport, N., "Phase-shift, stimuli-responsive perfluorocarbon nanodroplets for drug delivery to cancer", Wiley Interdiscip Rev Nanomed Nanobiotechnology, vol. 4, No. 5, pp. 492-510, (2012).
Marshalek, J.P. et al., "Intracellular delivery and ultrasonic activation of folate receptor-targeted phase-change contrast agents in breast cancer cells in vitro", Journal of Controlled Release, vol. 243, pp. 69-77, (2016).
Kopeohek, J.A. et al., "Cavitation-enhanced MR-guided focused ultrasound ablation of rabbit tumors in vivo using phase shift nanoemuisions", Physics in Medicine and Biology, vol. 59, No. 13, pp. 3465-3481, (2014).
Strohm, E. et al., "Vaporization of perfluorocarbon droplets using optical irradiation", Biomedical Optics Express, vol. 2, No. 6, pp. 1432-1442, (2011).
Wilson, K. et al., "Biomedical photoacoustics beyond thermal expansion using triggered nanodroplet vaporization for contrast-enhanced imaging", Nature Communications, vol. 3, No. 618, pp. 1-10, (2012).
Latorre, A. et al., "DNA and aptamer stabilized gold nanoparticles for targeted delivery of anticancer therapeutics", Nanoscale, vol. 6, pp. 7436-7442, (2014).
Khader, M. et al., "Thymoquinone: an emerging natural drug with a wide range of medical applications", Iranian Journal of Basic Medical Sciences, vol. 17, pp. 950-957, (2014).
Woo, C.C. et al., "Thymoquinone: potential cure for inflammatory disorders and cancer", Biochemical Pharmacology, vol. 83, pp. 443-451, (2012).
Duncanson, W.J. et al., "Microfluidic fabrication of perfluorohexane-shelled double emulsions for controlled loading and acoustic-triggered release of hydrophilic agents", Langmuir, vol. 30, pp. 13765-13770, (2014).
Fabiilli, M.L. et al., "Delivery of chlorambucil using an acoustically-triggered perfluoropentane emulsion", Ultrasoundin Medicine and Biology, vol. 36, No. 8. pp. 1364-1375, (2010).
Kopechek, J.A. et al., "Synthesis of phase-shift nanoemulsions with narrow size distributions for acoustic droplet vaporization and bubble-enhanced ultrasound-mediated ablation", Journal of Visualized Experiments, vol. 67, e4308 pp. 1-5, (2012).
Abaza, M.S.I, et al, "Effects of amino acid substitutions outside an antigenic site on protein binding to monoclonal antibodies of predetermined specificity obtained by peptide immunization: Demonstration with region 94-100 (antigenic site 3) of myoglobin", Journal of Protein Chemistry, vol. 11, No. 5, pp. 433-444, (1992).
Agrawal, S, et al, "Antisense therapeutics: is it as simple as complementary base recognition?", Mol Med Today, vol. 6, No. 2, pp. 72-81, (2000).
Aihara, M, et al, "The frequency of apoptosis correlates with the prognosis of Gleason Grade 3 adenocarcinoma of the prostate", Cancer, vol. 75, No. 2, pp. 522-529, (1995).

(56) References Cited

OTHER PUBLICATIONS

Aihara, M, et al, "Frequency of apoptotic bodies positively correlates With Gleason grade in prostate cancer", Hum Pathol, vol. 25, No. 8, pp. 797-801, (1994).
Ali, S, et al, "Absorption, distribution, metabolism, and excretion of a respirable antisense oligonucleotide for asthma", Am J Respir Crit Care Med, vol. 163, No. 4, pp. 989-993, (2001).
Altman, S, "Nobel lecture. Enzymatic cleavage of RNA by RNA", Biosci Rep, vol. 10, No. 4, pp. 317-337, (1990).
Alvarex-Gonzalez, R, et al, "Selective loss of poly(ADP-ribose) and the 85-kDa fragment of ply(ADP-ribose) polymerase in nucleoli during alkylation-induced apoptosis of HeLa Cells", J Biol Chem., vol. 274, No. 45, pp. 32122-32126, (1999).
Anderson, H.J, et al, "Flow cytometry of mitotic cells", Exp Cell Research, vol. 238, No. 2, pp. 498-502, (1998).
Andrade, F, et al, "Apoptosis in systemtic lupus erythematosus", Rheumatic Diseases Clinics of North America, vol. 2, (2000).
Awang, G, et al, "Mode of dimerization of HIV-1 genomic RNA", Biochemistry, vol. 32 No. 42, pp. 11453-11457, (1993).
Ballou, B, et al, "Three-Dimensional Imaging of Nucleolin Trafficking in Normal Cells, Transfectants, and Heterokaryons", SPIE, vol. 2680, pp. 124-131, (1996).
Ballou, B, et al, "Tumor Detection and Visualization Using Cyanine Fluorochrome-Labeled Antibodies", Biotechnol Prog, vol. 13, pp. 649-658, (1997).
Ballou, B, et al, "Tumor Labeling in Vivo Using Cyanine-Conjugated Monoclonal Antibodies", Cancer Immunol Immunother, vol. 41, pp. 257-263, (1995).
Ballou, B, et al, Abstract of "Cyanine Fluorocrome-Labeled Antibodies In Vivo: Assessment of Tumor Imaging Using Cy3, Cy5, Cy5.5, and Cy7", Cancer Detect Prev, vol. 22, No. 3, pp. 251-257, (1998).
Baran, N, et al, "The SV40 large T-antigen helicase can unwind four stranded DNA structures linked by G-quartets", Nucleic Acids Research, vol. 25, No. 2, pp. 297-303, (1997).
Barton, C.M, et al, "Antisense oligonucleotides directed against p53 have antiproliferative effects unrelated to effects on p53 expression", Br J Cancer, vol. 71, No. 3, pp. 429-437, (1995).
Bates, P.J, et al, "Antiproliferative activity of G-rich oligonucleotides correlates with protein binding", The Journal of Biological Chemistry, vol. 274, No. 37, pp. 26369-26377, (1999).
Beedassy, A, et al, "Chemotherapy in advanced prostate cancer", Semin Oncol, vol. 26, No. 4, pp. 428-438, (1999).
Beltinger, C, et al, "Binding, uptake, and intracellular trafficking of phosphorothioate-modified oligodeoxynucleotides", J Clin Invest, vol. 95, No. 4, pp. 1814-1823, (1995).
Benimetskaya, L, et al, "Formation of a G-tetrad and higher order structures correlates with biological activity of the Re1A (NF-kappaB p65) 'antisense' oligodeoxynucleotide", Nucleic Acids Research, vol. 25, No. 13, pp. 2648-2656, (1997).
Benton, B.M, et al, "A novel FK506- and rapamycin-binding protein (FPR3 gene product) in the yeast *Saccharomyces cerevisiae* is a praline rotamase localized to the nucleolus", J Cell Biol, vol. 127, No. 3, pp. 623-639, (1994).
Bergsmedh, A, et al, "Horizontal transfer of oncogenes by uptake of apoptotic bodies", Proc Natl Acad Science USA, vol. 98, No. 11, pp. 6407-6411, (2001).
Bergsmedh, A, et al, "Loss of the p21(Cip1/Waf1) cyclin kinase inhibitor results in propagation of horizontally transferred DNA", Cancer Research, vol. 62, No. 2, pp. 575-579, (2002).
Bernardi, F.D, et al, "A prognostic model of survival in surgically resected squamous cell carcinoma of the lung using clinical, pathologic, and biologic markers", Mod Pathol, vol. 10, No. 10, pp. 992-1000, (1997).
Bernstein, E, et al, "Role for a bidentate ribonuclease in the initiation step of RNA interference", Nature, vol. 409, No. 6818, pp. 363-366, (2001).
Bharti, A.K, et al, "Identification of a nucleolin binding site in human topoisomerase I", J Biol Chem, vol. 271, No. 4, pp. 1993-1997, (1996).

Biggiogera, M, et al, "Heterogeneous ectopic RNP-derived structures (HERDS) are markers of transcriptional arrest", FASEB J, vol. 14, No. 5, pp. 828-834, (2000).
Biscotti, C.V, et al, "Apoptotic bodies: a consistent morphologic feature of endocervical adenocarcinoma in situ", American Journal of Surgical Pathology, vol. 22, No. 4, pp. 434-439, (1998).
Bishop, J.S, et al, "Intramolecular G-quartet motifs confer nuclease resistance to a potent anti-HIV oligonucleotide", J Biol Chem, vol. 271, No. 10, pp. 5698-5703, (1996).
Blau, H.M, et al, "Tet B or not tet B: Advances in tetracycline-inducible gene expression", Proc Natl Acad Science USA, vol. 96, pp. 797-799, (1999).
Bock, L.C, et al, "Selection of single-stranded DNA molecules that bind and inhibit human thrombin", Nature, vol. 355, No. 6360, pp. 564-566, (1992).
Borer, R.A, et al, "Major nucleolar proteins shuttle between nucleus and cytoplasm", Cell, vol. 56, No. 3, pp. 379-390, (1989).
Borggrefe, T, et al, "A B-cell-specific DNA recombination complex", J Biol Chem, vol. 273, No. 27, pp. 17025-17035, (1998).
Borst, P, et al, "Does resistance to apoptosis affect clinical response to antitumor drugs?", Drug Resist Update, vol. 4, No. 2, pp. 129-131, (2001).
Bortul, R, et al, "Nuclear changes in necrotic HL-60 cells", J Cell Biochem, vol. 81, No. S36, pp. 19-31, (2001).
Boulares, A.H, et al, "Role of poly (ADP-ribose) polymerase (PARP) cleavage in apoptosis. Caspase 3-resistant PARP mutant increases rates of apoptosis in transfected cells", Journal of Biological Chemistry, vol. 274, No. 33, pp. 22932-22940, (1999).
Boulares, A.H, et al, "Roles of DNA fragmentation factor and poly(ADP-ribose) polymerase in an amplification phase of tumor necrosis factor-induced apoptosis", Journal of Biological Chemistry, vol. 276, No. 41, pp. 38185-38192, (2001).
Brockstedt, E, et al, "Identification of apoptosis-associated proteins in a human Burkitt lymphoma cell line. Cleavage of heterogeneous nuclear ribonucleoprotein A1 by caspase 3", J Biol Chem, vol. 273, No. 43, pp. 28057-28064, (1998).
Brown, J.M, et al, "Apoptosis:mediator or mode of cell killing by anticancer agents?", Drug Resist Update, vol. 4, No. 2, pp. 135-136, (2001).
Brustmann, H, "Apoptotic bodies as a morphological feature in serous ovarian carcinoma: correlation with nuclear grade, Ki-67 and mitotic indices", Pathol Res Pract, vol. 198, No. 2, pp. 85-90, (2002).
Burgess, T.L, et al, "The antiproliferative activity of c-myb and c-myc antisense oligonucleotides in smooth muscle cells is caused by a nonantisense mechanism", Proc Natl Acad Science USA, vol. 92, No. 9, pp. 4051-4055, (1995).
Buys, C.H, "Telomeres, telomerase, and cancer", N Engl J Med, vol. 342, No. 17, pp. 1282-1283, (2000).
Callebaut, C, et al, "Identification of V3 loop-binding proteins as potential receptors implicated in the binding of HIV particles to CD4(+) cells", J Biol Chem, vol. 273, No. 34, pp. 21988-21997, (1998).
Cannavo, G, et al, "Abnormal intracellular kinetics of cell-cycle-dependent prote ns in lymphocytes from patients infected with human immunodeficiency virus: a novel biologic link between immune activation, accelerated t-cell turnover, and high levels of apoptosis", Blood, vol. 97, No. 6, pp. 1756-1764, (2001).
Carney, D.N, et al, "Establishment and identification of small cell lung cancer cell lines having classic and variant features", Cancer Research, vol. 45, pp. 2913-2923, (1985).
Carvalho, P.E, et al, "Useful prognostic panel markers to express the biological tumor status in resected lung adenocarcinomas", Jpn J Clin Oncol, vol. 30, No. 11, pp. 478-486, (2000).
Cech, T.R, "Biologic catalysis by RNA", Harvey Lect, vol. 82, pp. 123-144, (1988).
Chern, J.H, et al, "Usefulness of AgNOR score in differentiating benign from malignant pulmonary aspiration cytology", Acta Cytol, vol. 41, No. 2, pp. 393-398, (1997).
Choi, N.G, et al, "Apoptosis and nuclear shapes in benign prostate hyperplasia and prostate adenocarcinoma: comparison with and relation to Gleason score", Int J Urol, vol. 6, No. 1, pp. 13-18, (1999).

(56) References Cited

OTHER PUBLICATIONS

Cole, S.P, et al, "Antibody production by human X human hybridomas in serum-free medium", J Immunol Methods, vol. 78, No. 2, pp. 271-278, (1985).

Coligan, J.E. et al., "Production of Monoclonal Antibodies", Current Protocols in Immunology, vol. 1, pp. 2.5.1-2.6.7, Wiley, New York, (1991).

Coqueret, O, et al, "Functional interaction of STAT3 transcription factor with the cell cycle inhibitor p21$^{WAF1/CIP1/SDI1}$", J Biol Chem, vol. 275, No. 25, pp. 18794-18800, (2000).

Cowan, K.H, et al, "Dihydrofolate reductase gene amplification and possible rearrangement in estrogen-responsive methotrexate-resistant human breast cancer cells", J Biol Chem, vol. 257, No. 24, pp. 15079-15086, (1982).

Crooke, S., "Oligonucleotide therapeutics: a prospectus." Antisense Research arid Development, vol. 3, No. 1, pp. 1-2, (1993).

Crooke, S, "Progress in antisense technology: the end of the beginning", Methods Enzymol, vol. 313, pp. 3-45, (1999).

D'Amours, D, et al, "Poly(ADP-ribosyl)ation reactions in the regulation of nuclear functions", Biochem J, vol. 342, pt. 2, pp. 249-268, (1999).

Dagle, J.M, et al, "Selective degradation of targeted mRNAs using partially modified oligonucleotides", Methods Enzymol, vol. 313, pp. 420-436, (1999).

Daniely, Y, et al, "Formation of a complex between nucleolin and replication protein A after cell stress prevents initiation of DNA replication", J Cell Biology, vol. 149, No. 4, pp. 799-810, (2000).

Dapic, V, et al, "Antiproliferative activity of G-Quartet-forming oligonucleotides with backbone and sugar modifications", Biochemistry, vol. 41, No. 11, pp. 3676-3685, (2002).

David, K, et al, "Initial characterization of the apoptosis-inducing receptor for natural human anti-neuroblastoma IgM", Med Pediatr Oncol, vol. 36, No. 1, pp. 251-257, (2001).

David-Pfeuty, T, "Potent inhibitors of cyclin-dependent kinase 2 induce nuclear accumulation of wild-type p53 and nucleolar fragmentation in human untransformed and tumor-derived cells", Oncogene, vol. 18, No. 52, pp. 7409-7422, (1999).

Davis, K.A, et al, "Staining of cell surface human CD4 with 2'-F-pyrimidine-conlainirg RNA aptamers for flow cytometry", Nucleic Acids Research, vol. 26, pp. 3915-3924, (1998).

De Jong, J.S, et al, "Number of apoptotic cells as a prognostic marker in invasive breast cancer", Br J Cancer, vol. 82, No. 2, pp. 368-373, (2000).

Dempsey, L.A, et al, "A specific isoform of hnRNP D interacts with DNA in the LR1 heterodimer: canonical RNA binding motifs in a sequence-specific duplex DNA binding protein", J Biol Chem, vol. 273, No. 44, pp. 29224-29229, (1998).

Dempsey, L.A, et al, "G4 DNA binding by LR1 and its subunits, nucleolin and hnRNP D, A role for G-G pairing in immunoglobulin switch recombination", J Biol Chem, vol. 274, No. 2, pp. 1066-1071, (1999).

Deng, J.S, et al, "Internalization of anti-nucleolin antibody into viable HEp-2 cells", Mol Biol Rep, vol. 23, No. 3-4, pp. 191-195, (1996).

Derenzini, M. "The AgNORs", Micron, vol. 31, No. 2, pp. 117-120, (2000).

Derenzini, M, et al, "The quantity of nucleolar proteins nucleolin and protein B23 is related to cell doubling time in human cancer cells", Lab Invest, vol. 73, No. 4, pp. 497-502, (1995).

Desnoyers, S, et al, "Alteration of the nucleolar localization of poly(ADP-ribose) polymerase upon treatment with transcription inhibitors", Exp Cell Research, vol. 227, No. 1, pp. 146-153, (1996).

Dickinson, L.A, et al, "Nucleolin is a matrix attachment region DNA-binding protein that specifically recognizes a region with high base-unpairing potential", Mol Cell Biology, vol. 15, No. 1, pp. 456-465, (1995).

Dranovsky, A, et al, "Cdc2 phosphorylation of nucleolin demarcates mitotic stages and alzheimer's disease pathology", Neurobiol Aging, vol. 22, No. 4, pp. 517-528, (2001).

Drews, J, "Drug discovery: a historical perspective", Science, vol. 287, No. 5460, pp. 1960-1964, (2000).

Drews J, et al, "Classic drug targets (special pull-out)", Nature Biotechnology, vol. 15, (1997).

Dryden, S, et al, "The lack of specificity of neuropeptide Y (NPY) antisense oligodeoxynucleotides administered intracerebroventricularly in inhibiting food intake and NPY gene expression in the rat hypothalamus", J Endocrinol, vol. 157, No. 1, pp. 169-175, (1998).

Dumler, I, et al, "Urokinase-induced mitogenesis is mediated by casein kinase 2 and nucleolin", Curr Biol, vol. 9, No. 24, pp. 1468-1476, (1999).

Dundr, M, et al, "The dynamics of postmitotic reassembly of the nucleolus", J Cell Biol, vol. 150, No. 3, pp. 433-446, (2000).

Edwards, T.K, et al, "Role for nucleolin/Nsr1 in the cellular localization of topoisomerase I", J Biol Chem, vol. 275, No. 46, pp. 36181-36188, (2000).

Eguchi, K, "Apoptosis in autoimmune diseases", Intern Med, vol. 40, No. 4, pp. 275-284, (2001).

Erard, M.S, et al, "A major nucleolar protein, nucleolin, induces chromatin decondensation by binding to histone H1", Eur J Biochem, vol. 175, No. 3, pp. 525-530, (1988).

European Search Report for Application No. 03728350.4 dated Jul. 12, 2005.

Facompre, M, et al, "Apoptotic response of HL-60 human leukemia cells to the antitumor drug NB-506, a glycosylated indolocarbazole inhibitor of topoisomerase 1", Biochem Pharmacel, vol. 61, No. 3, pp. 299-310, (2001).

Feltzer, R.E, et al, "Alkaline proteinase inhibitor of Pseudomonas aeruginosa. Interaction of native and N-terminally truncated inhibitor proteins with Pseudomonas metalloproteinases", J Biol Chem, vol. 275, No. 28, pp. 21002-21009, (2000).

Fielding, P, et al, "Heterogeneous nuclear ribonucleoprotein A2/B1 up-regulation in bronchial lavage specimens: a clinical marker of early lung cancer detection", Clincal Cancer Research, vol. 5, No. 12, pp. 4048-4052, (1999).

Fry, M, et al, "Human Werner syndrome DNA helicase unwinds tetrahelical structures of the fragile X syndrome repeat sequence d(CGG)n", J Biol Chem, vol. 274, No. 18, pp. 12797-12802, (1999).

Fry, M, et al, "The fragile X syndrome d(CGG)n nucleotide repeats form a stable tetrahelical structure", Proc Natl Acad Science USA, vol. 91, No. 11, pp. 4950-4954, (1994).

Gascoyne, R.D, et al, "Prognostic significance of Bcl-2 protein expression and Bcl-2 gene rearrangement in diffuse aggressive non-Hodgkin's lymphoma", Blood, vol. 90, No. 1, pp. 244-251, (1997).

Gautier, F, et al, "Identification of an apoptotic cleavage product of BARD1 as an autoantigen: a potential factor in the antitumoral response mediated by apoptotic bodies", Cancer Research, vol. 60, No. 24, pp. 6895-6900, (2000).

Gautier, F, et al, "Production and characterisation of a monoclonal antibody specific for apoptotic bodies derived from several tumour cell lines", Journal of Immunological Methods, vol. 228, pp. 49-58, (1999).

Gavrieli, Y, et al, "Identification of programmed cell death in situ via specific labeling of nuclear DNA fragmentation", The Journal of Cell Biology, vol. 119, No. 3, pp. 493-501, (1992).

Gey, G, et al, "Tissue culture studies of the proliferative capacity of cervical carcinoma and normal epithelium", Cancer Research, vol. 12, pp. 264, (1952).

Ghosh, M, et al, "Apoptosis in squamous cell carcinoma of the lung: correlation with survival and clinicopathological features", J Clin Pathol, vol. 54, No. 2, pp. 111-115, (2001).

Giaccone, G, et al, "Neuromedin B is present in lung cancer cell lines", Cancer Research, vol. 52, pp. 2732s-2736s, (1992).

Gibbs, J.B, "Mechanism-based target identification and drug discovery in cancer research", Science, vol. 287, No. 5460, pp. 1969-1973, (2000).

Gil, D, et al, "Intracellular redistribution of nucleolin upon interaction with the CD3epsilon chain of the T cell receptor complex", J Biol Chem, vol. 276, No. 14, pp. 11174-11179, (2001).

(56) References Cited

OTHER PUBLICATIONS

Giles, R.V, et al, "Selecting optimal oligonucleotide composition for maximal antisense effect following streptolysin O-mediated delivery into human leukaemia cells", Nucleic Acids Research, vol. 26, No. 7, pp. 1567-1575, (1998).
Gilloteaux, J. et al., "Cancer cell necrosis by autoschizis: synergism of antitumor activity of vitamin C: vitamin $K_3$ on human bladder carcinoma T24 cells", Scanning, vol. 20, No. 8, pp. 564-575, (1998).
Ginisty, H, et al, "Structure and functions of nucleolin", J Cell Science, vol. 112, Pt. 6, pp. 761-772, (1999).
Giovannangeli, C. et al, "Progress in developments of triplex-based strategies", Antisense & Nucleic Acid Drug Development, vol. 7, No. 4, pp. 413-421, (1997).
Giraldo, R, et al, "The yeast telomere-binding protein RAP1 binds to and promotes the formation of DNA quadruplexes in telomeric DNA", Embo J, vol. 13, No. 10, pp. 2411-2420, (1994).
Green, D. W, et al, "Beta-catenin antisense treatment decreases beta-catenin expression and tumor growth rate in colon carcinoma xenografts", J Surg Res, vol. 101, No. 1, pp. 16-20, (2001).
Grinstein, E, et al, "Nucleolin as Activator of Human Papillomavirus Type 18 Oncogene Transcription in Cervical Cancer", J Exp Med, vol. 196, No. 8, pp. 1067-1078, The Rockefeller University Press, (2002).
Gudas, J.M, et al, "Drug-resistant breast cancer cells frequently retain expression of a functional wild-type p53 protein", Carcinogenesis, vol. 17, No. 7, pp. 1417-1427, (1996).
Haese, A, "Serum markers for early detection and staging of prostate cancer, status report on current and future markers", Urologe A, vol. 42, No. 9, pp. 1172-1187, (2003).—(Abstract Only).
Halicka, H.D, et al, "Segregation of RNA and separate packaging of DNA and RNA in apoptotic bodies during apoptosis", Exp Cell Research, vol. 260, No. 2, pp. 248-256, (2000).
Hanahan, D, et al, "The hallmarks of cancer", Cell, vol. 100, No. 1, pp. 57-70, (2000).
Hanakahi, L.A, et al, "High affinity interactions of nucleolin with G-G-paired rDNA", J Biol Chem, vol. 274, No. 22, pp. 15908-15912, (1999).
Hanakahi, L.A, et al, "Nucleolin is one component of the B cell-specific transcription factor and switch region binding protein, LR1", Proc Natl Acad Science USA, vol. 94, No. 8, pp. 3605-3610, (1997).
Harms, G, et al, "Identification of nucleolin as a new L-selectin ligand", Biochem J, vol. 360, pp. 531-538, (2001).
Herceg, Z, et al, "Failure of poly(ADP-ribose) polymerase cleavage by caspases leads to induction of necrosis and enhanced apoptosis", Mol Cell Biol, vol. 19, No. 7, pp. 5124-5133, (1999).
Hirata, D, et al, "Nucleolin as the earliest target molecule of autoantibodies produced in MRL/lpr lupus-prone mice", Clin Immunol, vol. 97, No. 1, pp. 50-58, (2000).
Hirsch, F.R, et al, "Early detection of lung cancer: clinical perspectives of recent advances in biology and radiology", Clinical Cancer Research, vol. 7, No. 1, pp. 5-22, (2001).
Holdenrieder, S, et al, "Nucleosomes in serum as a marker for cell death", Clin Chem Lab Med, vol. 39, No. 7, pp. 596-605, (2001).
Holdenrieder, S, et al, "Nucleosomes in serum of patients with benign and malignant diseases", Int. J. Cancer, vol. 95, pp. 114-120, (2001).
Holdenrieder, S, et al, "Circulating nucleosomes in serum", Annals New York Academy of Sciences, vol. 945, pp. 93-102, (2001).
Holdenrieder, S, et al, "Quantification of nucleosomes in serum by the cell death detection ELISAplus", Biochemica, No. 1, pp. 25-27, (2002), (http://www.roche-applied-science.com/biochemica/no1_02/PDF/p25.pdf).
Holmgren, L, et al, Horizontal transfer of DNA by the uptake of apoptotic bodies, Blood, vol. 93, No. 11, pp. 3956-3963, (1999).
Horky, M, et al, "Segregation of nucleolar components coincides with caspase-3 activation in cisplatin-treated HeLa cells", J Cell Science, vol. 114, pt. 4, pp. 663-670, (2001).

Hovanessian, A.G, et al, "The cell-surface-expressed nucleolin is associated with the actin cytoskeleton", Experimental Cell Research, vol. 261, pp. 312-328, (2000).
Huang, Z, "Bcl-2 family proteins as targets for anticancer drug design", Oncogene, vol. 19, No. 56, pp. 6627-6631, (2000).
Iida, A, et al, "Inducible gene expression by retrovirus-mediated transfer of a modified tetracycline-regulated system", J Virol, vol. 70, No. 9, pp. 6054-6059, (1996).
International Search Report dated Nov. 13, 2003 for PCT application No. PCT/US03/20167.
International Search Report dated Aug. 3, 2004 for PCT application No. PCTIUS03/10745.
International Search Report dated Mar. 14, 2005 for PCT application No. PCT/US04/033174.
Irving, R.A, et al, "Ribosome display and affinity maturation: from antibodies to single v-domains and steps towards cancer therapeutics", J Immunol Methods, vol. 248, issues 1-2, pp. 31-45, (2001).
Ishikawa, F, et al, "Nuclear proteins that bind the pre-mRNA 3' splice site sequence r(UUAG/G) and the human telomeric DNA sequence d(TTAGGG)n", Mol Cell Biology, vol. 13, No. 7, pp. 4301-4310, (1993).
Jordan, P, et al, "Major cell surface-located protein substrates of an ecto-protein kinase are homologs of known nuclear proteins", Biochemistry, vol. 33, No. 49, pp. 14696-14706, (1994).
Jungblut, P.R, et al, "Proteomics in human disease: cancer, heart and infectious diseases", Electrophoresis, vol. 20, No. 10, pp. 2100-2110, (1999).
Kamma, H, et al, "Interaction of hnRNP A2/B1 isoforms with telomeric ssDNA and the in vitro function", Biochem Biophys Res Commun, vol. 280, No. 3, pp. 625-630, (2001).
Kaneko, S, et al, "Nucleolar organizer regions as a prognostic indicator for stage I non-small cell lung cancer", Cancer Research, vol. 51, No. 15, pp. 4008-4011, (1991).
Kennedy, T.C, et al, "Screening for lung cancer revisited and the role of sputum cytology and fluorescence bronchoscopy in a high-risk group", Chest, vol. 117, supplemental 4, pp. 72S-79S, (2000).
Keough, T, et al, "A method for high-sensitivity peptide sequencing using postsource decay matrix-assisted laser desorption ionization mass spectrometry", Proc Natl Acad Science USA, vol. 96, No. 13, pp. 7131-7136, (1999).
Kerr, J.F, et al, "Apoptosis: a basic biological phenomenon with wide-ranging implications in tissue kinetics", Br J Cancer, vol. 26, pp. 239-257, (1972).
Ketting, R.F, et al, "Dicer functions in RNA interference and in synthesis of small RNA involved in developmental timing in C elegans", Genes Dev, vol. 15, No. 20, pp. 2654-2659, (2001).
Kibbey, M.C, et al, "A 110-kD nuclear shuttling protein, nucleolin, binds to the neurite-promoting IKVAV site of laminin-1", J Neurosci Research, vol. 42, No. 3, pp. 314-322, (1995).
Kim, C.S, et al, "A micro double capillary method for rheologic measurements of lower airway secretions", Bull Eur Physiopathol Respir, vol. 18, pp. 915-927, (1982).
Knorre, D.G. et al., "Antisense oligonucleotide derivatives as gene-targeted drugs", Biomed Sci, vol. 1, No. 4, pp. 334-343, (1990).
Kohler, G, et al, "Continuous cultures of fused cells secreting antibody of predefined specificity", Nature, vol. 256, pp. 495-497, (1975).
Kohler, P.O, "Isolation, cloning, and hybridization of endocrine cell lines", Methods Enzymol, vol. 39, pp. 109-128, (1975).
Krantz, S, et al, "Purification and partial amino acid sequencing of a fructosyllysine-specific binding protein from cell membranes of the monocyte-like cell line U937", Biochim Biophys Acta, vol. 1266, No. 1, pp. 109-112, (1995).
Kuby, J, "Antigens", Immunology, Second Edition, chapter 4, pp. 85-96, W.H. Freeman and Company, New York, (1994).
Kumar, R.K, et al, "Improved double immunofluorescence for confocal laser scanning microscopy", J Histochem Cytochem, vol. 47, No. 9, pp. 1213-1218, (1999).
Kwiatkowski, B.A, et al, "Identification and cloning of a novel chromatin-associated protein partner of Epstein-Barr nuclear protein 2", Experimental Cell Research, vol. 300, pp. 223-233, (2004).
Lakka, S.S, et al, "Adenovirus-mediated antisense urokinase-type plasminogen activator receptor gene transfer reduces tumor cell

(56) References Cited

OTHER PUBLICATIONS invasion and metastasis in non-small cell lung cancer cell lines", Clinical Cancer Research, vol. 7, No. 4, pp. 1087-1093, (2001).
Langer, P.R, et al, "Enzymatic synthesis of biotin-labeled polynucleotides: novel nucleic acid affinity probes", Proc Natl Acad Sci USA, vol. 78, pp. 6633-6637, (1981).
Larrucea, S, et. al, "Internalization of factor J and cellular signalization after factor J-cell interaction", Biochem Biophys Res Commun, vol. 266, No. 1, pp. 51-57, (1999).
Larrucea, S, et al, "Cellular adhesion mediated by factor J, a complement inhibitor. Evidence for nucleolin involvement", J Biol Chem, vol. 273, No. 48, pp. 31718-31725, (1998).
Lau, Q.C, et al, "In vivo pro-apoptotic and antitumor efficacy of a c-Raf antisense phosphorothioate oligonucleotide: relationship to tumor size", Antisense Nucleic Acid Drug Development, vol. 12, No. 1, pp. 11-20, (2002).
Lebedeva, I, et al, "Antisense oligonucleotides: promise and reality", Annu Rev Pharmacol Toxicol, vol. 41, pp. 403-419, (2001).
Leitinger, N, et al, "ADP-ribosylation of nucleolar proteins in HeLa tumor cells" J Cell Biochem, vol. 52, No. 2, pp. 153-158, (1993).
Lichtenstein, A.V, et al, "Circulating nucleic acids and apoptosis", Annuals New York Academy of Sciences, vol. 945, pp. 239-249, (2001).
Lin, D.L, et al, "p53 is a mediator for radiation-repressed human TR2 orphan receptor expression in MCF-7 cells, a new pathway from tumor suppressor to member of the steroid receptor superfamily", J Biol Chem, vol. 271, pp. 14649-14652, (1996).
Lin, S, et al, "The biochemical status of the DNA synthesome can distinguish between permanent and temporary cell growth arrest", Cell Growth Differ, vol. 8, No. 12, pp. 1359-1369, (1997).
Little, C.D, et al, "Amplification and expression of the c-myc oncogene in human lung cancer cell lines", Nature, vol. 306, pp. 194-196, (1983).
Liu, H, et al, "Construction of a GAL1-regulated yeast cDNA expression library and its application to the identification of genes whose overexpression causes lethality in yeast", Genetics, vol. 132, No. 3, pp. 665-673, (1992).
Lopes de Menezes, D, et al, "Pharmacokinetics of Bcl-2 antisense oligonucleotide (G3139) combined with doxorubicin in SCID mice bearing human breast cancer solid tumor xenografts", Cancer Chemother Pharmacol, vol. 49, No. 1, pp. 57-68, (2002).
Lovborg, H, et al, "Modulation of pyridyl cyanoguanidine (CHS 828) induced cytotoxicity by 3-aminobenzamide in U-937 GTB cells", Biochem Pharmacol, vol. 63, No. 8, pp. 1491-1498, (2002).
Ma J, et al, "Cells designed to deliver anticancer drugs by apoptosis", Cancer Research, vol. 62, No. 5, pp. 1382-1387, (2002).
Mann, M, et al, "Analysis of proteins and proteomes by mass spectrometry", Annu Rev Biochem, vol. 70, pp. 437-473, (2001).
Martelli, A.M, et al, "Biochemical and Morphological characterization of the nuclear matrix from apoptotic HL-60 Cells", Journal of Cellular Biochemistry, vol. 72, No. 1, pp. 35-46, (1999).
Martelli, A.M, et al, "Behavior of nucleolar proteins during the course of apoptosis in camptothecin-treated HL60 cells", Journal of Cellular Biochemistry, vol. 78, No. 2, pp. 264-277, (2000).
Martelli, A.M, et al, "Nuclear apoptotic changes: an overview", J Cell Biochem, vol. 82, No. 4, pp. 634-646, (2001).
Martin, S.J, et al, "Protease activation during apoptosis: death by a thousand cuts?" Cell, vol. 82, pp. 349-352, (1995).
Matthews, D.A, "Adenovirus protein V induces redistribution of nucleolin and B23 from nucleolus to cytoplasm", J Virol, vol. 75, No. 2, pp. 1031-1038, (2001).
Mattson, M.P, "Apoptosis in neurodegenerative disorders", Nature Reviews Mol Cell Biology, vol. 1, No. 2, pp. 120-129, (2000).
Mayer, T.U, et al, "Small molecule inhibitor of mitotic spindle bipolarity identified in a phenotype-based screen", Science, vol. 286, No. 5441, pp. 971-974, (1999).
McEwen, C.N, et al, "Negative gold ion gun for liquid secondary ion mass spectrometry", Anal Chem, vol. 57, No. 4, pp. 890-892, (1985).

McManus, M.T, et al, "Gene silencing in mammals by small interfering RNAs." Nat Rev Genet, vol. 3, No. 10, pp. 737-747, (2002).
McManus, M.T, et al, "Gene silencing using micro-RNA designed hairpins", RNA, vol. 8, No. 6, pp. 842-850, (2002).
McNicol, A.M, et al, "Optimizing immunohistochemistry: antigen retrieval and signal amplification", Histopathology, vol. 32, pp. 97-103, (1998).
Mehes, G, et al, "Nucleolin and fibrillarin expression in stimulated lymphocytes arid differentiating HL-60 cells. A flow cytometric assay", Cell Prolif, vol. 28, No. 6, pp. 329-336, (1995).
Mi, Y, et al, "Validation of Nucleolin as a Novel Target for Cancer Drug Discovery", Proceedings of the American Association for Cancer Research Annual Meeting, vol. 43, Mar. 2002, pp. 959-960, $93^{rd}$ Annual Meeting of the American Association for Cancer Research, San Francisco, California, USA, Apr. 6-10, 2002.
Mickey, D.D, et al, "Heterotransplantation of a human prostatic adenocarcinoma cell line in nude mice", Cancer Research, vol. 37, pp. 4049-4058, (1977).
Mikolajczyk, S, et al, "Tumor-associated forms of prostate specific antigen improve the discrimination of prostate cancer from benign disease", Rinsho Byori, vol. 52, No. 3, pp. 223-230, (2004).
Minota, S, et al, "Autoantibodies to nucleolin in systemic lupus erythematosus arid other diseases", J lmmunol, vol. 146, No. 7, pp. 2249-2252, (1991).
Miranda, G.A, et al, "The murine nucleolin protein is an inducible DNA and ATP binding protein which is readily detected in nuclear extracts of lipopolysaccharide-treated splenocytes", Exp Cell Research, vol. 217, No. 2, pp. 294-308, (1995).
Morgan, D.M, "Tetrazolium (MTT) assay for cellular viability and activity", Meth Mol Biol, vol. 79, pp. 179-183, (1998).
Morimoto, Y, et al, "Alteration of argyrophilic nucleolar organizer region associated (Ag-NOR) proteins in apoptosis-induced human salivary gland cells and human oral aquamous carcinoma cells", J Oral Pathol Med, vol. 30, No. 4, pp. 193-199, (2001).
Morimoto, Y, et al, "Upregulation of the expression of Fas antigen and Fas ligand in a Human submandibular gland ductal cell line by okadaic acid", Arch Oral Biol, vol. 45, No. 8, pp. 657-666, (2000).
Morrison, S.L. et al, "Chimeric human antibody molecules: mouse antigen-binding domains with human constant region domains", Proceedings of the National Academy of Science USA, vol. 81, No. 21, pp. 6851-6855, (1984).
Murchie, A.I, et al, "Retinoblastoma susceptibility genes contain 5' sequences with a high propensity to form guanine-tetrad structures", Nucleic Acids Research, vol. 20, No. 1, pp. 49-53, (1992).
Naito, M, et al, "ATP/$Mg^{2+}$-dependent binding of vincristine to the plasma membrane of multifrug-resistant K562 cells", J Biol Chem, vol. 263, pp. 11887-11891, (1988).
Nakanishi, K, et al, "Argyrophilic nucleolar-organizer region counts and DNA status in bronchioloalveolar epithelial hyperplasia and adenocarcinoma of the lung", Hum Pathol, vol. 29, No. 3, pp. 235-239, (1998).
Navenot, J.M, et al, "Molecular anatomy of CCR5 engagement by physiologic and viral chemokines and HIV-1 envelope glycoproteins: differences in primary structural requirements for RANTES, MIP-1 alpha, and vMIP-II Binding", J Mol Biol, vol. 313, No. 5, pp. 1181-1193, (2001).
Neuberger, M.S, et al, "Recombinant antibodies possessing novel effector functions", Nature, vol. 312, No. 5995, pp. 604-608, (1984).
Nichols, R.C, et al, "The RGG domain in hnRNP A2 affects subcellular localization", Exp Cell Research, vol. 256, No. 2, pp. 522-532, (2000).
Nonomura, A, et al, "Demonstration of nucleolar organizer regions in lung carcinoma by silver staining", Surgery Today, vol. 23, pp. 486-490, (1993).
Norgaard, J.M, et al, "FAB M4 and high CD14 surface expression is associated with high cellular resistance to Ara-C and daunorubicin: implications for clinical outcome in acute myeloid leukaemia", European Journal of Haematology, vol. 67, pp. 221-229, (2001).
Nosseri, C, et al, "Possible involvement of poly(ADP-ribosyl) polymerase in triggering stress-induced apoptosis", Exp Cell Research, vol. 212, No. 2, pp. 367-373, (1994).

(56) References Cited

OTHER PUBLICATIONS

Ohkoudo, M, et al, "Morphometrical analysis of nucleolin immunohistochemistry in meningiomas", Acta Neuropathol, vol. 92, pp. 1-7, (1996).
Orfao, A, et al, "General concepts about cell sorting techniques", Clin Biochem, vol. 29, pp. 5-9, (1996).
Oyama, T, et al, "Nucleolar organizer regions are independently associated with a shortened survival in patients with non-small cell lung cancer", Surg Oncol, vol. 2, No. 6, pp. 341-347, (1993).
Paddison, P.J, et al, "Short hairpin RNAs (shRNAs) induce sequence-specific silencing in mammalian cells", Genes Dev, vol. 16, No. 8, pp. 948-958, (2002).
Paddison, P.J, et al, "Stable suppression of gene expression by RNAi in mammalian cells", Proc Natl Acad Science USA, vol. 99, No. 3, pp. 1443-1448, (2002).
Palomba, L, et al, "Apoptosis and necrosis following exposure of U937 cells to increasing concentrations of hydrogen peroxide: the effect of the poly(ADP-ribose) polymerase inhibitor 3-aminobenzamide", Biochem Pharmacol, vol. 58, No. 11, pp. 1743-1750, (1999).
Pandey, A, et al, "Proteomics to study genes and genomes", Nature, vol. 405, No. 6788, pp. 837-846, (2000).
Partridge, M. et al., "A simple method for delivering morpholino antisense oligos into the cytoplasm of cells", Antisense Nucleic Acid Drug Development, vol. 6, No. 3, pp. 169-175, (1996).
Pasternack, M.S, et al, "Granzyme A binding to target cell proteins Granzyme a binds to and cleaves nucleolin in vitro", J Biol Chem, vol. 266, No. 22, pp. 14703-14708, (1991).
Perry, S.W, et al, "Simultaneous in situ detection of apoptosis and necrosis in monolayer cultures by TUNEL and trypan blue staining", Biotechniques, vol. 22, No. 6, pp. 1102-1106, (1997).
Pich, A, et al, "Prognostic relevance of AgNORs in tumor pathology", Micron, vol. 31, No. 2, pp. 133-141, (2000).
Pinton, P, et al, "The $Ca^+$ concentration of the endoplasmic reticulum is a key determinant of ceramide-induced apoptosis: significance for the molecular mechanism of Bcl-2 action", EMBO J, vol. 20, pp. 2690-2701, (2001).
Platt, N, et al, "Recognizing death: the phagocytosis of apoptotic cells", Trends Cell Biology, vol. 8, No. 9, pp. 365-372, (1998).
Pleschke, J.M, et al, "Poly(ADP-ribose) binds to specific domains in DNA damage checkpoint proteins", J Biol Chem, vol. 275, No. 52, pp. 40974-40980, (2000).
Product Data Sheet for ab7898 from http://www.abcam.com/?datasheet=7898, (1998-2006).
Product Data Sheet for C23 (C-18): sc-9892, Santa Cruz Biotechnology, Inc, (2003).
Product Data Sheet for C23 (MS-3): sc-8031, Santa Cruz Biotechnology, Inc, (2004).
Product Data Sheet for C23 (F-18): sc-9893, Santa Cruz Biotechnology, Inc, (2003).
Product Data Sheet for p7-1A4, from http://dshb.biology.uiowa.edu/objects/catalog//product/extras/4217_p7-1A4.pdf, Antibody Database Information, printed on Aug. 10, 2007.
Product Data Sheet for B23 (C-19): sc-6013, Santa Cruz Biotechnology, Inc., located at http://datasheets.scbt.com/sc-6013.pdf, printed on Aug. 10, 2007.
Product Data Sheet for B23 (H-106): sc-5564, Santa Cruz Biotechnology, Inc., located at http://datasheets.scbt.com/sc-5564.pdf, printed on Aug. 10, 2007.
Product Data Sheet for Monoclonal Antibody, Anti-Nucleolin M019-3, Medical & Biological Laboratories Co, LTD, www.mblintl.com, (2003).
Product Data Sheet for Anti-Nucleolin, Clone 3G4B2, Upstate Biotechnology, http://www.upstate.com/browse/productdetail.asp?ProductId=05-565, (2005).
Puttaraju, M, et al, "Messenger RNA repair and restoration of protein function by spliceosome-mediated RNA trans-splicing", Mol Ther, vol. 4, No. 2, pp. 105-114, (2001).
Raab de Verdugo, U, et al, "Characterization of a 100-kilodalton binding protein for the six serotypes of coxsackie B viruses", Journal of Virology, vol. 69, No. 11, pp. 6751-6757, (1995).
Richardson, D.S, et al, "Effects of PARP inhibition on drug and Fas-induced apoptosis in leukaemic cells", Adv Exp Med Biol, vol. 457, pp. 267-279, (1999).
Robinson, J.M, et al, "Antigen retrieval in cells and tissues: enhancement with sodium dodecyl sulfate", Histochem Cell Biol, vol. 116, pp. 119-130, (2001).
Roninson, I.B, et al, "If not apoptosis, then what? Treatment-induced senescence and mitotic catastrophe in tumor cells", Drug Resist Update, vol. 4, No. 5, pp. 303-313, (2001).
Rosenthal, D.S, et al, "Detection of DNA breaks in apoptotic cells utilizing the DNA binding domain of poly(ADP-ribose) Polymerase with fluorescence microscopy", Nucleic Acids Research, vol. 25, No. 7, pp. 1437-1441, (1997).
Rothenburg, S, et al, "A polymorphic dinucleotide repeat in the rat nucleolin gene forms Z-DNA and inhibits promoter activity", PNAS, vol. 98, No. 16, pp. 8985-8990, (2001).
Roussel, P, et al, "Identification of Ag-NOR proteins, markers of proliferation reated to ribosomal gene activity", Experimental Cell Research, vol. 214, No. 2, pp. 465-472, (1994).
Roussel, P, et al, "Quantification of Ag-NOR proteins using Ag-NOR staining on western blots", Histochem Cytochem, vol. 42, No. 11, pp. 1513-1517, (1994).
Saijo, Y, et al, "Contiguous four-guanosine sequence in c-myc antisense phosphorothioate oligonucleotides inhibits cell growth on human lung cancer cells: possible involvement of cell adhesion inhibition", Jpn J Cancer Research, vol. 88, No. 1, pp. 26-33, (1997).
Saikumar, P, et al, "Apoptosis: definition, mechanisms, and relevance to disease", Am J Med, vol. 107, No. 5, pp. 489-506, (1999).
Sandoval, A, et al, "Distal recognition site for classical pathway convertase located in the C345C/netrin module of complement component C5", J Immunol, vol. 165, No. 2, pp. 1066-1073, (2000).
Schade, R, et al, "Egg yolk antibodies, State of the art and future prospects", Altex 13, supplement 96, pp. 5-9, (1996).
Schade, R, et al, "The production of avian (egg yolk) antibodies IgY. The report and recommendations of ECVAM workshop", Alternatives to laboratory animals (ATLA), vol. 24, pp. 925-934, (1996).
Schimmer, A.D, et al, "Receptor- and mitochondrial-mediated apoptosis in acute leukemia: a translational view", Blood, vol. 98, no. 13, pp. 3541-3553, (2001).
Schmidt-Acevedo, S, et al, "'LE cells' result from phagocytosis of apoptotic bodies induced by antinuclear antibodies", Journal of Autoimmunity, vol. 15, pp. 15-20, (2000).
Schmitt, C.A, et al, "Apoptosis is critical for drug response in vivo", Drug Resist Update, vol. 4, No. 2, pp. 132-134, (2001).
Sciavolino, P.J, et al, "Molecular biology of prostate development and prostate cancer", Ann Med, vol. 30, No. 4, pp. 357-368, (1998).
Scovassi, A.I, et al, "Poly(ADP-ribosylation) and apoptosis", Molecular and Cellular Biochemistry, vol. 199, pp. 125-137, (1999).
Semenkovich, C.F, et al, "A protein partially expressed on the surface of HepG2 cells that binds lipoproteins specifically is nucleolin", Biochemistry, vol. 29, No. 41, pp. 9708-9713, (1990).
Sen, D, et al, "Formation of parallel four-stranded complexes by guanine-rich motifs in DNA and its implications for meiosis", Nature, vol. 334, No. 6180, pp. 364-366, (1988).
Shall, S, et al, "Poly(ASP-ribose) polymerase-1: what have we learned from the deficient mouse model?", Mutat Research, vol. 460, No. 1, oo, 1-15, (2000).
Shall, S, "Poly (ADP-ribosylation)—a common control process?", Bioessays, vol. 24, No. 2, pp. 197-201, (2002).
Sharma, S, et al, "Development of inhalational agents for oncologic use", J Clin Oncol, vol. 19, No. 6, pp. 1839-1847, (2001).
Sharp, P.A, "RNA interference—2001" Genes Dev, vol. 15, No. 5, pp. 485-490, (2001).
Sharp, P.A, et al, "Molecular biology. RNA interference", Science, vol. 287, No. 5462, pp. 2431-2433, (2000).
Shaw, J.P, et al, "Modified deoxyoligonucleotides stable to exonuclease degradation in serum", Nucleic Acids Res, vol. 19, No. 4, pp. 747-750, (1991).

(56) References Cited

OTHER PUBLICATIONS

Sherwood, J.K. et al., "Controlled antibody delivery systems", Biotechnology, vol. 10, No. 11, pp. 1446-1449, (1992).

Shi, S.R, et al, "Antigen retrieval immunohistochemistry: past, present, and future", J Histochem Cytochem, vol. 45, pp. 327-343, (1997).

Shi, S.R, et al, "Antigen retrieval techniques: current perspectives", J Histochem Cytochem, vol. 49, pp. 931-937, (2001).

Shiokawa, D, et al, "Inhibitors of poly(ADP-ribose) polymerase suppress nuclear fragmentation and apoptotic-body formation during apoptosis in HL-60 cells", FEBS Letters, vol. 413, No. 1, pp. 99-103, (1997).

Simbulan-Rosenthal, C.M, et al, "Involvement of Parp and poly(Adp-ribosyl)ation in the early stages of apoptosis and DNA replication", Mol Cell Biochem, vol. 193, No. 1-2, pp. 137-148, (1999).

Sirri, V, et al, "Amount variability of total and individual Ag-NOR proteins in cells stimulated to proliferate", Histochem Cytochem, vol. 43, No. 9, pp. 887-893, (1995).

Skulstad, S, et al, "Labeling of surface proteins of herpes simplex virus type 1 using a modified biotin-streptavidin system", Virus Research, vol. 37, No. 3, pp. 253-270, (1995).

Smulson, M.E, et al, "Roles of poly(ADP-ribosyl)ation and PARP in apoptosis, DNA repair, genomic stability and functions of p53 and E2F-1", Adv Enzyme Regul, vol. 40, pp. 183-215, (2000).

Sohn, J.H, et al, "Caspase-3/CPP32 immunoreactivity and its correlation with frequency of apoptotic bodies in human prostatic carcinomas and benign nodular hyperplasias", Histopathology, vol. 37, No. 6, pp. 555-560, (2000).

Soldani, C. et al., "Poly(ADP-ribose) polymerase cleavage during apoptosis: when and where?", Exp Cell Research, vol. 269, No. 2, pp. 193-201, (2001).

Soldani, C. et al., "Two-color fluorescence detection of Poly (ADP-ribose) polyrnerase-1 (PARP-1) cleavage and DNA strand breaks in etoposide-induced apoptotic cells", Eur J Histochem, vol. 45, No. 4, pp. 389-392, (2001).

Sorokina, E.A, et al, "Cloning and preliminary characterization of a calcium-binding protein closely related to nucleolin on the apical surface of inner medullary collecting duct cells", J Biol Chem, vol. 274, No. 39, pp. 27491-27496, (1999).

Sperandio, S, et al, "An alternative, nonapoptotic form of programmed cell death", Proc Natl Acad Science USA, vol. 97, No. 26, pp. 14376-14381, (2000).

Srinivasan, S.K, et al, "Review of in vivo pharmacokinetics and toxicology of phosphorothioate oligonucleotides", J Clin Lab Anal, vol. 9, No. 2, pp. 129-137, (1995).

Srivastava, M, et al, "Molecular dissection of nucleolin's role in growth and cell proliferation: new insights", FASEB J, vol. 13, No. 14, pp. 1911-1922, (1999).

Stegh, A.H, et al, "DEDD, a novel death effector domain-containing protein, targeted to the nucleolus", EMBO J, vol. 17, No. 20, pp. 5974-5986, (1998).

Stein, C.A, "Is irrelevant cleavage the price of antisense efficacy?", Pharmacol Ther, vol. 85, No. 3, pp. 231-236, (2000).

Stein, C.A. "Keeping the biotechnology of antisense in context", Nat. Biotechnol, vol. 17, No. 3, pp. 209, (1999).

Stein, C.A, et al, "Phosphorothioate oligodeoxynucleotides-antisense inhibitors of gene expression?", Pharmacol Ther, vol. 52, No. 3, pp. 365-384, (1991).

Stone, K.R, et al, "Isolation of a human prostate carcinoma cell line (DU 145)", Int J Cancer, vol. 21, pp. 274-281, (1978).

Stroun, M, et al, "About the possible orgin and mechanism of circulating DNA apoptosis and active DNA release", Clin Chim Acta, vol. 313, No. 1-2, pp. 139-142, (2001).

Stryer, L, "Levels of structure in protein architecture", Biochemistry, Third Edition, chapter 2, pp. 31-33, W.H. Freeman Company, New York, (1988).

Summerton, J, et al, "Morpholino antisense oligomers: design, preparation, and properties", Antisense Nucleic Acid Drug Development, vol. 7, No. 3, pp. 187-195, (1997).

Sundquist, W.I, et al, "Telomeric DNA dimerizes by formation of guanine tetrads between hairpin loops", Nature, vol. 342, No. 6251, pp. 825-829, (1989).

Sundquist, W.I, et al, "Evidence for interstrand quadruplex formation in the dimerization of human immunodeficiency virus 1 genomic RNA", Proc Natl Acad Science USA, vol. 90, No. 8, pp. 3393-3397, (1993).

Sutton, V.R, et al, "Initiation of apoptosis by granzyme B requires direct cleavage of bid, but not direct granzyme B-mediated caspase activation", J Exp Med, vol. 192, No. 10, pp. 1403-1413, (2000).

Symons, R.H. "Small catalytic RNAs", Annual Review Biochem, vol. 61, pp. 641-671, (1992).

Takahashi, T, et al, "p53: a frequent target for genetic abnormalities in lung cancer", Science, vol. 246, pp. 491-494, (1989).

Tanaka, Y, et al, "Inhibition and down-regulation of poly(ADP-ribose) polymerase results in a marked resistance of HL-60 cells to various apoptosis-inducers", Cell Mol Biol, vol. 41, No. 6, pp. 771-781, (1995).

Templin, M.V, et al, "Pharmacokinetic and toxicity profile of a phosphorothioate oligonucleotide following inhalation delivery to lung in mice", Antisense Nucleic Acid Drug Dev, vol. 10, No. 5, pp. 359-368, (2000).

Tentori, L, et al, "Potential clinical applications of poly(ADP-ribose) polymerase (PARP) inhibitors", Pharmacol Res, vol. 45, No. 2, pp. 73-85, (2002).

Thornberry, N.A, et al, "Caspases: enemies within", Science, vol. 281, pp. 1312-1316. (1998).

Tockman, M.S, et al, "Prospective detection of preclinical lung cancer: results from two studies of heterogeneous nuclear ribonucleoprotein A2/B1 overexpression", Clin Cancer Research, vol. 3, No. 12, pt. 1, pp. 2237-2246, (1997).

Tockman, M.S, et al, "Sensitive and specific monoclonal antibody recognition of human lung cancer antigen on preserved sputum cells: a new approach to early lung cancer detection", J Clin Oncol, vol. 6, No. 11, pp. 1685-1693, (1988).

Tormanen, U, et al, "Enhanced apoptosis predicts shortened survival in non-small cell lung carcinoma", Cancer Research, vol. 55, No. 23, pp. 5595-5602, (1995).

Trere, D, "AgNOR staining and quantification", Micron, vol. 31, No. 2, pp. 127-131, (2000).

Tu, G.C, et al, "Tetranucleotide GGGA motif in primary RNA transcripts. Novel target site for antisense design", J Biol Chem, vol. 273, No. 39, pp. 25125-25131, (1998).

Tuteja, N, et al, "Human DNA helicase IV is nucleolin, an RNA helicase modulated by phosphorylation", Gene, vol. 160, No. 2, pp. 143-148, (1995).

Tuteja, R, et al, "Nucleolin: a multifunctional major nucleolar phosphoprotein", Crit Rrev Biochem Mol Biol, vol. 33, pp. 407-436, (1998).

Van de Loosdrecht, A.A, et al, "A tetrazolium-based colorimetric MTT assay to quantitate human monocyte mediated cytotoxicity against leukemic cells from cell lines and patients with acute myeloid leukemia", J Immunol Methods, vol. 174, pp. 311-320, (1994).

Waggoner, S, et al, "Viral ribonucleoprotein complex formation and nucleolar-cytoplasmic relocalization of nucleolin in poliovirus-infected cells", J Virol, vol. 72, No. 8, pp. 6699-6709, (1998).

Wang, W, et al, "A comparison of guanosine-quartet inhibitory effects versus cytidine homopolymer inhibitory effects on rat neointimal formation", Antisense Nucleic Acid Drug Development, vol. 8, No. 3, pp. 227-236, (1998).

Wang, Y, et al, "Regulation of dna replication after heat shock by replication protein a-nucleolin interactions", J Biol Chem, vol. 276, No. 23, pp. 20579-20588, (2001).

Wang, Y, et al, "Solution structure of the human telomeric repeat d[AG3(T2AG3)3] G-tetraplex", Structure, vol. 1, No. 4, pp. 263-282, (1993).

Wang, Z.Q, et al, "PARP is important for genomic stability but dispensable in apoptosis", Genes Dev, vol. 11, No. 18, pp. 2347-2358, (1997).

Weisenberger, D, et al, "A possible mechanism for the inhibition of ribosomal RNA gene transcription furing mitosis", J Cell Biology, vol. 129, No. 3, pp. 561-575, (1995).

(56) References Cited

OTHER PUBLICATIONS

White, J.R, et al, "Phosphorothioate-capped antisense oligonucleotides to Ras GAP injibit cell proliferation and trigger apoptosis but fail to downregulate GAP gene expression", Biochem Biophys Res Commun, vol. 227, No. 1, pp. 118-124, (1996).
Whittles, C.E, et al, "Apoptotic and proliferative activity in the neoplastic progress on of Barrett's oesophagus: a comparative study", The Journal of Pathology, vol. 187, issue 5, pp. 535-540, (1999).
Williamson, J.R, et al, "Monovalent cation-induced structure of telomeric DNA: the G-quartet model", Cell, vol. 59, No. 5, pp. 871-880, (1989).
Winter, G, et al, "Making antibodies by phage display technology", Annu Rev Immunol, vol. 12, pp. 433-455, (1994).
Wolters, D.A, et al, "An automated multidimensional protein identification technology for shotfun proteomics", Anal Chem, vol. 73, No. 23, pp. 5683-5690, (2001).
Wurzer, G, et al., "Increased resistance to anticancer therapy of mouse cells lacking the poly(ADP-ribose) polymerase attributable to up-regulation of the multidrug resistance gene product P-glycoprotein", Cancer Research, vol. 60, No. 15, pp. 4238-4244, (2000).
Wyatt, J.R, et al, "Combinatorially selected guanosine-quartet structure is a potent inhibitor of human immunodeficiency virus envelope-mediated cell fusion", Proc Natl Acad Science USA, vol. 91, No. 4, pp. 1356-1360, (1994).
Wyllie, A.H, et al, "Cell death: the significance of apoptosis", International Review of Cytology, vol. 68, pp. 251-306, (1980).
Wysocki, L.J, et al, ""Panning" for lymphocytes: a method for cell selection", Proc Natl Acad Sci USA, vol. 75, No. 6, pp. 2844-2848, (1978).
Xu, X, et al, "Inhibition of DNA replication and induction of S phase cell cycle arrest by G-rich oligonucleotides", The Journal of Biological Chemistry, vol. 276, No. 46, pp. 43221-43230, (2001).
Xue, Z, et al, "The amino terminus of mammalian nucleolin specifically recognizes SV40 T-antigen type nuclear localization sequences", Eur J Cell Biol, vol. 62, No. 1, pp. 13-21, (1993).
Yanagida, M, et al, "Isolation and proteomic characterization of the major proteins of the nucleolin-binding ribonucleoprotein complexes", Proteomics, vol. 1, No. 11, pp. 1390-1404, (2001).
Yao, G.Q, et al, "Identification of two oligodeoxyribonucleotide binding proteins on plasma membranes of human cell lines", Biochemical Pharmacology, vol. 51, pp. 431-436, (1996).
Xiao-Ming, Y., "Signal transduction mediated by Bid, a pro-death Bcl-2 family proteins, connects the death receptor and mitochondria apoptosis pathways", Cell Research, vol. 10, No. 3, pp. 161-167, (2000).
European Search Report dated Oct. 25, 2006 for European application No. 03762073.9.
Mi, Y., et al., "Apoptosis in Leukemia cells is accompanied by alterations in the levels and localization of Nucleolin", The Journal of Biological Chemistry, vol. 278, No. 10, pp. 8572-8579, (2003).
Rosen, A., et al., "Autoantigens as substrates for apoptotic proteases: implications for the pathogenesis of systemic autoimmune disease", Cell Death and Differentiation, vol. 6, No. 1, pp. 6-12, (1999).
Masters, J.R.W., "Human cancer cell lines: fact and fantasy", Nature Reviews Molecular Cell Biology, vol. 1, pp. 233-236, (2000).
Gougeon, M-L. et al., "Programmed cell death in peripheral lymphocytes from HIV-Infected persons", The Journal of Immunology, vol. 156, pp. 3509-3520, (1996).
Mi, Y. et al., "Regulation of Nucleolin in U937 Cells Treated with UV-Light and Cytotoxic Drugs", Blood, vol. 98, No. 11, Part 2 of 2, Abstract No. 4223, (2001).
Destouches, D. et al., "Suppression of tumor growth and angiogenesis by a specific antagonist of the cell-surface expressed nucleolin", Plos One, vol. 3, issue 6, e2518, pp. 1-12, (2008).
Fogal, V. et al., "Cell surface nucleolin antagonist causes endothelial cell apoptosis and normalization of tumor vasculature", Angiogenesis, vol. 12, No. 1, pp. 91-100, (2009).
Ugrinova I. et al., "Inactivation of nucleolin leads to nucleolar disruption, cell cycle arrest and defects in centrosome duplication", BMC Molecular Biology, pp. 1-16, (2007).
Cylene Pharmaceuticals, Quarfloxin Nucleolus Targeting Agent (CX-3543), Quarfloxin QPLX/Nucleolin Inhibitor (CX-3543), 1 page, printed on Jan. 21, 2010.
ImmuPharma, Treatment for Cancer (IPP-204106), pp. 1-3, found at http://immupharma.com/cancer.html, printed on Jan. 21, 2010.
Invitation to Pay Additional Fees and International Fees and Partial Search Report dated Jul. 14, 2009 for PCT/US2008/088491.
Grinstein, E. et al., "Cellular signaling in normal and cancerous stem cells", Cellular Signaling, 19, pp. 2428-2433, (2007).
Grinstein, E. et al., "Nucleolin Regulates Gene Expression in CD34-positive Hematopoietic Cells", The Journal of Biological Chemistry, vol. 282, No. 17, pp. 12439-12449, (2007).
Soltysova, A. et al., "Cancer Stem Cells", Neoplasma, 52, 6, pp. 435-440, (2005).
Huang, E.H. et al., "Cancer stem cells: A new paradigm for understanding tumor progression and therapeutic resistance", Surgery, vol. 141, pp. 415-419, (2007).
Girvan, A.C. et al., "AGRO100 inhibits activation of nuclear factor-κb (NF-κb) by forming a complex with NF-κb essential modulator (NEMO) and nucleolin", Molecular Cancer Therapeutics, vol. 5, No. 7, pp. 1790-1799, (2006).
Christian, S. et al., "Nucleolin expressed at the cell surface is a marker of endothelial cells in angiogenic blood vessels", The Journal of Cell Biology, vol. 163, No. 4, pp. 871-878, (2003).
Clarke, M.F. et al., "Stem Cells: The Real Culprits in Cancer?", Scientific American, 295, 1, pp. 52-59, (2006).
Shah, K. et al., "AS1411, a novel DNA aptamer as a potential treatment of acute myelogenous leukaemia (AML)", Meeting Poster, 48th Annual Meeting of the American Society of Hematology, Orlando, FL, USA. Dec. 9-12, 2006.
Guo, K-T. et al., "A new technique for the isolation and surface immobilization of mesenchymal stem cells from whole bone marrow using high-specific DNA aptamers", Stem Cells, vol. 24, pp. 2220-2231, (2006).
Rubanyi, G.M., "The future of human gene therapy", Molecular Aspects of Medicine, vol. 22, pp. 113-142, (2001).
Verma, I.M. et al., "Gene therapy—promises, problems and prospects", Nature, vol. 389, pp. 239-242, (1997).
Friedmann, T. "Overcoming the obstacles to gene therapy", Scientific American, pp. 96-101, (1997).
Orkin, S.H. et al., "Report and recommendations of the panel to assess the NIH investment in research on gene therapy", NIH ad hoc committee, pp. 1-39, found at http://oba.od.nih.gov/oba/rac/panelrep.pdf, (1995).
Gura, T. "Systems for identifying new drugs are often faulty", Science, vol. 278, pp. 1041-1042, (1997).
Beckman, R.A. et al., "Antibody constructs in cancer therapy", Cancer, vol. 109, No. 2, pp. 170-179, (2007).
Kito, S. et al., "Cleavage of nucleolin and AgNOR proteins during apoptosis induced by anticancer drugs in human salivary gland cells", Journal of Oral Pathology & Medicine, vol. 34, pp. 478-485, (2005).
National Cancer Institute, Fact Sheet, "Targeted Cancer Therapies", U.S. Department of Health and Human Services, pp. 1-8, May 9, 2012.
Zhang, Y. et al., "A surface-charge study on cellular-uptake behavior of F3-peptide-conjugated iron oxide nanoparticles", Small, vol. 5, No. 17, pp. 1990-1996, (2009).
Orringer, D.A. et al., "In vitro characterization of a targeted, dye-loaded nanodevice for intraoperative tumor delineation", Neurosurgery, vol. 64, No. 5, pp. 965-972, (2009).
Cao, Z. et al., "Reversible cell-specific drug delivery with aptamer-functionalized liposomes", Angewaudte Chemie International Edition, vol. 48, issue 35, pp. 6494-6498, (2009).
Shieh, Y-A. et al., "Aptamer-based tumor-targeted drug delivery for photodynamic therapy", ACS Nano, vol. 4, No. 3, pp. 1433-1442, (2010).

(56) References Cited

OTHER PUBLICATIONS

Aravind, A. et al., "AS1411 aptamer tagged PLGA-lecithin-PEG nanoparticles for tumor cell targeting and drug delivery", Biotechnology and Bioengineering, vol. 109, No. 11, pp. 2920-2931, (2012).
Xie, L., et al., "Bovine serum albumin nanoparticles modified with multilayers and aptamers for pH-responsive and targeted anticancer drug delivery", Journal of Materials Chemistry, vol. 22, pp. 6053-6060, (2012).
Kang, W.J. et al., "Multiplex imaging of single tumor cells using quantum-dot-conjugated aptamers", Small, vol. 5, No. 22, pp. 2519-2522, (2009).
Ko, M.H. et al., "In vitro derby imaging of cancer biomarkers using quantum dots", Small, vol. 5, No. 10, pp. 1207-1212, (2009).
Choi, J.H. et al., "DNA aptamer-passivated nanocrystals synthesis: A facile approach for nanoparticles-based cancer cell growth inhibition", Small, vol. 5, No. 6, pp. 672-675, (2009).
Ai, J. et al., "DNA G-quadruplex-templated formation of the fluorescent silver nanocluster and its application to bioimaging", Talanta, vol. 88, pp. 450-455, (2012).
Kim, J.K. et al., "Molecular imaging of a cancer-targeting theragnostics probe using a nucleolin aptamer- and microRNA-221 molecular beacon-conjugated nanoparticle", Biomaterials, vol. 33, pp. 207-217, (2012).
Hwang, D.W. et al., "A nucleolin-targeted multimodal nanoparticle imaging probe for tracking cancer cells using an aptamer", Journal of Nuclear Medicine, vol. 51, No. 1, pp. 98-105, (2010).
Takafuji, Y. et al., "Simple PEG modification of DNA aptamer based on copper ion coordination for tumor targeting", Journal of Biomaterials Science, vol. 22, pp. 1179-1195, (2011).
Jain, K.K. "Advances in the field of nanooncology", BMC Medicine, vol. 8, No. 83, pp. 1-11, (2010).
Portney, N.G. et al., "Nano-oncology: drug delivery, imaging, and sensing", Analytical and Bioanalytical Chemistry, vol. 384, No. 3, pp. 620-630, (2006).
Bates, P.J. et al., "G-rich oligonucleotides for cancer treatment", Methods in Molecular Biology, vol. 542, pp. 379-392, (2009).
Bates, P.J. et al., "Discovery and development of the G-rich oligonucleotide AS1411 as a novel treatment for cancer", Experimental and Molecular Pathology, vol. 86, No. 3, pp. 151-164, (2009).
Soundararajan, S. et al., "The nucleolin targeting aptamer AS1411 destabilizes Bcl-2 messenger RNA in human breast cancer cells", Cancer Research, vol. 68, No. 7, pp. 2358-2365, (2008).
Javier, D.J. et al., "Aptamer-targeted gold nanoparticles as molecular-specific contrast agents for reflectance imaging", Bioconjugate Chemistry, vol. 19, No. 6, pp. 1309-1312, (2008).
Euhus, D.M. et al., "Tumor measurement in the nude mouse", Journal of Surgical Oncology, vol. 31, issue 4, pp. 229-234, (1986).
Tomayko, M.M. et al., "Determination of subcutaneous tumor size in athymic (nude) mice", Cancer Chemotherapy and Pharmacology, vol. 24, issue 3, pp. 148-154, (1989).
Mosmann, T. "Rapid colorimetric assay for cellular growth and survival: application to proliferation and cytotoxicity assays", Journal of Immunological Methods, vol. 65, issue 1-2, pp. 55-63, (1983).
Vermes, I. et al., "A novel assay for apoptosis. Flow cytometric detection of phosphatidylserine expression on early apoptotic cells using fluorescein labeled Annexin V", Journal of Immunological Methods, vol. 184, No. 1, pp. 39-51, (1995).
Reyes-Reyes, E.M. et al., "A new paradigm for aptamer therapeutic AS1411 action: uptake by macropinocytosis and its stimulation by a nucleolin-dependent mechanism", Cancer Research, vol. 70, No. 21, pp. 8617-8629, (2010).
Sprague, J.E. et al., "Noninvasive imaging of osteoclasts in parathyroid hormone-induced osteolysis using a 64Cu-labeled RGD peptide", Journal of Nuclear Medicine, Society of Nuclear Medicine, vol. 48, No. 2, pp. 311-318, (2007).
Thayer, A.M. "Fabulous fluorine", Chemical and Engineering News, vol. 84, No. 23, pp. 15-24, (2006).
Shoemaker, R.H. "The NCI60 human tumour cell line anticancer drug screen", Nature Reviews Cancer, vol. 6, No. 10, pp. 813-823, (2006).
Andrianasolo, E.H. et al., "DNA methyl transferase inhibiting halogenated monoterpenes from the Madagascar red marine alga Portieria hornemannii", Journal of Natural Products, vol. 69, No. 4, pp. 576-579, (2006).
Egorin, M.J. et al., "In vitro metabolism by mouse and human liver preparations of halomon, an antitumor halogenated monoterpene", Cancer Chemother Pharmacol, vol. 41, No. 1, pp. 9-14, (1997).
Egorin, M.J. et al., "Plasma pharmacokinetics, bioavailability, and tissue distribution in CD2F1 mice of halomon, an antitumor halogenated monoterpene isolated from the red algae Portieria hornemannii", Cancer Chemother Pharmacol, vol. 39, No. 1-2, pp. 51-60, (1996).
Fuller, R.W. et al., "Isolation and structure/activity features of halomon-related antitumor monoterpenes from the red alga Portieria hornemannii", Journal of Medicinal Chemistry, vol. 37, No. 25, pp. 4407-4411, (1994).
Fuller, R.W. et al., "A pentahalogenated monoterpene from the red alga *Portieria hornemannii* produces a novel cytotoxicity profile against a diverse panel of human tumor cell lines", Journal of Medicinal Chemistry, vol. 35, No. 16, pp. 3007-3011, (1992).
Thomsen, M.K. et al., "SOX9 elevation in the prostate promotes proliferation and cooperates with PTEN loss to drive tumor formation", Cancer Research, vol. 70, No. 3, pp. 979-987, (2010).
Wang, H. et al., "SOX9 is expressed in human fetal prostate epithelium and enhances prostate cancer invasion", Cancer Research, vol. 68, No. 6, pp. 1625-1630, (2008).
Thomsen, M.K. et al., "Sox9 is required for prostate development", Developmental Biology, vol. 316, No. 2, pp. 302-311, (2008).
Acevedo, V.D. et al., "Inducible FGFR-1 activation leads to irreversible prostate adenocarcinoma and an epithelial-to-mesenchymal transition", Cancer Cell, vol. 12, No. 6, pp. 559-571, (2007).
Wang, H. et al., "SOX9 is expressed in normal prostate basal cells and regulates androgen receptor expression in prostate cancer cells", Cancer Research, vol. 67, No. 2, pp. 528-536, (2007).
Baniwal, S.K. et al., "Runx2 transcriptome of prostate cancer cells: insights into invasiveness and bone metastasis", Molecular Cancer, vol. 9, pp. 1-18, (2010).
Qi, J. et al., "Siah2-dependent concerted activity of HIF and FoxA2 regulates formation of neuroendocrine phenotype and neuroendocrine prostate tumors", Cancer Cell, vol. 18, No. 1, pp. 23-38, (2010).
Schaeffer, E.M. et al., "Androgen-induced programs for prostate epithelial growth and invasion arise in embryogenesis and are reactivated in cancer", Oncogene, vol. 27, No. 57, pp. 7180-7191, (2008).
Dudley, A.C. et al., "Calcification of multi-potent, prostate tumor endothelium", Cancer Cell, vol. 14, No. 3, pp. 201-211, (2008).
Thomsen, M.K. et al., "The role of Sox9 in prostate development", Differentiation, vol. 76, pp. 728-735, (2008).
Walker, I. et al., "Do molecularly targeted agents in oncology have reduced attrition rates?", Nature Reviews, Drug Discovery, vol. 8, pp. 15-16, (2009).
Workman, P. et al., "Minimally invasive pharmacokinetic and pharmacodynamic technologies in hypothesis-testing clinical trials of innovative therapies", Journal of the National Cancer Institute, vol. 98, No. 9, pp. 580-598, (2006).
Khleif, S.N. et al., "AACR-FDA-NCI Cancer Biomarkers Collaborative consensus report: advancing the use of biomarkers in cancer drug development", Clinical Cancer Research, vol. 16, pp. 3299-3318, (2010).
Linardou, H. et al., "Assessment of somatic k-RAS mutations as a mechanism associated with resistance to EGFR-targeted agents: a systematic review and meta-analysis of studies in advanced non-small-cell lung cancer and metastatic colorectal cancer", Lancet Oncology, vol. 9, No. 10, pp. 962-972, (2008).
Annunziata, C.M. et al., "PARP inhibitors in BRCA1 /BRCA2 germline mutation carriers with ovarian and breast cancer", F1000 Biology Reports, vol. 2, No. 10, pp. 1-4, (2010).
American Cancer Society, "Cancer Facts and Figures 2010" found at www.cancer.org/research/cancerfactsfigures/cancerfactsfigures/cancer-facts-and-figures-2010, pp. 1-62, (2010).

(56) References Cited

OTHER PUBLICATIONS

Bonkhoff, H. et al., "From pathogenesis to prevention of castration resistant prostate cancer", The Prostate, vol. 70, No. 1, pp. 100-112, (2010).
Huch, M. et al., "Sox9 marks adult organ progenitors", Nature Genetics, vol. 43, No. 1, pp. 9-10, (2011).
Scott, C.E. et al., "SOX9 induces and maintains neural stem cells", Nature Neuroscience, vol. 13, No. 10, pp. 1181-1189, (2010).
Mori-Akiyama, Y. et al., "SOX9 is required for the differentiation of paneth cells in the intestinal epithelium", Gastroenterology, vol. 133, No. 2, pp. 539-546, (2007).
Malki, S. et al., "Expression and biological role of the prostaglandin D synthase/SOX9 pathway in human ovarian cancer cells", Cancer Letters, vol. 255, No. 2, pp. 182-193, (2007).
Jiang, S.S. et al., "Upregulation of SOX9 in Lung Adenocarcinoma and Its Involvement in the Regulation of Cell Growth and Tumorigenicity", Clinical Cancer Research, vol. 16, pp. 4363-4373, (2010).
Cajaiba, M.M. et al., "Sox9 expression is not limited to chondroid neoplasms: variable occurrence in other soft tissue and bone tumors with frequent expression by synovial sarcomas", International Journal of Surgical Pathology, vol. 18, No. 5, pp. 319-323, (2010).
Stange, D.E. et al., "Expression of an ASCL2 related stem cell signature and IGF2 in colorectal cancer liver metastases with 11p15.5 gain", Gut, vol. 59, pp. 1236-1244, (2010).
Muller, P. et al., "SOX9 mediates the retinoic acid-induced HES-1 gene expression in human breast cancer cells", Breast Cancer Research Treatment, vol. 120, No. 2, pp. 317-326, (2010).
Passeron, T. et al., "Upregulation of SOX9 inhibits the growth of human and mouse melanomas and restores their sensitivity to retinoic acid", The Journal of Clinical Investigation, vol. 119, No. 4, pp. 954-963, (2009).
Yasui, W. et al., "Transcriptome dissection of gastric cancer: Identification of novel diagnostic and therapeutic targets from pathology specimens", Pathology International, vol. 59, pp. 121-136, (2009).
Lu, B. et al., "Analysis of SOX9 expression in colorectal cancer", American Journal of Clinical Pathology, vol. 130, No. 6, pp. 897-904, (2008).
Endo, Y. et al., "Role of Sox-9, ER81 and VE-cadherin in retinoic acid-mediated trans-differentiation of breast cancer cells", PLoS One, vol. 3, issue 7, pp. 1-11, (2008).
De Bont, J.M. et al., "Differential expression and prognostic significance of SOX genes in pediatric medulloblastoma and ependymoma identified by microarray analysis", Neuro-Oncology, vol. 10, No. 5, pp. 648-660, (2008).
Vidal, V.P.I. et al., "SOX9 expression is a general marker of basal cell carcinoma and adnexal-related neoplasms", Journal of Cutaneous Pathology, vol. 35, pp. 373-379, (2008).
Passeron, T. et al., "SOX9 is a key player in ultraviolet B-induced melanocyte differentiation and pigmentation", Proceedings of the National Academy of Sciences, vol. 104, No. 35, pp. 13984-13989, (2007).
Duhagon, M.A. et al., "Genomic profiling of tumor initiating prostatospheres", BMC Genomics, vol. 11, No. 324, pp. 1-16, (2010).
Yilmaz, O.H. et al., "Pten dependence distinguishes haematopoietic stem cells from leukaemia-initiating cells", Nature, vol. 441, pp. 475-482, (2006).
Yoo, C.B. et al., "Epigenetic therapy of cancer: past, present and future", Nature Reviews Drug Discovery, vol. 5, No. 1, pp. 37-50, (2006).
McCabe, M.T. et al., "Cancer DNA methylation: molecular mechanisms and clinical implications", Clinical Cancer Research, vol. 15, No. 12, pp. 3927-3937, (2009).
Piekarz, R.L. et al., "Epigenetic modifiers: basic understanding and clinical development", Clinical Cancer Research, vol. 15, No. 12, pp. 3918-3926, (2009).
Issa, J-P.J. et al., "Targeting DNA methylation", Clinical Cancer Research, vol. 15, No. 12, pp. 3938-3946, (2009).
Xu, B. et al., "An efficient synthesis of difluoropropargyl bromides", Synthesis, vol. 5, pp. 803-806, (2006).

Sigalotti, L. et al., "Epigenetic modulation of solid tumors as a novel approach for cancer immunotherapy", Seminars in Oncology, vol. 32, No. 5, pp. 473-478, (2005).
Budman, D.R. et al., "Identification of potentially useful combinations of epidermal growth factor receptor tyrosine kinase antagonists with conventional cytotoxic agents using median effect analysis", Anti-cancer Drugs, vol. 17, No. 8, pp. 921-928, (2006).
Yang, X. et al., "Near-infrared light-triggered, targeted drug delivery to cancer cells by aptamer gated nanovehicles", Advanced Materials, vol. 24, pp. 2890-2895, (2012).
International Search Report dated Sep. 19, 2012 for PCT application No. PCT/US2012/040577.
Akerman, M.E. et al., "Nanocrystal targeting in vivo", Proceedings of the National Academy of Sciences, vol. 99, No. 20, pp. 12617-12621, (2002).
Winer, I. et al., "F3-targeted cisplatin-hydrogel nanoparticles as an effective therapeutic that targets both murine and human ovarian tumor endothelial cells in vivo", Cancer Research, vol. 70, No. 21, pp. 8674-8683, (2010).
Dam, D.H.M. et al., "Direct observation of nanoparticle-cancer cell nucleus interactions", ACS Nano, vol. 6, No. 4, pp. 3318-3326, (2012).
Bruckner, R.C. et al., "The histone-like H protein of *Escherichia coli* is ribosomal protein S3", Nucleic Acids Research, vol. 17, No. 8, pp. 3145-3161, (1989).
"Nucleolin Antibody—Antibody product information from all suppliers", Labome the World of Laboratories, pp. 1-4, found at www.labome.com/gene/human/nucleolin-antibody.html, printed on Jun. 1, 2012.
Malik, M.T. et al., "Multifunctional gold nanoparticles linked with aptamers and fluorophores for breast cancer imaging and therapy", American Association of Cancer Research Annual Meeting, Mar. 31-Apr. 4, 2012, Chicago, IL Abstract #5688.
Subramanian, D. et al., "Induction of macropinocytosis and cell death in neuroblastoma cells treated with AS1411", Research Louisville 2011, University of Louisville, Louisville, Kentucky, Abstract #GRD-72.
Malik, M.T. et al., "Aptamers conjugated to gold nanoparticles and their potential for breast cancer imaging and therapy", Congressionally Directed Medical Research Programs, Era of Hope 2011, Orlando Florida, Aug. 2-5, 2011, Poster #P43-16.
Srivastava, M. et al., "Genomic organization and chromosomal localization of the human necleolin gene", The Journal of Biological Chemistry, vol. 265, No. 25, pp. 14922-14931, (1995).
Gattoni-Celli, S. et al., "Overexpression of nucleolin in engrafted acute myelogerous leukemia cells", American Journal of Hematology, vol. 84, issue 8, pp. 535-538, (2009).
Green, C. et al., "Anti-tumor efficacy and pharmacokinetics of the novel aptamer AS1411 in a continuous infusion nude rat xenograft model", Proceedings of the 101$^{st}$ Annual Meeting of the American Association for Cancer Research, Abstract No. 2614, Apr. 17-21, 2010.
Fernandes, D.J. et al., "Human anti-nucleolin antibodies with broad spectrum anticanser activity", Proceeding of the 103$^{rd}$ Annual Meeting of the American Association for Cancer Research, Abstract No. 4623, Mar. 31-Apr. 4, 2012.
Laber, D.A. et al., "Extended phase I study of AS1411 in renal and non-small cell lung cancers", Journal of Clinical Oncology, ASCO Annual Meeting Proceedings, vol. 24, No. 18S, Abstract No. 13098, (2006).
Chames, P. et al., "Therapeutic antibodies: successes, limitations and hopes for the future", British Journal of Pharmacology, vol. 157, pp. 220-233, (2009).
Huang, Y. et al., "The angiogenic function of nucleolin is mediated by vascular endothelial growth factor and nonmuscle myosin", Blood, vol. 107, No. 9, pp. 3564-3571, (2006).
Malik, M.T. et al., "Aptamers conjugated to gold nanoparticles and their potential for breast cancer imaging and therapy", Research Louisville 2011, University of Louisville, Louisville, Kentucky (Finalist, Post-Doctoral Category), Abstract # PRF-52.

(56) References Cited

OTHER PUBLICATIONS

Bates, P.J. "DNA Aptamers: Potential application in nanotechnology, drug delivery, therapy, & imaging", Mini-Symposium on Nanobiomotors, University of Kentucky, Abstract, 1 page, Mar. 26, 2012.
Waldmann, T.A., "Immunotherapy: past, present and future", Nature Medicine, vol. 9, No. 3, pp. 269-277, (2003).
Hengge, U.R. et al., "Long-term chemotherapy of HIV-associated Kaposi's sarcoma with liposomal doxorubidn", European Journal of Cancer, vol. 37, pp. 878-883, (2001).
Orlikowsky, T.W. et al., "Dexamethasone inhibits CD4 T cell deletion mediated by macrophages from human immunodeficiency virus-infected persons", Journal of Infectious Diseases, vol. 184, No. 10, pp. 1328-1330, (2001).
European Search Report for Application No. 15182208.7 dated Mar. 2, 2016.
National Lung Screening Trial Research Team, "Reduced lung-cancer mortality with low-dose computed tomographic screening", The New England Journal of Medicine, vol. 365, No. 5, pp. 395-409, (2011).
International Search Report dated Jul. 21, 2016 for PCT application No. PCT/US2016/030985.
Hua, X. et al., "Selective collection and detection of MCF-7 breast cancer cells using aptamer-functionalized magnetic beads and quantum dots based nano-bio-probes", Analytica Chimica Acta, vol. 788, pp. 135-140, (2013).
Definition of "Cyanine" printed from Wikipedia, the free encyclopedia on Jan. 11, 2017 found at http://en.wikipedia.org /wiki/Cyanine.
Bates, P.J. et al., "G-quadruplex oligonucleotide AS1411 as a cancer-targeting agent: Uses and mechanisms", Biochimica et Biophysica Acta, (BBA)—General Subjects, pp. 1-16, (2016).
Wang, C-H. et al., "Aptamer-conjugated and drug-loaded acoustic droplets for ultrasound theranosis", Biomaterials, vol. 33, pp. 1939-1947, (2011).
Liao, Z-X. et al., "An AS1411 aptamer-conjugated liposomal system containing a bubble-generating agent for tumor-specific chemotherapy that overcomes multidrug resistance", Journal of Controlled Release, vol. 208, pp. 42-51, (2015).
Li, L. et al., "Nucleolin-targeting liposomes guided by aptamer AS1411 for the delivery of siRNA for the treatment of malignant melanomas", Biomaterials, vol. 35, pp. 3840-3850, (2014).
Zhang, H. et al., "In vitro characterization and in vivo ultrasound molecular imaging of nucleolin-targeted microbubbles", Biomaterials, vol. 118, pp. 63-73, (2016).
Bates, P.J. et al., "G-quadruplex oligonucleotide AS1411 as a cancer-targeting agent: Uses and mechanisms", Biochimica et Biophysica Acta, vol. 1861, pp. 1414-1428, (2016).
International Search Report dated Oct. 19, 2017 for PCT application No. PCT/US2017/045169.
Cooper, D.R. et al., "Gold nanoparticles and their alternatives for radiation therapy enhancement", Frontiers in Chemistry, vol. 2, Article 86, pp. 1-13, (2014).
Alkilany, A.M. et al., "Toxicity and cellular uptake of gold nanoparticles: what we have learned so far?", Journal of Nanoparticle Research, vol. 12, No. 7, pp. 2313-2333, (2010).
Definition of "CT scan" printed from Wikipedia, the free encyclopedia on Jan. 11, 2017 found at http://en.wikipedia.org/wiki/CT_scan.
Humphrey, L.L. et al., "Screening for Lung Cancer with low-dose computed tomography: A systemic review to update the U.S. Preventive Services Task Force recommendation", Annals of Internal Medicine, vol. 159, No. 6, pp. 411-420, (2013).
Hochhegger, B. et al., "MRI in lung cancer: a pictorial essay", The British Journal of Radiology, vol. 84, No. 1003, pp. 661-668, (2011).
Malik, M.T. et al., "AS1411-conjugated gold nanospheres and their potential for breast cancer therapy", Oncotarget, vol. 6, No. 26, pp. 22270-22281, (2015).
Rosenberg, J.E. et al., "A phase II trial of the nucleolin-targeted DNA aptamer AS1411 in metastatic refractory renal cell carcinoma", Invest New Drugs, vol. 32, No. 1, pp. 178-187, (2014).
Erdogan, S. et al., "Gadolinium-loaded polychelating polymer-containing cancer cell-specific immunoliposomes", Journal of Liposome Research, vol. 16, issue 1, pp. 45-55, (2006) Abstract Only.
Erdogan, S. et al., "Enhanced tumor MR imaging with gadolinium-loaded polychelating polymer-containing tumor-targeted liposomes", Journal of Magnetic Resonance Imaging, vol. 27, No. 3, pp. 574-580, (2008).
"Contrast media/contrast agents market worth $5.17 billion by 2020", pp. 1-5, found at www.prnewswire.com/news-releases/contrast-mediacontrast-agents-market-worth-517-billion-by-2020-511753661.html, (2015).
Hylton, N., "Dynamic contrast-enhanced magnetic resonance imaging as an imaging biomarker", Journal of Clinical Oncology, vol. 24, No. 20, pp. 3293-3298, (2006).
Choyke, P.L. et al., "Functional magnetic resonance imaging of the kidney using macromolecular contrast agents", Abdominal Imaging, vol. 31, issue 2, pp. 224-231, (2006).
Bisdas, S. et al., "A comparison of tumour perfusion assessed by deconvolution-based analysis of dynamic contrast-enhanced CT and MR imaging in patients with squamous cell carcinoma of the upper aerodigestive tract", European Radiology, vol. 18, No. 4, pp. 843-850, (2008).
Molecular Imaging and Contrast Database (MICAD), 2004-2013.
Morcos, S.K. et al., "Adverse reactions to iodinated contrast media", European Radiology, vol. 11, No. 7, pp. 1267-1275, (2001).
Marckmann, P. et al., "Nephrogenic systemic fibrosis: suspected causative role of gadodiamide used for contrast-enhanced magnetic resonance imaging", Journal of the American Society Nephrology, vol. 17, No. 9, pp. 2359-2362, (2006).
Weinmann, H-J. et al., "Tissue-specific MR contrast agents", European Journal of Radiology, vol. 46, No. 1, pp. 33-44, (2003).
Artemov, D. et al., "MR molecular imaging of the Her-2/neu receptor in breast cancer cells using targeted iron oxide nanoparticles", Magnetic Resonance in Medicine, vol. 49, No. 3, pp. 403-408, (2003).
Lakoubov, L.Z. et al., "A novel class of antitumor antibodies: nucleosome-restricted antinuclear autoantibodies (ANA) from healthy aged nonautoimmune mice", Oncology Research, vol. 9, No. 8, pp. 439-446, (1997) Abstract Only.
"Guidence for Industry: Developing Medical Imaging Drug and Biological Products", US Department of Health and Human Services, (2004).
Fisher, G.H. et al., "Induction and apoptotic regression of lung adenocarcinomas by regulation of a K-Ras transgene in the presence and absence of tumor suppressor genes", Genes Development, vol. 15, No. 24, pp. 3249-3262, (2001).
Salama, J.K. et al., "New radiotherapy and chemoradiotherapy approaches for non-small-cell lung cancer", Journal of Clinical Oncology, vol. 31, No. 8, pp. 1029-1038, (2013).
Laine, A.M. et al., "Radiation therapy as a backbone of treatment of locally advanced non-small cell lung cancer", Seminars in Oncology, vol. 41, No. 1, pp. 57-68, (2014).
Kim, B.Y.S. et al., "Nanomedicine", New England Journal of Medicine, vol. 363, No. 25, pp. 2434-2443, (2010).
Davis, M.E. et al., "Nanoparticle therapeutics: an emerging treatment modality for cancer", Nature Reviews Drug Discovery, vol. 7, No. 9, pp. 771-782, (2008).
Schroeder, A., et al., "Treating metastatic cancer with nanotechnology", Nature Reviews Cancer, vol. 12, No. 1, pp. 39-50, (2012).
Danhier, F. et al., "To exploit the tumor microenvironment: Passive and active tumor targeting of nanocarriers for anti-cancer drug delivery", Journal of Controlled Release, vol. 148, No. 2, pp. 135-146, (2010).
Papasani, M.R. et al., "Gold nanoparticles: the importance of physiological principles to devise strategies for targeted drug delivery", Nanomedicine, vol. 8, No. 6, pp. 804-814, (2012).
Dreaden, E.C., et al., "Beating cancer in multiple ways using nanogold", Chemical Society Reviews, vol. 40, No. 7, pp. 3391-3404, (2011).

(56) References Cited

OTHER PUBLICATIONS

Ghosh, P. et al., "Gold nanoparticles in delivery applications", Advanced Drug Delivery Reviews, vol. 60, No. 11, pp. 1307-1315, (2008).

Kennedy, L.C., et al., "A new era for cancer treatment: gold-nanoparticle-mediated thermal therapies", Small, vol. 7, No. 2, pp. 169-183, (2011).

Kim, C-K. et al., "Multimodal drug delivery using gold nanoparticles", Nanoscale, vol. 1, No. 1, pp. 61-67, (2009).

Khlebtsov, N. et al., "Biodistribution and toxicity of engineered gold nanoparticles: a review of in vitro and in vivo studies", Chemical Society Reviews, vol. 40, No. 3, pp. 1647-1671, (2011).

Boisselier, E. et al., "Gold nanoparticles in nanomedicine: preparations, imaging, diagnostics, therapies and toxicity", Chemical Society Reviews, vol. 38, No. 6, pp. 1759-1782, (2009).

Giljohann, D.A., et al., "Gold nanoparticles for biology and medicine", Angewandte Chemie International Edition, vol. 49, No. 19, pp. 3280-3294, (2010).

Brun, E., et al., "Parameters governing gold nanoparticle X-ray radiosensitization of DNA in solution", Colloids Surf B Biointerfaces, vol. 72, No. 1, pp. 128-134, (2009).

Jain, S., et al., "Gold nanoparticles as novel agents for cancer therapy", British Journal of Radiology, vol. 85, No. 1010, pp. 101-113, (2012).

Jeong, S-Y., et al., "Systemic delivery and preclinical evaluation of Au nanoparticle containing beta-lapachone for radiosensitization", Journal of Controlled Release, vol. 139, No. 3, pp. 239-245, (2009).

Chattopadhyay, N., et al., "Molecularly targeted gold nanoparticles enhance the radiation response of breast cancer cells and tumor xenografts to X-radiation", Breast Cancer Research and Treatment, vol. 137, No. 1, pp. 81-91, (2013).

Butterworth, K.T., et al., "Evaluation of cytotoxicity and radiation enhancement using 1.9 nm gold particles: potential application for cancer therapy", Nanotechnology, vol. 21, No. 29, pp. 1-18, (2010).

Carter, J.D., et al., "Nanoscale energy deposition by X-ray absorbing nanostructures", The Journal of Physical Chemistry B, vol. 111, No. 40, pp. 11622-11625, (2007).

Foley, E.A. et al., "Enhanced relaxation of nanoparticle-bound supercoiled DNA in X-ray radiation", Chemical Communications, vol. 25, pp. 3192-3194, (2005).

Zheng, Y., et al., "Radiosensitization of DNA by gold nanoparticles irradiated with high-energy electrons", Radiation Research, vol. 169, No. 1, pp. 19-27, (2008).

Misawa, M. et al., "Generation of reactive oxygen species induced by gold nanoparticles under x-ray and UV Irradiations", Nanomedicine, vol. 7, No. 5, pp. 604-614, (2011).

Chithrani, B.D. et al., "Gold nanoparticles as radiation sensitizers in cancer therapy", Radiation Research, vol. 173, No. 6, pp. 719-728, (2010).

Chang, M-Y., et al., "Increased apoptotic potential and dose-enhancing effect of gold nanoparticles in combination with single-dose clinical electron beams on tumor-bearing mice", Cancer Science, vol. 99, No. 7, pp. 1479-1484, (2008).

Szegezdi, E., et al., "Mediators of endoplasmic reticulum stress-induced apoptosis", EMBO Reports, vol. 7, No. 9, pp. 880-885, (2006).

Regulla, D.F. et al., "Physical and biological interface dose effects in tissue due to X-ray-induced release of secondary radiation from metallic gold surfaces", Radiation Research, vol. 150, No. 1, pp. 92-100, (1998).

Ngwa, W. et al., "Targeted radiotherapy with gold nanoparticles: current status and future perspectives", Nanomedicine, vol. 9, No. 7, pp. 1063-1082, (2014).

Luo, Y-L. et al., "Release of photoactivatable drugs from plasmonic nanoparticles for targeted cancer therapy", ACS Nano, vol. 5, No. 10, pp. 7796-7804, (2011).

Li, N. et al., "Directed evolution of gold nanoparticle delivery to cells", Chemical Communications (Camb), vol. 46, No. 3, pp. 1-8, (2010).

Yu, C. et al., "Novel aptamer-nanoparticle bioconjugates enhances delivery of anticancer drug to MUC1—positive cancer cells in vitro", PLoS One, vol. 6, No. 9, pp. 1-8, (2011).

Kurosaki, T. et al., "Self-assemble gene delivery system for molecular targeting using nucleic acid aptamer", Gene, vol. 491, No. 2, pp. 205-209, (2012).

Orava, E.W. et al., "Delivering cargoes into cancer cells using DNA aptamers targeting internalized surface portals", Biochimica et Biophysica Acta, vol. 1798, No. 12, pp. 2190-2200, (2010).

Dhar, S. et al., "Targeted delivery of a cisplatin prodrug for safer and more effective prostate cancer therapy in vivo", Proceedings of the National Academy of Science, vol. 108, No. 5, pp. 1850-1855, (2011).

Dhar, S. et al., "Targeted delivery of cisplatin to prostate cancer cells by aptamer functionalized Pt(IV) prodrug-PLGA-PEG nanoparticles", Proceedings of the National Academy of Science, vol. 105, No. 45, pp. 17356-17361, (2008).

Min, K. et al., "Dual-aptamer-based delivery vehicle of doxorubicin to both PSMA (+) and PSMA (−) prostate cancers", Biomaterials, vol. 32, No. 8, pp. 2124-2132, (2011).

Kolishetti, N. et al., "Engineering of self-assembled nanoparticle platform for precisely controlled combination drug therapy", Proceedings of the National Academy of Science, vol. 107, No. 42, pp. 17939-17944, (2010).

Kim, D. et al., "A drug-loaded aptamer-gold nanoparticle bioconjugate for combined CT imaging and therapy of prostate cancer", ACS Nano, vol. 4, No. 7, pp. 3689-3696, (2010).

Gu, F. et al., "Precise engineering of targeted nanoparticles by using self-assembled biointegrated block copolymers", Proceedings of the National Academy of Science, vol. 105, No. 7, pp. 2586-2591, (2008).

Farokhzad, O.C. et al., "Targeted nanoparticle-aptamer bioconjugates for cancer chemotherapy in vivo", Proceedings of the National Academy of Science, vol. 103, No. 16, pp. 6315-6320, (2006).

Gao, H. et al., "Precise glioma targeting of and penetration by aptamer and peptide dual-functioned nanoparticles", Biomaterials, vol. 33, No. 20, pp. 5115-5123, (2012).

Rizzieri, D, et al., "Long-term outcome of responders in a randomized, controlled Phase II trial of aptamer AS1411 in AML", Journal of Clinical Oncology, vol. 28, No. 15s, supplemental abstract 6557, (2010).

Lian, S. et al., "A universal quantum dots-aptamer probe for efficient cancer detection and targeted imaging", Journal of Nanoscience and Nanotechnology, vol. 12, No. 10, pp. 7703-7708, (2012).

Wu, J. et al., "Nucleolin targeting AS1411 modified protein nanoparticle for antitumor drugs delivery", Molecular Pharmaceutics, vol. 10, No. 10, pp. 3555-3563, (2013).

Hurst, S.J. et al., "Maximizing DNA loading on a range of gold nanoparticle sizes", Analytical Chemistry, vol. 78, No. 24, pp. 8313-8318, (2006).

Kwatra, D. et al., "Nanoparticles in radiation therapy: a summary of various approaches to enhance radiosensitization in cancer", Translational Cancer Research, vol. 2, No. 4, pp. 330-342, (2013).

McLaughlin, M.F. et al., "Gold coated lanthanide phosphate nanoparticles for targeted alpha generator radiotherapy", PLoS One, vol. 8, issue 1, pp. 1-8, (2013).

Goldstein, M. et al., "Nucleolin mediates nucleosome disruption critical for DNA double-strand break repair", Proceedings of the National Academy of Science, vol. 110, No. 42, pp. 16874-16879, (2013).

Kobayashi, J. et al., "Nucleolin participates in DNA double-strand break-induced damage response through MDC1-dependent pathway", PLoS One, vol. 7, issue 11, pp. 1-12, (2012).

Yang, C. et al., "Nucleolin binds to the proliferating cell nuclear antigen and inhibits nucleotide excision repair", Molecular and Cellular Pharmacology, vol. 1, No. 3, pp. 130-137, (2009).

Cai, Z., et al., "Computational analysis of the number, area and density of gamma-H2AX foci in breast cancer cells exposed to $^{111}$In-DTPA-hEGF or gamma-rays using Image-J software", International Journal of Radiation Biology, vol. 85, issue 3, pp. 262-271, (2009).

(56) References Cited

OTHER PUBLICATIONS

Yamaguchi, M. et al., "Role of reactive oxygen species in the radiation response of human hematopoietic stem/progenitor cells", PLoS One, vol. 8, issue 7, pp. 1-7, (2013).
Voskoglou-Nomikos, T. et al., "Clinical predictive value of the in vitro cell line, human xenograft, and mouse allograft preclinical cancer models", Clinical Cancer Research, vol. 9, No. 11, pp. 4227-4239, (2003).
Kelland, L.R., ""Of mice and men": values and liabilities of the athymic nude mouse model in anticancer drug development", European Journal of Cancer, vol. 40, issue 6, pp. 827-836, (2004).
Tiffen, J.C. et al., "Luciferase expression and bioluminescence does not affect tumor cell growth in vitro or in vivo", Molecular Cancer, vol. 9, pp. 1-8, (2010).
Wang, S. et al., "Requirement of p53 targets in chemosensitization of colonic carcinoma to death ligand therapy", Proceedings of the National Academy of Science, vol. 100, No. 25, pp. 15095-15100, (2003).
Viola, R.J., et al., "In vivo bioluminescence imaging monitoring of hypoxia-inducible factor 1 alpha, a promoter that protects cells, in response to chemotherapy", American Journal of Roentgenology, vol. 191, No. 6, pp. 1779-1784, (2008).
Close, D.M. et al., "In vivo bioluminescent imaging (BLI): noninvasive visualization and interrogation of biological processes in living animals", Sensors, vol. 11, No. 1, pp. 180-206, (2011).
Troy, T. et al., "Quantitative comparison of the sensitivity of detection of fluorescent and bioluminescent reporters in animal models", Molecular Imaging, vol. 3, No. 1, pp. 9-23, (2004).
Lee, C.J. et al., "In vivo bioluminescent imaging of irradiated orthotopic pancreatic cancer xenografts in nonobese diabetic-severe combined immunodeficient mice: a novel method for targeting and assaying efficacy of ionizing radiation", Translational Oncology, vol. 3, No. 3, pp. 153-159, (2010).
Bouvet, M. et al., "Real-time optical imaging of primary tumor growth and multiple metastatic events in a pancreatic cancer orthotopic model", Cancer Research, vol. 62, No. 5, pp. 1534-1540, (2002).
Caceres, G. et al., "Imaging of luciferase and GFP-transfected human turnours in nude mice", Luminescence, vol. 18, No. 4, pp. 218-223, (2003).
Bouchard, M.B. et al., "Technical considerations in longitudinal multispectral small animal molecular imaging", Journal of Biomedical Optics, vol. 12, No. 5, pp. 051601-1-051601-11, (2007).
Bhaumik, S. et al., "Strategies to minimize background autofluorescence in live mice during noninvasive fluorescence optical imaging", Lab Animal, vol. 36, No. 8, pp. 40-43, (2007).
Li, B. et al., "A novel bioluminescence orthotopic mouse model for advanced lung cancer", Radiation Research, vol. 176, No. 4, pp. 486-493, (2011).
Mordant, P. et al., "Bioluminescent orthotopic mouse models of human localized non-small cell lung cancer: feasibility and identification of circulating tumour cells", PLoS One, vol. 6, issue 10, pp. 1-9, (2011).
Chauhan, R. et al., "Three-component bioactive nanoparticle as an image guided cancer nanotheranostic agent", Conference Abstract, 1 page, published online Aug. 26, 2015.
Lammers, T. et al., "Nanotheranostics and image-guided drug delivery: Current concepts and future directions", Molecular Pharmaceutics, vol. 7, No. 6, pp. 1899-1912, (2010).
Masitas, R.A. et al., "Oxidation of highly unstable <4 nm diameter gold nanoparticles 850 mV negative of the bulk oxidation potential", Journal of the American Chemical Society, vol. 134, No. 11, pp. 5014-5017, (2012).
"Cancer Facts & Figures 2014", American Cancer Society, pp. 1-67, (2014).
Laber, D. et al., "Long term clinical response in renal cell carcinoma patients treated with quadruplex formin• oliqonucleotides", Clinical Cancer Research, vol. 11, p. 9088S, (2005).
Chauhan, R. et al., "Three-component bioactive nanoparticle as an image guided cancer nanotheranostic agent", Biomedical Engineering Society Abstract, Public Presentation, Apr. 23, 2015.
Guo, J. et al., "Aptamer-functionalized PEG-PLGA nanoparticles for enhanced anti-glioma drug delivery", Biomaterials, vol. 32, pp. 8010-8020, (2011).
Perez-Herrero, E. et al., "Advanced targeted therapies in cancer: Drug nanocarriers, the future of chemotherapy", European Journal of Pharmaceutics and Biopharmaceutics, vol. 93, pp. 52-79, (2015).
Fernandes, D.A. et al., "Synthesis of Stable Multifunctional Perfluorocarbon Nanoemulsions for Cancer Therapy and Imaging", Langmuir, vol. 32, No. 42, pp. 10870-10880, (2016).
Gupta, R. et al., "Polymeric micelles and nanoemulsions as drug carriers: Therapeutic efficacy, toxicity, and drug resistance", Journal of Controlled Release, vol. 212, pp. 70-77, (2015).
Rapoport, N. et al., "Polymeric micelles and nanoemulsions as tumor-targeted drug carriers: Insight through intravital imaging", Journal of Controlled Release, vol. 206, pp. 153-160, (2015).
Kripfgans, O.D. et al., "Acoustic droplet vaporization for therapeutic and diagnostic applications", Ultrasound in Medicine & Biology, vol. 26, issue 7, pp. 1177-1189, (2000).
Shiao, Y.S. et al., "Aptamer-functionalized gold nanoparticles as photoresponsive nanoplatform for co-drug delivery", ACS Appl Mater Interfaces, vol. 6, No. 24, pp. 21832-21841, (2014).
Li, X. et al., "Targeted delivery of anticancer drugs by aptamer AS1411 mediated Pluronic F127/cyclodextrin-linked polymer composite micelles", Nanomedicine: Nanotechnology, Biology and Medicine, vol. 11, issue 1, pp. 175-184, (2015).
Zhang, J. et al., "Nucleolin targeting AS1411 aptamer modified pH-sensitive micelles: A dual-functional strategy for paclitaxel delivery", Journal of Controlled Release, vol. 213, pp. e137-e138, (2015).
Ma, H. et al., "Effects of AuNPs @ PEG-AS1411 nanoparticles on radiosensitization of HeLa cancer cells", Chinese Journal of Radiological Medicine and Protection, vol. 35, No. 11, pp. 809-814, (2015).
38 Pages, Aug. 30, 2019, U.S. Appl. No. 15/240,780, US.

\* cited by examiner

2HRS POST INJECTION

6HRS POST INJECTION

NON-TREATED

GOLD NANOPARTICLES

GNP-CRO (200nM)

GNP-AS1411 (200nM)

NON-TREATMENT GROUP

AS1411-Gd-GNP-Cy5

CRO-Gd-GNP-Cy5

NON-TREATMENT GROUP

AS1411-Gd-GNP-Cy5

CRO-Gd-GNP-Cy5

FIG. 15B

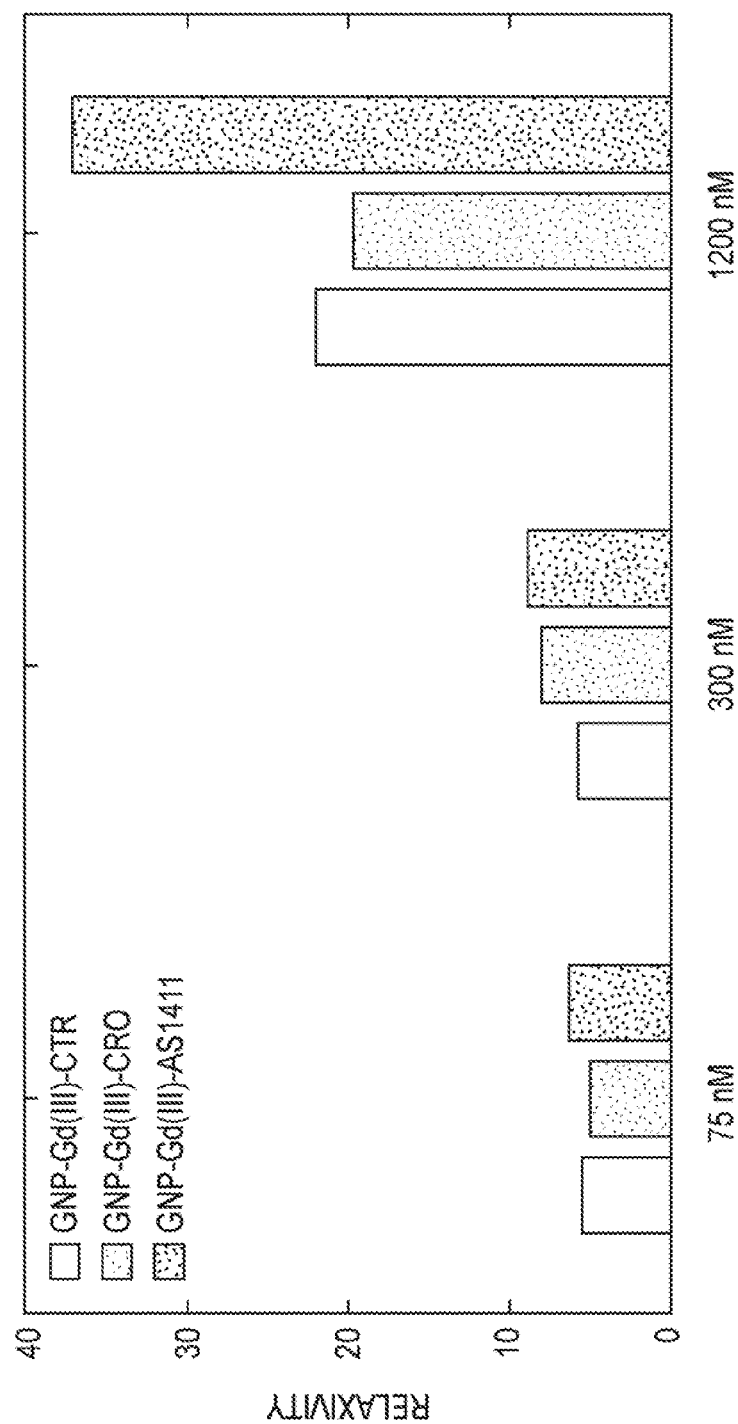

SEQUENCE LISTING

```
<160> NUMBER OF SEQ ID NOS: 41

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 1
tttggtggtg gtggttgtgg tggtggtgg                                            29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 2
tttggtggtg gtggttttgg tggtggtgg                                            29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 3
tttggtggtg gtggtggtgg tggtggtgg                                            29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 4
tttggtggtg gtggtttggg tggtggtgg                                            29

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 5
tggtggtggt ggt                                                             13
```

```
<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 6
ggtggttgtg gtgg                                                           14

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 7
gttgtttggg gtggt                                                          15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 8 ttggggggggg tgggt                                                         15

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 9
ggttggggtg ggtggggtgg gtggg                                               25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 10
ggtggtggtg gttgtggtgg tggtgg                                              26

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 11
tttggtggtg gtggttgtgg tggtggtg                                            28

<210> SEQ ID NO 12
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 12
tttggtggtg gtggtgtggt ggtggtgg                                              28

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 13
ggtggtggtg gttgtggtgg tggtggttt                                             29

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 14
ggtggttgtg gtggttgtgg tggttgtggt gg                                         32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 15
tttggtggtg gtggttgtgg tggtggtggt tt                                         32

<210> SEQ ID NO 16
<211> LENGTH: 56
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 16
ggtggtggtg gttgtggtgg tggtggttgt ggtggtggtg gttgtggtgg tggtgg               56

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 17
tcgagaaaaa ctctcctctc cttccttcct ctcca                                      35

<210> SEQ ID NO 18
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 18
tttcctcctc ctccttctcc tcctcctcc                                           29

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 19
ttagggttag ggttagggtt aggg                                                24

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 20
ggtggtggtg g                                                              11

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 21
ggtggttgtg gtgg                                                           14

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 22
ggttggtgtg gttgg                                                          15

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 23
gggttttggg                                                                10

<210> SEQ ID NO 24
<211> LENGTH: 20
<212> TYPE: DNA
```

<213> ORGANISM: Artificial Sequence
<220> FEATURE:
<223> OTHER INFORMATION: Description of Artificial Sequence: Synthetic
      polynucleotide sequence

<400> SEQUENCE: 24
ggttttggtt ttggttttgg                                              20

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 25
ggttggtgtg gttgg                                                   15

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 26
ggggttttgg gg                                                      12

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 27
gggttttggg                                                         10

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 28
ggggttttgg ggttttgggg ttttgggg                                     28

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 29
ttggggttgg ggttggggtt gggg                                         24

<210> SEQ ID NO 30
<211> LENGTH: 16
<212> TYPE: DNA
<213> ORGANISM: Artificial Sequence

```
<220> FEATURE:
<223> OTHER INFORMATION: Description of Artificial Sequence: Synthetic
      polynucleotide sequence

<400> SEQUENCE: 30
gggtgggtgg gtgggt                                                        16

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 31
ggttttggtt ttggttttgg ttttgg                                             26

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 32
tttcctcctc ctccttctcc tcctcctcc                                          29

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 33
cctcctcctc cttctcctcc tcctcc                                             26

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 34 tggggt                                                                    6

<210> SEQ ID NO 35
<211> LENGTH: 7
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 35 gcatgct                                                                   7

<210> SEQ ID NO 36
<211> LENGTH: 11
<212> TYPE: DNA
<213> ORGANISM: Artificial Sequence
<220> FEATURE:
```

```
<223> OTHER INFORMATION: Description of Artificial Sequence: Synthetic
      polynucleotide sequence

<400> SEQUENCE: 36
gcggtttgcg g                                                              11

<210> SEQ ID NO 37
<211> LENGTH: 4
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 37 tagg                                                                       4

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 38
ggggttgggg tgtgggttg ggg                                                  23

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 39 tttttggtg gtggtggttg tggtggtggt ggttt                                     35

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 40 tttttcctc ctcctccttc tcctcctcct cctt                                      35

<210> SEQ ID NO 41
<211> LENGTH: 4
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 41 tttt                                                                       4
```

ANTI-NUCLEOLIN AGENT-CONJUGATED NANOPARTICLES AS RADIO-SENSITIZERS AND MRI AND/OR X-RAY CONTRAST AGENTS

The application hereby incorporates by reference the Sequence Listing titled "LOU01-027-US_Sequence_Listing.txt", created on Jan. 20, 2018, having a file size of 11 KB.

BACKGROUND

Nucleolin [8] is an abundant, non-ribosomal protein of the nucleolus, the site of ribosomal gene transcription and packaging of pre-ribosomal RNA. This 710 amino acid phosphoprotein has a multi-domain structure consisting of a histone-like N-terminus, a central domain containing four RNA recognition motifs and a glycine/arginine-rich C-terminus, and has an apparent molecular weight of 110 kD. While nucleolin is found in every nucleated cell, the expression of nucleolin on the cell surface has been correlated with the presence and aggressiveness of neoplastic cells [3].

The correlation of the presence of cell surface nucleolin with neoplastic cells has been used for methods of determining the neoplastic state of cells by detecting the presence of nucleolin on the plasma membranes [3]. This observation has also provided new cancer treatment strategies based on administering compounds that specifically target nucleolin [4].

Nucleic acid aptamers are short synthetic oligonucleotides that fold into unique three-dimensional structures that can be recognized by specific target proteins. Thus, their targeting mechanism is similar to monoclonal antibodies, but they may have substantial advantages over these, including more rapid clearance in vivo, better tumor penetration, non-immunogenicity, and easier synthesis and storage.

Guanosine-rich oligonucleotides (GROs) designed for triple helix formation are known for binding to nucleolin. This ability to bind nucleolin has been suggested to cause their unexpected ability to effect antiproliferation of cultured prostate carcinoma cells [6]. The antiproliferative effects are not consistent with a triplex-mediated or an antisense mechanism, and it is apparent that GROs inhibit proliferation by an alternative mode of action. It has been surmised that GROs, which display the propensity to form higher order structures containing G-quartets, work by an aptamer mechanism that entails binding to nucleolin due to a shape-specific recognition of the GRO structure; the binding to cell surface nucleolin then induces apoptosis. The antiproliferative effects of GROs have been demonstrated in cell lines derived from prostate (DU145), breast (MDA-MB-231, MCF-7), or cervical (HeLa) carcinomas and correlates with the ability of GROs to bind cell surface nucleolin [6].

AS1411, a GRO nucleolin-binding DNA aptamer that has antiproliferative activity against cancer cells with little effect on non-malignant cells, was previously developed. AS1411 uptake appears to occur by macropinocytosis in cancer cells, but by a nonmacropinocytic pathway in nonmalignant cells, resulting in the selective killing of cancer cells, without affecting the viability of nonmalignant cells [9]. AS1411 was the first anticancer aptamer tested in humans and results from clinical trials of AS1411 (including Phase II studies in patients with renal cell carcinoma or acute myeloid leukemia) indicate promising clinical activity with no evidence of serious side effects. Despite a few dramatic and durable clinical responses, the overall rate of response to AS1411 was low, possibly due to the low potency of AS1411.

Anti-nucleolin agents conjugated to particles, such as aptamers conjugated to gold nanoparticles, have an antiproliferative effect on cancer and tumors. See International Application, International Publication Number WO 2012/167173, entitled "ANTI-NUCLEOLIN AGENT-CONJUGATED NANOPARTICLES", filed 1 Jun. 2012, to Bates et al. Aptamer conjugated gold nanoparticles, in particular, have a similar or greater antiproliferative effect than the aptamer (anti-nucleolin oligonucleotide) alone, demonstrating similar effects at only $1/10$ to $1/100$ the dosage. Furthermore, these same agents, preferably having a fluorescent dye conjugated to the particle or attached to the anti-nucleolin agent, may also be used as imaging agents, both in vivo and ex vivo.

Radiation therapy (RT) has been a mainstay of cancer treatment for decades and advances in technology mean it is now used to treat more patients than ever before. The vast majority of cancer patients will receive RT as part of their treatment, but this therapy is not without limitations or side effects. The ability to deliver sufficient radiation intensity to the tumor without causing unacceptable toxicity in nearby tissues is the overarching problem that constrains the efficacy of RT and leads to local tumor relapse and recurrence.

As the use of RT has grown, the need for potent and selective radiosensitizing agents has never been greater. Certain types of aggressive cancers are particularly difficult to treat with RT. One such example is the "triple negative" subtype of breast cancer (TNBC), which represents 15-25% of breast cancer occurrences and is characterized as an aggressive disease with early relapse, low post-recurrence survival, and worse overall survival than other forms of breast cancer. Moreover, TNBC has proven more resistant to radiation therapy and larger doses are needed for effective treatment. Patients with recurrent TNBC are notably challenging to treat, as they may already be near their maximum safe lifetime radiation dose and there are few clear guidelines for RT in this setting.

RT also plays an extremely important role in the management of non-small cell lung cancer (NSCLC) and most patients with NSCLC will receive RT at some point during their course of treatment. Although RT has proven clinical benefits, it is often inadequate at controlling primary NSCLC tumor growth and preventing recurrence. Increasing the dose of radiation to the tumor is expected to improve effectiveness, but dose escalation is not currently achievable in most cases due to the damage it would cause to surrounding healthy tissues.

For many years, there has been interest in developing radiosensitizers to improve the efficacy of RT, but there are currently no agents that are FDA approved for clinical use specifically for this purpose. Several chemotherapy drugs have radiosensitizing properties and have been tested concurrently with RT, but the problem is that they can also make normal tissues more susceptible to radiation damage. Gold nanoparticles (GNP) are well established as radiosensitizers due to their high atomic number (Z), which means they emit secondary radiation when subjected to ionizing radiation, plus they are biocompatible. However, the GNP generally do not internalize efficiently in cancer cells or accumulate in tumors at sufficiently high concentrations for effective radiosensitization, which has limited their clinical utility [26].

Each year in this country, more than 71 million CT scans and 33 million MRI scans are performed. The purpose for many of these scans is to detect (or rule out) primary or metastatic malignant tumors. In oncology, medical imaging plays a major role in screening, diagnosis, staging, monitoring therapeutic response, and treatment planning (e.g. for radiation therapy or surgery) for almost all cancer types. In most of those cases, an intravenous (i.v.) contrast agent is administered prior to CT or MRI scans to improve visualization of tissues and organs. The short half-life of contrast agents in circulation often requires repeated or continuous administration throughout the imaging process. The materials in the contrast agents interact with the imaging modality; for example, iodine in CT contrast absorbs and scatters X-rays, whereas the gadolinium ions in MRI contrast are paramagnetic and alter the properties of nearby water molecules. Consequently, contrast agents can enhance differences in signals between adjacent tissues due to their altered deposition or interactions, which may depend on tissue type, architecture, or blood flow. Existing CT and MRI contrast agents are safe in most patients and effectively enhance anatomical imaging, but they are not disease-specific and largely fail to distinguish malignant from benign masses.

Diagnostic imaging is particularly important for lung cancer, which is the leading cause of cancer deaths in the United States and worldwide. With an aging population of smokers, former smokers and the smaller population of never-smokers who are susceptible to lung adenocarcinomas due to EGFR mutations, lung cancer is expected to remain a major public health problem for many years to come even if smoking cessation efforts are successful. A major factor contributing to the high mortality of lung cancer is the failure to detect lung cancers at an early stage before they invade surrounding tissue or spread to other organs (only 15% of lung cancers are detected while still localized). The clinical relevance of delayed diagnosis in lung cancer is highlighted by the fact that people whose cancer is detected while still localized to the primary site in the lung have a five year survival rate of 53%, compared to a 1% chance of surviving five years for those with distant metastases at the time of diagnosis.

Current lung cancer screening techniques include low-dose helical computed tomography (CT) and single-view posteroanterior chest radiography. Both of these screening techniques have an extremely high false positive rate (96.4% for low-dose CT and 94.5% for radiography according to a recent national study). These high rates of false positives necessitate additional secondary tests to accurately diagnose the presence or absence of lung cancer, which reduces the cost-effectiveness of these cancer screening techniques. False positive test results also cause a significant amount of unnecessary anxiety and emotional stress for patients who believe they have lung cancer.

Another limitation of imaging-based lung cancer screening techniques is their inability to differentiate between benign and malignant masses. Imaging-based tests identify lung cancer based on the size of nodules present in the lungs, with lesions smaller than 4 mm considered benign. Diagnosis based on nodule size fails to identify small malignant lesions as cancerous and precludes early-stage detection of lung cancer. In addition, larger benign growths are wrongly identified as cancerous and require more invasive secondary tests to positively diagnose the presence or absence of lung cancer.

SUMMARY

In a first aspect, the present invention is a composition comprising an anti-nucleolin agent and optionally gadolinium conjugated to nanoparticles.

In a second aspect, the present invention is a pharmaceutical composition for treating cancer, comprising an anti-nucleolin agent and optionally gadolinium conjugated to nanoparticles and a pharmaceutically acceptable carrier.

In a third aspect, the present invention is a pharmaceutical composition for enhancing the effectiveness of radiation therapy and/or enhancing contrast in X-ray imaging techniques, comprising an anti-nucleolin agent conjugated to nanoparticles and a pharmaceutically acceptable carrier.

In a fourth aspect, the present invention is a pharmaceutical composition for MRI imaging or enhancing the contrast of an MRI image, comprising an anti-nucleolin agent conjugated to nanoparticles and a pharmaceutically acceptable carrier.

In a fifth aspect, the present invention is a method of treating cancer, comprising administering an effective amount of a pharmaceutical composition to a patient in need thereof, followed by radiation therapy.

In a sixth aspect, the present invention is a use of a pharmaceutical composition for the preparation of a medicament for the treatment of cancer.

In a seventh aspect, the present invention is an agent for MRI imaging and/or enhancing contrast in X-ray imaging techniques comprising a composition which optionally comprises gadolinium, and a pharmaceutically acceptable carrier.

In an eighth aspect, the present invention is a method of imaging cancer by MRI and/or X-ray imaging techniques in vivo, comprising administering an imaging agent which optionally comprises gadolinium, to a subject; and forming an image of the imaging agent present in the subject by MRI and/or an X-ray imaging technique.

Definitions

The term "conjugated" means "chemically bonded to".

The term "anti-nucleolin oligonucleotides" refers to an oligonucleotide that binds to nucleolin.

The term "equivalent aptamer concentration" refers to the concentration of anti-nucleolin oligonucleotide present in the conjugate.

Tumors and cancers include solid, dysproliferative tissue changes and diffuse tumors. Examples of tumors and cancers include melanoma, lymphoma, plasmocytoma, sarcoma, glioma, thymoma, leukemia, breast cancer, prostate cancer, colon cancer, liver cancer, esophageal cancer, brain cancer, lung cancer, ovary cancer, endometrial cancer, bladder cancer, kidney cancer, cervical cancer, hepatoma, and other neoplasms. For more examples of tumors and cancers, see, for example Stedman [1].

"Treating a tumor" or "treating a cancer" means to significantly inhibit growth and/or metastasis of the tumor or cancer, and/or killing cancer cells. Growth inhibition can be indicated by reduced tumor volume or reduced occurrences of metastasis. Tumor growth can be determined, for example, by examining the tumor volume via routine procedures (such as obtaining two-dimensional measurements with a dial caliper). Metastasis can be determined by inspecting for tumor cells in secondary sites or examining the metastatic potential of biopsied tumor cells in vitro.

A "chemotherapeutic agent" is a chemical compound that can be used effectively to treat cancer in humans.

A "pharmaceutically acceptable carrier" includes any and all solvents, dispersion media, coatings, antibacterial and antifungal agents, isotonic and absorption delaying agents which are compatible with pharmaceutical administration. Preferred examples of such carriers or diluents include water, saline, Ringer's solutions and dextrose solution. Supplementary active compounds can also be incorporated into the compositions.

"Medicament," "therapeutic composition" and "pharmaceutical composition" are used interchangeably to indicate a compound, matter, mixture or preparation that exerts a therapeutic effect in a subject.

"Antibody" is used in the broadest sense and refers to monoclonal antibodies, polyclonal antibodies, multispecific antibodies, antibody fragments and chemically modified antibodies, where the chemical modification does not substantially interfere with the selectivity and specificity of the antibody or antibody fragment.

An "anti-nucleolin agent" includes any molecule or compound that interacts with nucleolin. Such agents include for example anti-nucleolin antibodies, aptamers such GROs and nucleolin targeting proteins.

"X-ray based imaging techniques" include all imaging techniques which use X-rays to form an image, directly or indirectly, including for example CT scans (also called X-ray computed tomography or computerized axial tomography scan (CAT scan)).

BRIEF DESCRIPTION OF THE DRAWINGS

FIG. 15B illustrates uptake and selective retention of fluorescent-labeled gold nanoparticle-gadolinium-oligomer conjugates in malignant breast cancer cells.

FIG. 17B illustrates the change in relaxivity of gold nanoparticle-oligomer-gadolinium conjugates in cells after 48 hours of treatment.

DETAILED DESCRIPTION

Figure 1A:
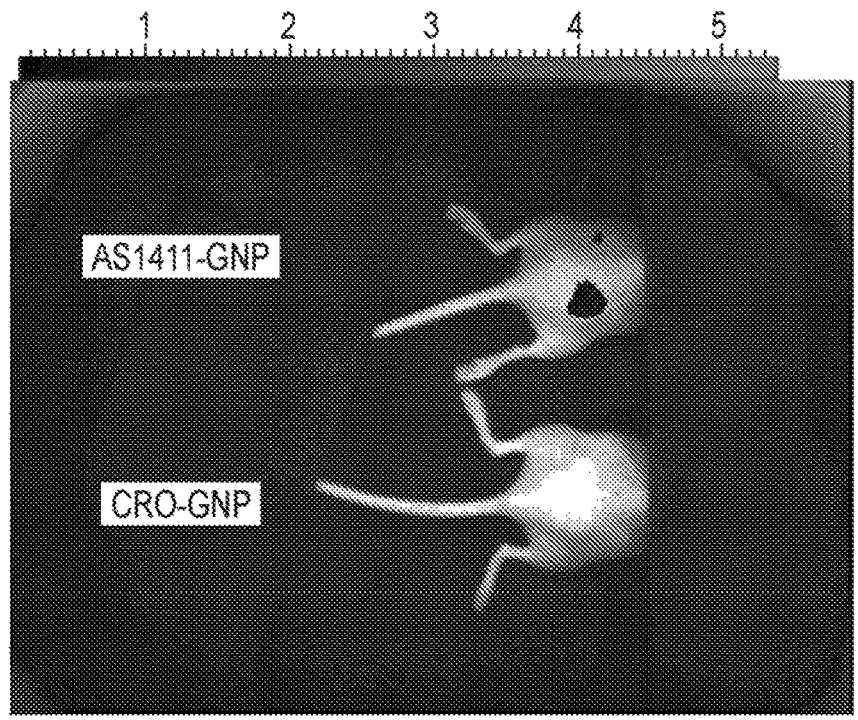
FIGS. 1A and 1B are images of two MDA231 xenograft mice injected retro-orbitally with about 200 ng/100 uL of AS1411-Cy5-GNP or CRO-Cy5-GNP. Image was acquired using a PHOTON IMAGER™ after 2 hrs (A) and 6 hrs (B) post injection.

The present invention includes anti-nucleolin agents conjugated to particles comprising metals, such as aptamers conjugated to gold nanoparticles, that are effective radio-sensitizers for treating cancer. The nanoparticles are selectively taken-up by cancer cells and enhance the effects of RT on those cells. This enhances the effectiveness of RT, and/or allows a low effective dose of radiation to be used during RT. Furthermore, the nanoparticles may optionally also contain gadolinium, for example 10-(2-sulfanylethyl)-1,4,7,10-tetraazacyclododecane-1,4,7-triacetic acid (H3-DO3A-SH) coordinated to a trivalent gadolinium ion (Gd-DO3A-SH), which is then bound to the gold nanoparticles through the sulfur atom in a manner similar to thiolated-AS1411, resulting in a mono-layer coating that is a mixture of AS1411 and Gd-DO3A-SH on the gold nanoparticles. The Gd ions of Gd-DO3A-SH enhance the relaxivity (speed up the relaxation rate) of nearby water molecules during an MRI scan and contribute to an increase in contrast when present in the sample being scanned. In addition, both the gold nanoparticles and the Gd ions enhance the absorption and scattering of X-rays, and increase the contrast when present in the sample being scanned or imaged using X-ray based imaging techniques, such as CT scanning. The combination of anti-nucleolin agents (cancer targeting) and gadolinium (MRI contrast enhancement) combine to result in a cancer-targeting MRI-contrast agent. Furthermore the combination of anti-nucleolin agents (cancer targeting) and gold nanoparticle (X-ray contrast enhancement) and optionally gadolinium (MRI contrast enhancement and X-ray contrast enhancement) combine to result in a cancer-targeting MRI-contrast and X-ray (CT scan) contrast agent.

There are several unmet needs that can be addressed by these cancer-targeted contrast agent, namely: (1) better specificity to differentiate between cancerous and non-cancerous lesions and reduce false positives that can lead to over-treatment, (2) improved sensitivity so that they could be used as screening tools for early detection, and (3) reduced toxicity to allow use in patients with compromised renal function for whom existing contrast agents are contraindicated. These advantages are especially useful in lung cancer screening, particularly early detection of lung cancer.

In addition, anti-nucleolin agent-conjugated nanoparticles have a longer half-life in circulation than currently available contrast agents. The longer half-life in circulation eliminates the need for continuous intravenous administration during imaging, which greatly improves patient comfort. Anti-nucleolin agent-conjugated nanoparticle contrast agents may be administered multiple days before an imaging scan is performed.

Anti-nucleolin agents include (i) aptamers, such as GROs; (ii) anti-nucleolin antibodies; and (iii) nucleolin targeting proteins. Examples of aptamers include guanosine-rich oligonucleotides (GROs). Examples of suitable oligonucleotides and assays are also given in Miller et al. [7]. Characteristics of GROs include:

(1) having at least 1 GGT motif,
(2) preferably having 4-100 nucleotides, although GROs having many more nucleotides are possible,
(3) optionally having chemical modifications to improve stability.

Especially useful GROs form G-quartet structures, as indicated by a reversible thermal denaturation/renaturation profile at 295 nm [6]. Preferred GROs also compete with a telomere oligonucleotide for binding to a target cellular protein in an electrophoretic mobility shift assay [6]. In some cases, incorporating the GRO nucleotides into larger nucleic acid sequences may be advantageous; for example, to facilitate binding of a GRO nucleic acid to a substrate without denaturing the nucleolin-binding site. Examples of oligonucleotides are shown in Table 1; preferred oligonucleotides include SEQ IDs NOs: 1-7; 9-16; 19-30 and 31 from Table 1.

TABLE 1

Non-antisense GROs that bind nucleolin and non-binding controls[1,2,3].

| GRO | Sequence | SEQ ID NO: |
|---|---|---|
| GRO29A[1] | tttggtggtg gtggttgtgg tggtggtgg | 1 |
| GRO29-2 | tttggtggtg gtggttttgg tggtggtgg | 2 |
| GRO29-3 | tttggtggtg gtggtggtgg tggtggtgg | 3 |
| GRO29-5 | tttggtggtg gtggtttggg tggtggtgg | 4 |
| GRO29-13 | tggtggtggt ggt | 5 |
| GRO14C | ggtggttgtg gtgg | 6 |
| GRO15A | gttgtttggg gtggt | 7 |
| GRO15B[2] | ttggggggggg tgggt | 8 |
| GRO25A | ggttggggtg ggtggggtgg gtggg | 9 |
| GRO26B[1] | ggtggtggtg gttgtggtgg tggtgg | 10 |
| GRO28A | tttggtggtg gtggttgtgg tggtggtg | 11 |
| GRO28B | tttggtggtg gtggtgtggt ggtggtgg | 12 |
| GRO29-6 | ggtggtggtg gttgtggtgg tggtggttt | 13 |
| GRO32A | ggtggttgtg gtggttgtgg tggttgtggt gg | 14 |
| GRO32B | tttggtggtg gtggttgtgg tggtggtggt tt | 15 |
| GRO56A | ggtggtggtg gttgtggtgg tggtggttgt ggtggtggtg gttgtggtgg tggtgg | 16 |
| CRO | tttcctcctc ctccttctcc tcctcctcc | 18 |
| GRO A | ttagggttag ggttagggtt aggg | 19 |
| GRO B | ggtggtggtg g | 20 |
| GRO C | ggtggttgtg gtgg | 21 |
| GRO D | ggttggtgtg gttgg | 22 |
| GRO E | gggttttggg | 23 |
| GRO F | ggttttggtt ttggttttgg | 24 |

TABLE 1-continued

Non-antisense GROs that bind nucleolin and non-binding controls[1,2,3].

| GRO | Sequence | SEQ ID NO: |
|---|---|---|
| GRO G[1] | ggttggtgtg gttgg | 25 |
| GRO H[1] | ggggttttgg gg | 26 |
| GRO I[1] | gggttttggg | 27 |
| GRO J[1] | ggggttttgg ggttttgggg ttttgggg | 28 |
| GRO K[1] | ttggggttgg ggttggggtt gggg | 29 |
| GRO L[1] | gggtgggtgg gtgggt | 30 |
| GRO M[1] | ggttttggtt ttggttttgg ttttgg | 31 |
| GRO N[2] | tttcctcctc ctccttctcc tcctcctcc | 32 |
| GRO O[2] | cctcctcctc cttctcctcc tcctcc | 33 |
| GRO P[2] | tggggt | 34 |
| GRO Q[2] | gcatgct | 35 |
| GRO R[2] | gcggtttgcg g | 36 |
| GRO S[2] | tagg | 37 |
| GRO T[2] | ggggttgggg tgtggggttg ggg | 38 |

[1]Indicates a good plasma membrane nucleolin-binding GRO.
[2]Indicates a nucleolin control (non-plasma membrane nucleolin binding).
[3]GRO sequence without [1] or [2] designations have some antiproliferative activity.

Any antibody that binds nucleolin may also be used. In certain instances, monoclonal antibodies are preferred as they bind single, specific and defined epitopes. In other instances, however, polyclonal antibodies capable of interacting with more than one epitope on nucleolin may be used. Many anti-nucleolin antibodies are commercially available, and are otherwise easily made. See, for example, US Patent Application Publication No. US 2013/0115674 to Sutkowski et al. Table 2 lists a few commercially available anti-nucleolin antibodies.

TABLE 2 commercially available anti-nucleolin antibodies

| Antibody | Source | Antigen source |
|---|---|---|
| p7-1A4 Mouse monoclonal antibody (mAb) | Developmental Studies Hybridoma Bank | *Xenopus laevis* oocytes |
| Sc-8031 mouse mAb | Santa Cruz Biotech | human |
| Sc-9893 goat polyclonal Ab (pAb) | Santa Cruz Biotech | human |
| Sc-9892 goat pAb | Santa Cruz Biotech | human |
| Clone 4E2 mouse mAb | MBL International | human |
| Clone 3G4B2 mouse mAb | Upstate Biotechnology | dog (MDCK cells) |
| Nucleolin, Human (mouse mAb) | MyBioSource | human |
| Purified anti-Nucleolin-Phospho, Thr76/Thr84 (mouse mAb) | BioLegend | human |
| Rabbit Polyclonal Nucleolin Antibody | Novus Biologicals | human |
| Nucleolin (NCL, C23, FLJ45706, FLJ59041, Protein C23) Mab Mo xHu | US Biological | human |
| Nucleolin (NCL, Nucl, C23, FLJ45706, Protein C23) Pab Rb xHu | US Biological | human |
| Mouse Anti-Human Nucleolin Phospho-Thr76/Thr84 Clone 10C7 mAb | Cell Sciences | human |
| Anti-NCL/Nucleolin (pAb) | LifeSpan Biosciences | human |
| NCL purified MaxPab mouse polyclonal antibody (B02P) | Abnova | human |
| NCL purified MaxPab rabbit polyclonal antibody (D01P) | Abnova | human |
| NCL monoclonal antibody, clone 10C7 (mouse mAb) | Abnova | human |
| Nucleolin Monoclonal Antibody (4E2) (mouse mAb) | Enzo Life Sciences | human |
| Nucleolin, Mouse Monoclonal Antibody | Life Technologies Corporation | human |
| NCL Antibody (Center E443) (rabbit pAb) | Abgent | human |
| Anti-Nucleolin, clone 3G4B2 (mouse mAb) | EMD Millipore | human |
| NCL (rabbit pAb) | Proteintech Group | human |
| Mouse Anti-Nucleolin Monoclonal Antibody, Unconjugated, Clone 3G4B20 | Active Motif | human |
| Nsr1p - mouse monoclonal | EnCor Biotechnology | human |
| Nucleolin (mouse mAb) | Thermo Scientific Pierce Products | human |
| Nucleolin [4E2] antibody (mouse mAb) | GeneTex | human |

Nucleolin targeting proteins are proteins, other than antibodies, that specifically and selectively bind nucleolin. Examples include ribosomal protein S3, tumor-homing F3 peptides [26, 27] and myosin H9 (a non-muscle myosin that binds cell surface nucleolin of endothelial cells in angiogenic vessels during tumorigenesis).

Anti-nucleolin agents may be conjugated to particles made of a variety of materials solid materials, including (1) metals and high molecular weigh elements; and (2) metal oxides. Metals and elements, preferably non-magnetic metals and elements, include gold, silver, palladium, iridium, platinum and alloys thereof. Oxides include zirconium dioxide, palladium oxide, barium sulfate, thorium oxide, uranium oxide and complex oxides thereof, such as barium titanate. Preferably, the particles are non-toxic. The particles are preferably nanoparticles having an average particle diameter of 1-100 nm, more preferably 1-50 nm, including 1, 2, 3, 4, 5, 10, 15, 20, 25, 30, 35, 40, 45, 50, 55, 60, 65, 70, 75, 80, 85, 90 and 95 nm.

Oligonucleotides and proteins have been attached to solid materials, such metals and elements, oxides, semiconductors and polymers, by a variety of techniques. These same techniques may be used to attach anti-nucleolin agents to particles. Further attachment of gadolinium complexes to the anti-nucleolin agent conjugated nanoparticles (conjugates), allows the conjugates to be used as MRI contrast agents, both in vivo and ex vivo.

Anti-nucleolin agent-conjugated nanoparticles may be used to formulate a pharmaceutical composition for radiosensitizers for treating cancer and tumors by RT, and targeting cancer cells expressing cell surface nucleolin, by forming mixtures of the anti-nucleolin agent conjugated nanoparticles and a pharmaceutically acceptable carrier, such as a pharmaceutical composition. Methods of treating cancer in a subject include administering a therapeutically effective amount of an anti-nucleolin agent conjugated nanoparticles followed by RT. The small size of nanoparticles allows nanoparticle conjugates to cross the blood-brain barrier, which enables imaging and treatment of brain tumors.

Particularly preferred compositions are aptamers conjugated to gold nanoparticles, and optionally further conjugated to gadolinium complexes. Gold nanoparticles (GNPs) exhibit low toxicity, versatile surface chemistry, light absorbing/scattering properties, and tunable size. Aptamers effectively cap gold particles and prevent aggregation, are safe, stable, easy to synthesize, and non-immunogenic. Aptamer conjugated GNPs offer improved efficacy of RT in vivo. Aptamer conjugated GNP are highly selective for cancer cells over normal cells, and when attached to cyanine dyes are excellent imaging agents, for example Cy2, Cy3, Cy5, Cy®5.5, Cy7, Alexa Fluor® 680, Alexa Fluor 750, IRDye® 680, and IRDye® 800CW (LI-COR Biosciences, Lincoln, Nebr.); and when attached to gadolinium complexes also act as MRI contrast agents specific for cancer cells. Aptamer conjugated GNP, and optionally attached to gadolinium complexes may be used as an imaging agent, MRI contrast agents, and may be administered as compositions which further contain a pharmaceutically acceptable carrier. The imaging agent may be administered to a subject in a method of imaging cancer in vivo, to form an image of the imaging agent present in the subject, by MRI.

The amounts and ratios of compositions described herein are all by weight, unless otherwise stated. Accordingly, the number of anti-nucleolin agents per nanoparticle may vary when the weight of the nanoparticle varies, even when the equivalent anti-nucleolin agent concentration (or equivalent aptamer concentration) is otherwise the same. For example, the number of anti-nucleolin agent molecules per nanoparticle may vary from 2 to 10,000, or 10 to 1000, including 20, 30, 40, 50, 60, 70, 80, 90, 100, 200, 300, 400, 500, 600, 700, 800 and 900.

A pharmaceutical composition is formulated to be compatible with its intended route of administration, including intravenous, intradermal, subcutaneous, oral, inhalation, transdermal, transmucosal, and rectal administration. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide.

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, CREMOPHOR EL® (BASF; Parsippany, N.J.) or phosphate buffered saline (PBS). In all cases, the composition must be sterile and should be fluid so as to be administered using a syringe. Such compositions should be stable during manufacture and storage and are preferably preserved against contamination from microorganisms such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can contain microorganism contamination. Isotonic agents such as sugars, polyalcohols, such as mannitol, sorbitol, and sodium chloride can be included in the composition. Compositions that can delay absorption include agents such as aluminum monostearate and gelatin.

Sterile injectable solutions can be prepared by incorporating the active agents, and other therapeutic components, in the required amount in an appropriate solvent with one or a combination of ingredients as required, followed by sterilization. Methods of preparation of sterile solids for the preparation of sterile injectable solutions include vacuum drying and freeze-drying to yield a solid.

Radiation treatment (RT) may be by any form of radiation, such as X-rays (for example megavolt energy X-rays), Brachy therapy, proton radiation, and neutron radiation. Also possible is to use doses and/or energy of RT that would normally be considered subclinical; because the anti-nucleolin agent-conjugated nanoparticles enhance the effectiveness of RT, the dosages are effective to kill or reduce the growth of cancer cells and tumors.

Anti-nucleolin agent-conjugated nanoparticles which contain gadolinium are effective MRI contrast agents, and may also be used to image cancer cells, including individual cancer cells. For example, the anti-nucleolin agent-conjugated nanoparticles which contain gadolinium may be administered to a patient to determine if cancer cells are present in lymph nodes, thus avoiding the removal of lymph node for the sole purpose of determining if they contain cancer cells. Another use can be to avoid the need for a biopsy. The anti-nucleolin agent-conjugated nanoparticles which contain gadolinium may be administered to a patient to determine if cancer is present in a lump, has metastasized to other location in the body, or to determine if all cancer from a tumor has been removed during surgery.

Anti-nucleolin agent-conjugated nanoparticles which optionally contain gadolinium are effective X-ray contrast agents, and may also be used to image cancer cells, including individual cancer cells. For example, the anti-nucleolin agent-conjugated nanoparticles which optionally contain gadolinium may be administered to a patient to determine if cancer cells are present in lymph nodes, thus avoiding the removal of lymph node for the sole purpose of determining if they contain cancer cells. Another use can be to avoid the need for a biopsy. The anti-nucleolin agent-conjugated nanoparticles which optionally contain gadolinium may be administered to a patient to determine if cancer is present in a lump, has metastasized to other location in the body, or to determine if all cancer from a tumor has been removed during surgery.

The pharmaceutical composition described herein may further comprise other therapeutically active compounds, and/or may be used in conjunction with physical techniques as noted herein which are suitable for the treatment of cancers and tumors. Examples of commonly used therapeutically active compounds include vinorelbine (Navelbine®), mytomycin, camptothecin, cyclyphosphamide (Cytoxin®), methotrexate, tamoxifen citrate, 5-fluorouracil, irinotecan, doxorubicin, flutamide, paclitaxel (Taxol®), docetaxel, vinblastine, imatinib mesylate (Gleevec®), anthracycline, letrozole, arsenic trioxide (Trisenox®), anastrozole, triptorelin pamoate, ozogamicin, irinotecan hydrochloride (Camptosar®), BCG live (Pacis®), leuprolide acetate implant (Viadur), bexarotene (Targretin®), exemestane (Aromasin®), topotecan hydrochloride (Hycamtin®), gemcitabine HCL (Gemzar®), daunorubicin hydrochloride (Daunorubicin HCL®), toremifene citrate (Fareston), carboplatin (Paraplatin®), cisplatin (Platinol® and Platinol-AQ®) oxaliplatin and any other platinum-containing oncology drug, trastuzumab (Herceptin®), lapatinib (Tykerb®), gefitinb (Iressa®), cetuximab (Erbitux®), panitumumab (Vectibix®), temsirolimus (Torisel®), everolimus (Afinitor®), vandetanib (Zactima™), vemurafenib (Zelboraf™), crizotinib (Xalkori®), vorinostat (Zolinza®), bevacizumab (Avastin®), hyperthermia, gene therapy and photodynamic therapy.

In the treatment of cancer, an appropriate dosage level of the therapeutic agent will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. The compounds may be administered on a regimen of 1 to 4 times per day, preferably once per day prior to RT. Administration by continuous infusion is also possible. All amounts and concentrations of anti-nucleolin oligonucleotide conjugated gold nanoparticles are based on the amount or concentration of anti-nucleolin oligonucleotide only.

Pharmaceutical preparation may be pre-packaged in ready-to-administer form, in amounts that correspond with a single dosage, appropriate for a single administration referred to as unit dosage form. Unit dosage forms can be enclosed in ampoules, disposable syringes or vials made of glass or plastic.

However, the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the patient undergoing therapy.

EXAMPLES

AS1411-linked gold nanoparticles for treating cancer and for cancer imaging were synthesized. Studies to assess the anticancer activity of AS1411 linked to 5 nm gold nanoparticles indicate that the conjugates have greatly enhanced antiproliferative effects on breast cancer cells compared to AS1411 (SEQ ID NO. 10) alone. Microscopic examination revealed increased uptake in breast cancer cells for GNP-AS1411 compared to GNP alone or GNP conjugated to a control oligonucleotide. In addition, GNP-AS1411 induced breast cancer cell vacuolization and death, similar to that seen at higher concentrations of AS1411. The GI50 values for AS1411 conjugated GNP against breast cancer cells are in the 50-250 nM range, compared to 1-10 uM range for unconjugated AS1411 (equivalent aptamer concentration). Studies indicate that these AS1411-GNPs have selective accumulation in tumor tissue following systemic administration in mice. Moreover, AS1411-GNPs retained the cancer-selectivity of AS1411 and had no effect on non-malignant cells.

Preparation of Aptamer Conjugated Gold Nanoparticles (GNP)

The aptamers AS1411 and CRO (the control oligonucleotide) with 5' prime thiol modification and or 3' fluorophore Cy5 were purchased from Integrated DNA Technologies (IDT).

```
AS1411 with thiol link at 5':
5'-/5ThioMC6-D/TTT TTT GGT GGT GGT GGT TGT GGT GGT
GGT GGT TT/-3'.

CRO with thiol link at 5':
5'-/5ThioMC6-D/TTT TTT CCT CCT CCT CCT TCT CCT CCT
CCT CCT TT/-3'.

AS1411 with thiol link at 5' and fluorophore Cy5
at 3':
5'-/5ThioMC6-D/TTT TTT GGT GGT GGT GGT TGT GGT GGT
GGT GGT TT/Cy5Sp/-3'.

CRO with thiol link at 5' fluorophore Cy5 at 3':
5'-/5ThioMC6-D/TTT TTT CCT CCT CCT CCT TCT CCT CCT
CCT CCT TT/Cy5Sp/-3'.
```

The thiol ends of aptamers were reduced by tri(2-carboxyethyl) phosphine TECP (50 mM) which is active in slightly acidic pH 6.5 of Tris-EDTA (10 mM) solution for 4-8 hours at room temperature. The solution of aptamers and TECP was purified using NAP-columns sephadex G-25. Accurate Spherical Gold nanoparticles 5 nm was purchased from NANOPARTZ and/or TED PELLA INC. The gold nanoparticles were filtered using 0.5 micron syringe filter. Gold nanoparticles and aptamers were mixed in the molar ratio of 1:40 in 25 ml RNAse and DNAse free water at room temperature overnight. Excess reagents were then removed by centrifugation at 15000 rpm for 20 min, followed by 3× wash with RNAse and DNAse free water and centrifugation to remove any unbound aptamers. To quantify the amount of aptamers conjugated on the nanoparticles surface, the aptamer conjugated GNP was incubated in 0.1M DTT at room temperature followed by the separation from the GNP by centrifugation. The supernatant was diluted and measured either spectrophotometically (A260 nm), then calculating the concentration from the aptamers standard dilution curve or by NanoDrop 2000 UV-VIS spectrophotometer. Similarly, the concentration of gold nanoparticles was calculated using spectrophotometric optical density (OD) at 511 nm and plotting the standard dilution curve to extrapolate the concentration of gold nanoparticles and the standard data provided by vendors.

Figure 1B:
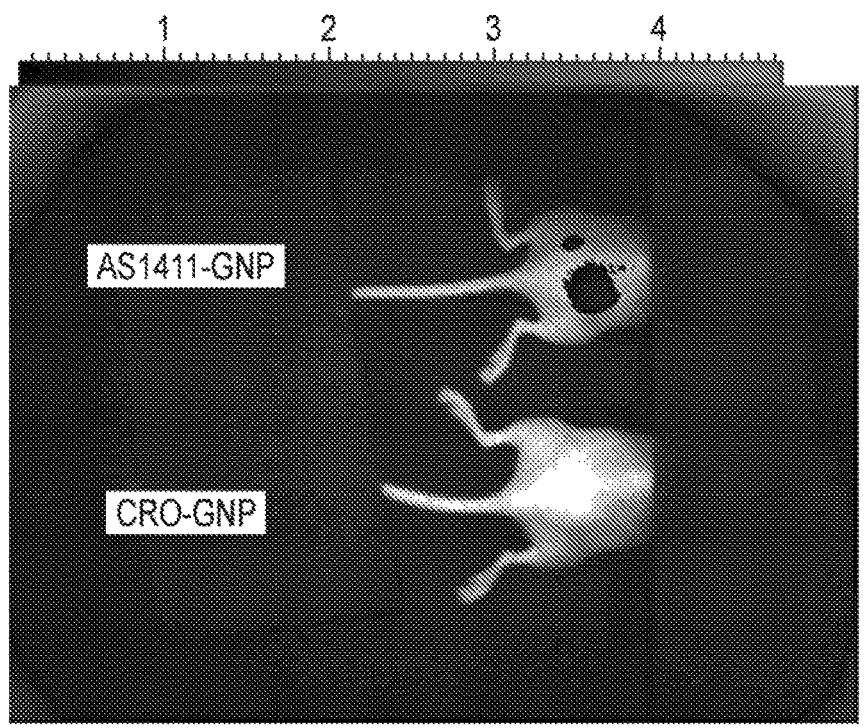

FIGS. 1A and 1B are images of two MDA231 xenograft mice (nude mice injected with MDA231 cancer cells), 2 hours (A) and 6 hours (B) after injection retro-orbitally with AS1411 conjugated with a fluorophor (cyanine dye Cy5) and gold nanoparticles (AS1411-Cy5-GNP), or with a control oligonucleotide conjugated with the fluorophor (cyanine dye Cy5) and gold nanoparticles (CRO-Cy5-GNP). The images were acquired using a PHOTON IMAGER™ at 680 nm. The images show that the tumors accumulate AS1411-Cy5-GNP, while CRO-Cy5-GNP is not accumulated.

Figure 2A:
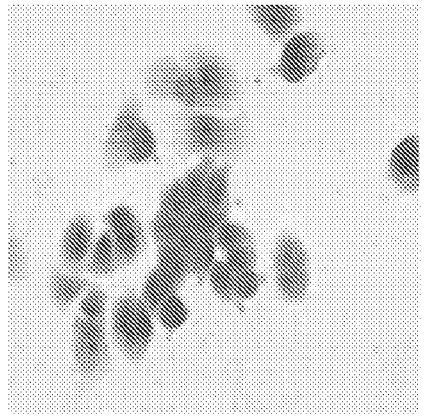
FIGS. 2A-D are optical micrographs of MCF7 cells treated by silver enhancement staining for gold nanoparticles, illustrating comparative accumulation of gold nanoparticles after administration of the indicated composition, or without administration.
Figure 2B:
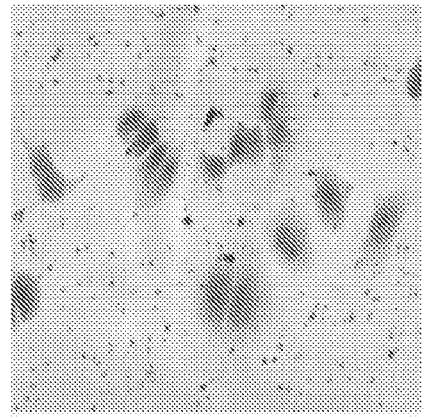
Figure 2C:
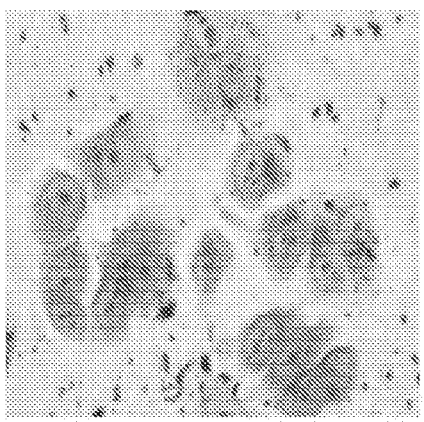
Figure 2D:
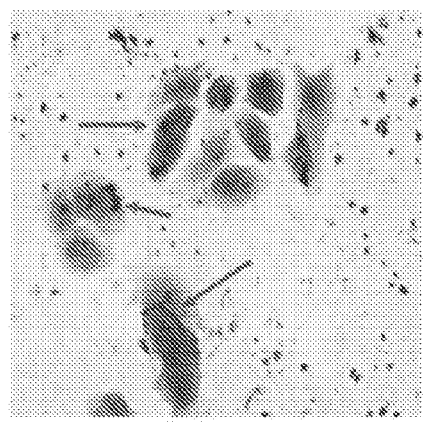

FIGS. 2A-D are optical micrographs of MCF7 cells treated by silver enhancement staining for gold nanoparticles, illustrating comparative accumulation of gold nanoparticles after administration of the indicated composition, or without administration. As shown, no significant accumulation occurs after administration of unconjugated gold nanoparticles (FIG. 2B), and only slight accumulation occurs after administration of control oligonucleotide-conjugated gold particles (FIG. 2C). Administration of AS1411-conjugated gold nanoparticles, however, results in significant accumulation of gold nanoparticles, as indicated by the arrows (FIG. 2D). Non-treated cells are also shown (FIG. 2A).

Comparison of Different Routes of Injection for Delivery of AS1411-GNP to Target Tissue Three different routes of injection for delivery of GNP-AS1411 to target tissue were tested: intraperitoneal, intravenous, via tail vein, retro-orbital, injection. Based on pilot studies, it was determined that for long term and repeated injections (as in therapeutic dosing), intraperitoneal injection was preferred for its convenience and because the slower biodistribution (compared to intravenous or retro-orbital) was not a concern. For imaging, either tail vein or retro-orbital injections were used because it delivered the drug directly into the blood, resulting in more rapid systemic distribution and avoiding residual signal in the peritoneum that was observed when delivering through the intraperitoneal route.

Effect of GNP Size and Linkers Length on Cell Proliferation

Syntheses and analyses of GNPs and linkers were performed as follows: colloid spherical gold nanoparticles of different size (5, 10, 15 nm) were purchased from Ted Pella Inc. (Redding, Calif.) and Nanopartz (Loveland, Colo.). Size analyses of these gold nanoparticles were confirmed using PARTICLES SIZE ANALYZER 90 PLUS (Brookhaven Instrument), and the sizes of gold nanoparticles were within the ranges as described by the manufacturers. Fluorophore (Cy5)-linked oligonucleotides (AS1411 and CRO), with or without carbon spacers and thiol groups, were purchased from Integrated DNA Technologies (San Diego, Calif.). Cy5, or cyanine-5 phosphoramidite [3-(4-monomethoxytritylozy)propyl]-1'-[3-[(2-cyanoethyl)-(N,N-diisopropyl) phosphorarmidityl]propyl]-3,3,3',3'-tetramethylindodicarbocyanine chloride) has the structure shown in Formula I:

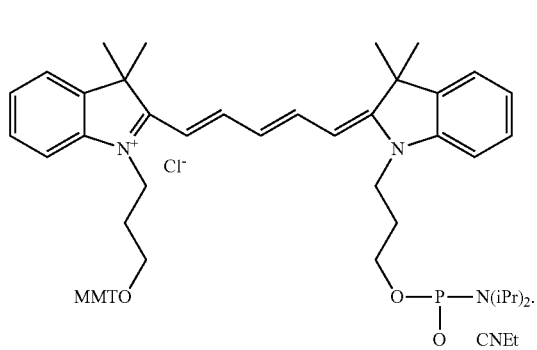

(I)

The linkers, C3-thiol (1-O-dimethoxytrityl-propyl-disulfide, 1'-succinyl-lcaa), MC6-D/iSP-9 (9-O-dimethoxytrityl-triethylene glycol, 1-[(2-cyanoethyl)-(N,N-diisopropyl)]), and MC6-D/iSP-18(18-O-dimethoxytritylhexaethylene glycol, 1-[(2-cyanoethyl)-(N,N-diisopropyl)]), have the structures shown in Formulas II, III and IV, respectively;

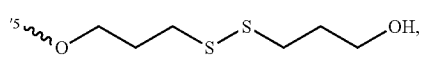

(II)

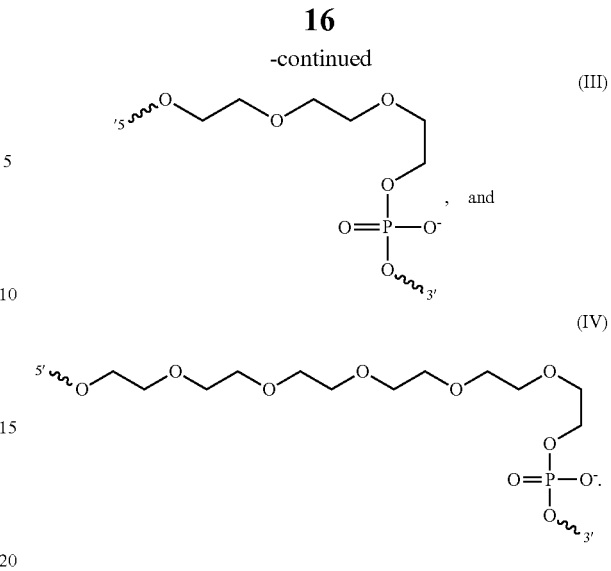

Figure 3A:
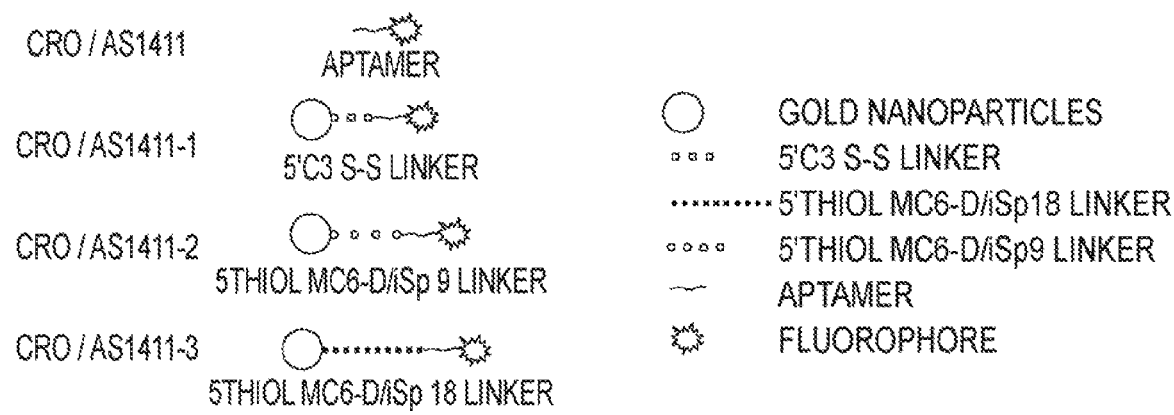
FIG. 3A is a sketch of different linkers used to conjugate AS1411/CRO to gold nanoparticles.
Figure 3B:
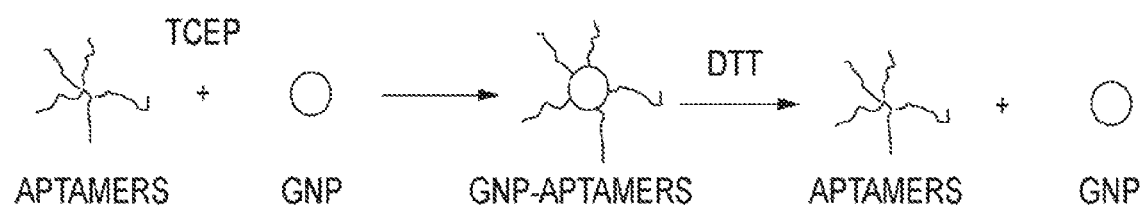
FIG. 3B is a sketch of attaching and detaching aptamers to gold nanoparticles.

FIG. 3A is a cartoon representation of the various agents tested. FIG. 3B is an illustration of the reaction to term conjugates, and to separate the parts of the conjugates, In Vivo Biodistribution of AS1411-GNP Conjugated to Fluorophore Cy5

Figure 4A:
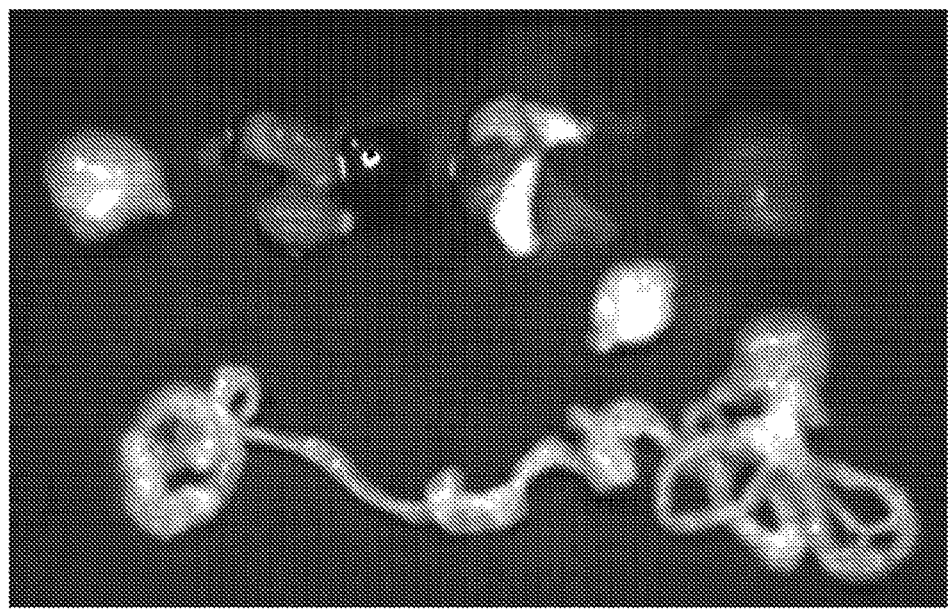
FIGS. 4A and B show the biodistribution of AS1411-GNP-Cy5: the mice were treated, euthanized and organs were photographed (A) and examined for fluorescence (B).
Figure 4B:
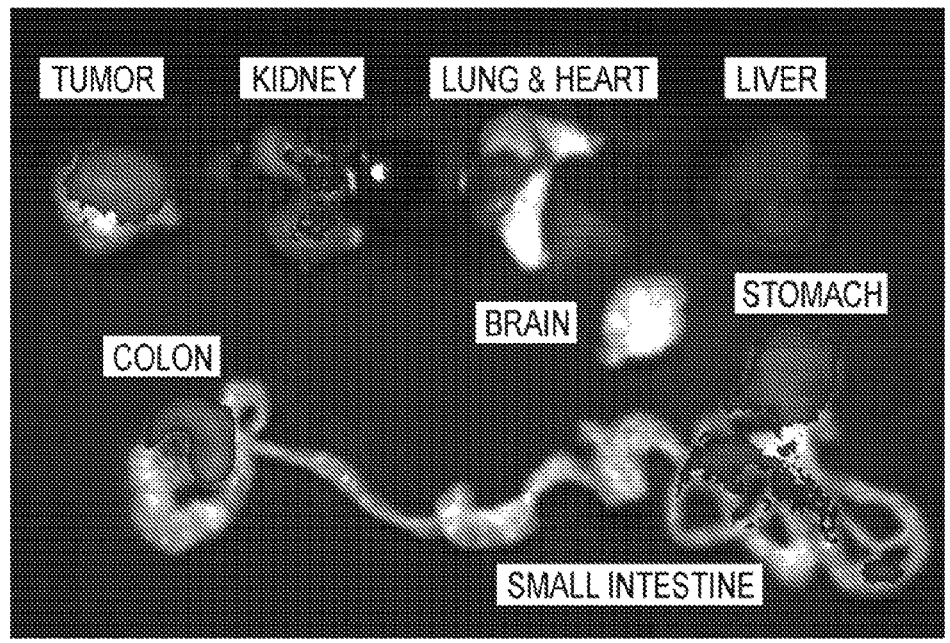

The use of multimodal imaging approaches utilizing optical and microCT was useful for detection of primary or disseminated breast cancer tumors. In this experiment a Cy5 fluorophore was linked to the 5'-end of AS1411 and conjugated to the GNP (to give GNP-AS1411-Cy5), in order to evaluate its utility as a complex not only for optical imaging but also as a contrast agent for computed tomography (CT). A similar construct with CRO was synthesized as a control. Nude mice with MDA-MB-231 breast cancer xenografts on each flank were administered a single injection of fluorophore-oligonucleotide-GNP. Images were acquired using IVIS Imaging System/MAESTRO Fluorescence Imaging and preliminary data showed that GNP-AS1411-Cy5 (1 mg/kg) concentration in the tumor is many times more than that using AS1411-Cy5 without GNP (10 mg/kg), or GNP-CRO-Cy5. It was noted that all mice exhibited strong signals on their extremities (legs and paws) and tails; these were artifacts from the urine and feces of the mice in cage where they were housed (possibly due to a fluorescent substance in the animal feed). Washing the mice and housing them in new clean new cages before imaging can prevent this problem. Biodistribution analysis also confirmed that, besides liver, kidney and intestine, most of the GNP-AS1411 accumulated in the tumor (FIG. 4). This is a proof of concept that conjugating AS1411 to gold nanoparticles can specifically target the tumors. Mice were treated by intraperitoneal injection with the indicated substances and were imaged after 96 h. Images showed high accumulation of GNP-AS1411-Cy5 (1 mg/kg aptamer concentration) in breast cancer xenograft, as compared to AS1411 (10 mg/Kg) and GNP-CRO alone.

Uptake Studies in MCF-7 Cells

Figure 5:
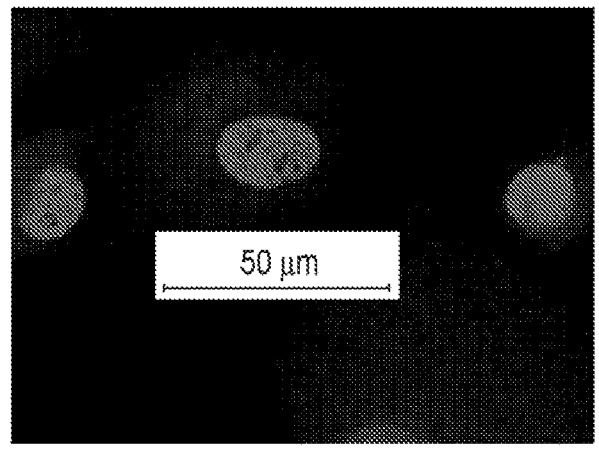
FIG. 5 illustrates the results of uptake studies in MCF-7 cells. Breast Cancer Cells (MCF-7) were treated with gold nanoparticles (GNP) conjugated with gadolinium-AS1411 or gadolinium-CRO and a linked fluorophore (Cy5) for 4 hrs. Confocal microscopy showing the uptake of the corresponding Oligo-Gd-GNP-Cy5 conjugate using Cy5 laser excitation (650 nm) and emission (670 nm) in MCF-7 cells.
Figure 5:
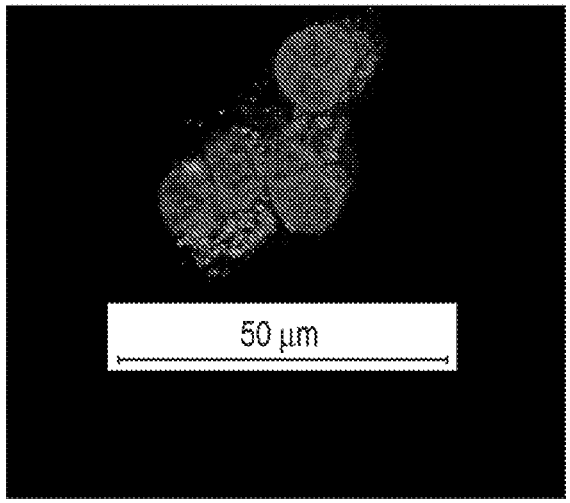
Figure 5:
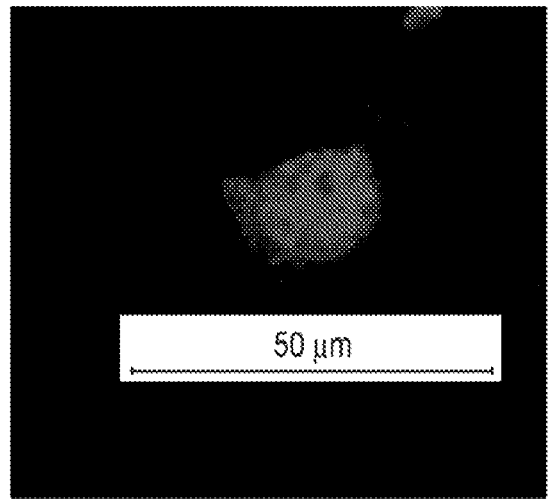

Breast Cancer Cells (MCF-7) were treated with gold nanoparticles (GNP) conjugated with gadolinium-AS1411 or gadolinium-CRO and a linked fluorophore (Cy5) for 4 hrs. Confocal microscopy showing the uptake of the corresponding Oligo-Gd-GNP-Cy5 conjugate using Cy5 laser excitation (650 nm) and emission (670 nm) in MCF-7 cells. The results are shown in FIG. 5.

Uptake Studies in MCF-10A Cells

Figure 6:
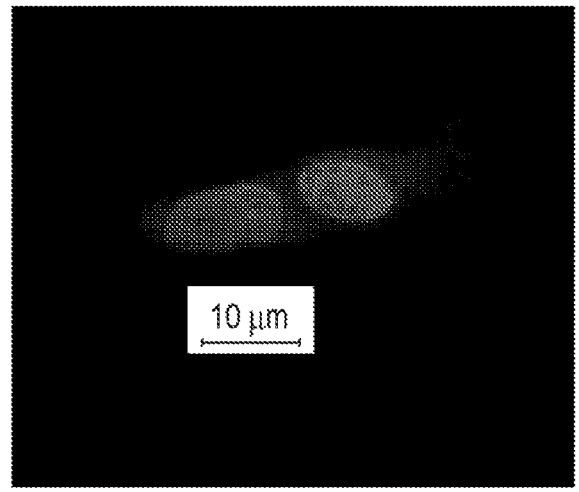
FIG. 6 illustrates the results of uptake studies in MCF-10A cells. Non-malignant Breast Epithelial Cells (MCF-10A) were treated with gold nanoparticles (GNP) conjugated with gadolinium-AS1411 or gadolinium-CRO and a linked fluorophore (Cy5) for 4 hrs. Confocal microscopy showing the uptake of the corresponding Oligo-Gd-GNP-Cy5 conjugate using Cy5 laser excitation (650 nm) and emission (670 nm) in MCF-10A cells.
Figure 6:
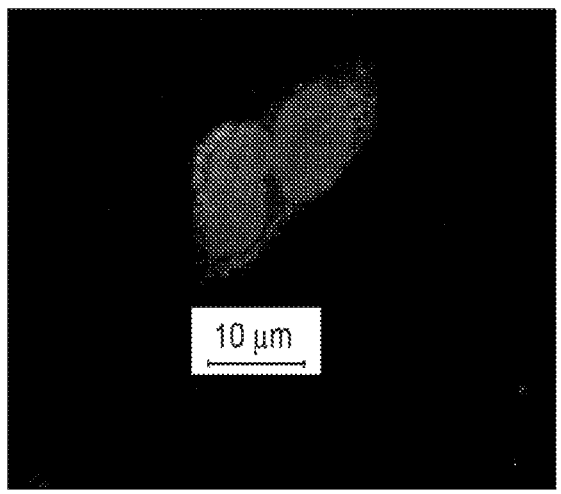
Figure 6:
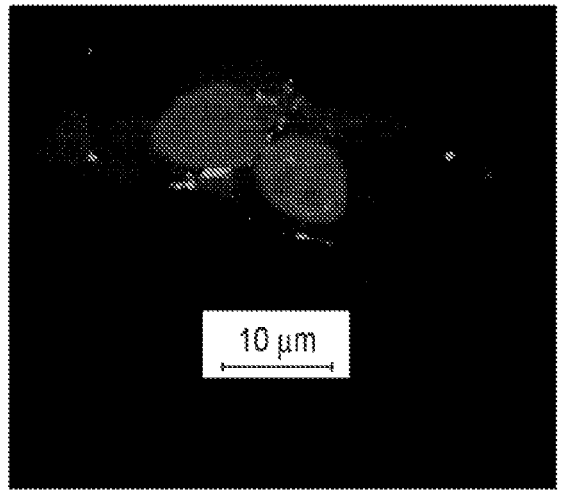

Non-malignant Breast Epithelial Cells (MCF-10A) were treated with gold nanoparticles (GNP) conjugated with gadolinium-AS1411 or gadolinium-CRO and a linked fluorophore (Cy5) for 4 hrs. Confocal microscopy showing the uptake of the corresponding Oligo-Gd-GNP-Cy5 conjugate using Cy5 laser excitation (650 nm) and emission (670 nm) in MCF-10A cells. The results are shown in FIG. 6.

DNA Damage Response

Figure 7A:
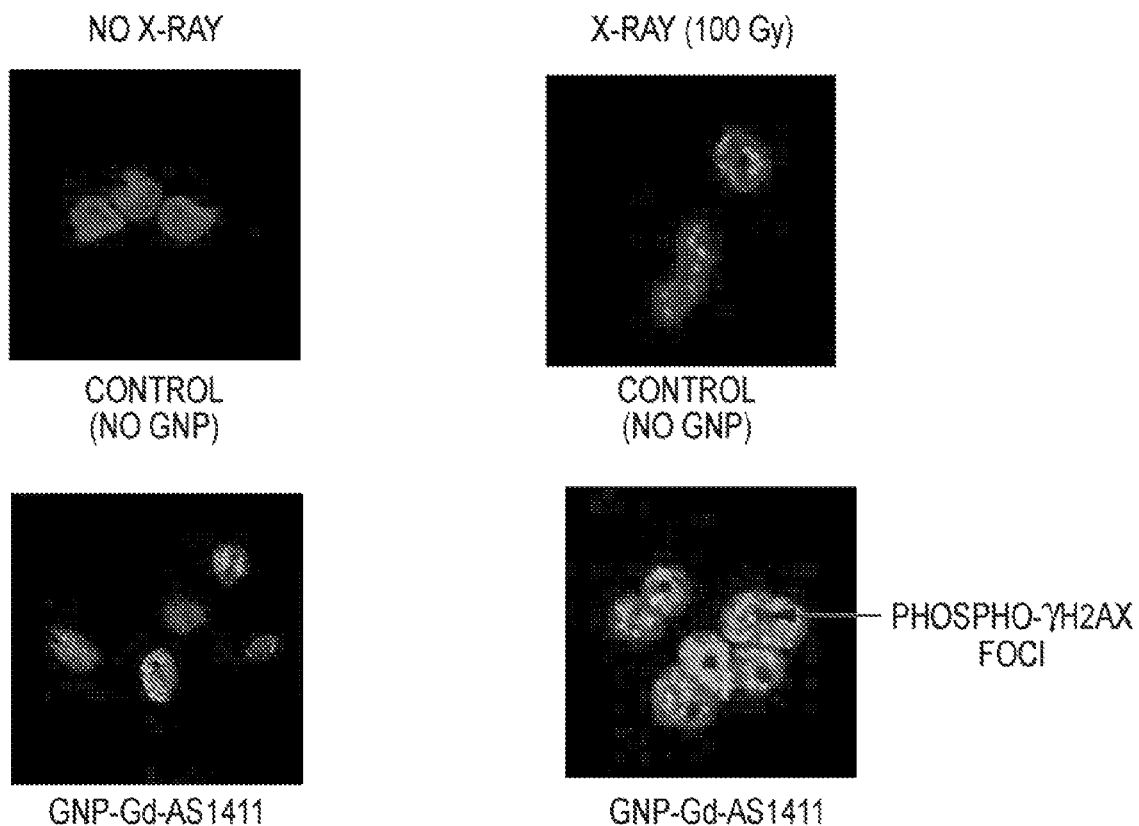
FIG. 7A illustrates confocal microscopy images of Breast Cancer Cells (MDA-MB-231) treated with gold nanoparticles (GNP) conjugated to gadolinium-AS1411 (GNP-Gd-AS1411) or AS1411 (GNP-AS1411) for 4 hrs, and treated with 100 cGy X-ray. DNA damage response marker phospho-γH2AX (red) foci was detected in the damage nuclei (blue) of MDA-MB-231 cells.
Figure 7B:
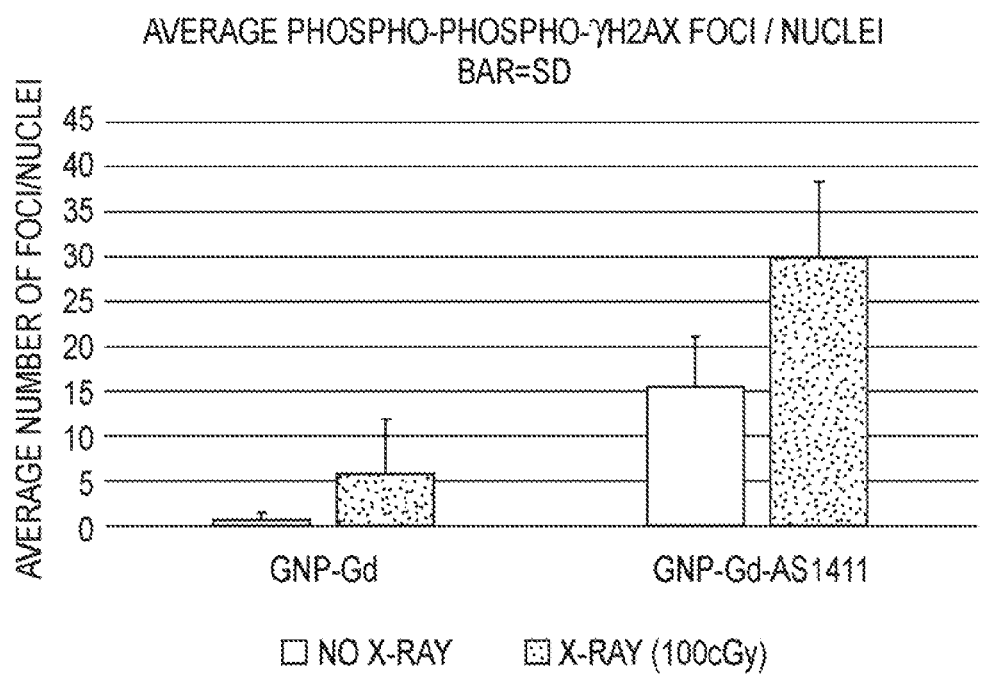
FIG. 7B is a graph illustrating the average foci per nuclei for Breast Cancer Cells (MDA-MB-231) treated with gold nanoparticles (GNP) conjugated to gadolinium-AS1411 (GNP-Gd-AS1411) or AS1411 (GNP-AS1411) for 4 hrs, and treated with 100 cGy X-ray, with bars indicating the standard deviation (SD).

Confocal Microscopy images are shown in FIG. 7. (A). Breast Cancer Cells (MDA-MB-231) were treated with gold nanoparticles (GNP) conjugated to gadolinium-AS1411 (GNP-Gd-AS1411) or AS1411 (GNP-AS1411) for 4 hrs, and treated with 100 cGy X-ray. DNA damage response marker phospho-γH2AX (red) foci was detected in the damage nuclei (blue) of MDA-MB-231 cells (B). Graph showing the average foci per nuclei, bars indicates standard deviation (SD).

Figure 12:
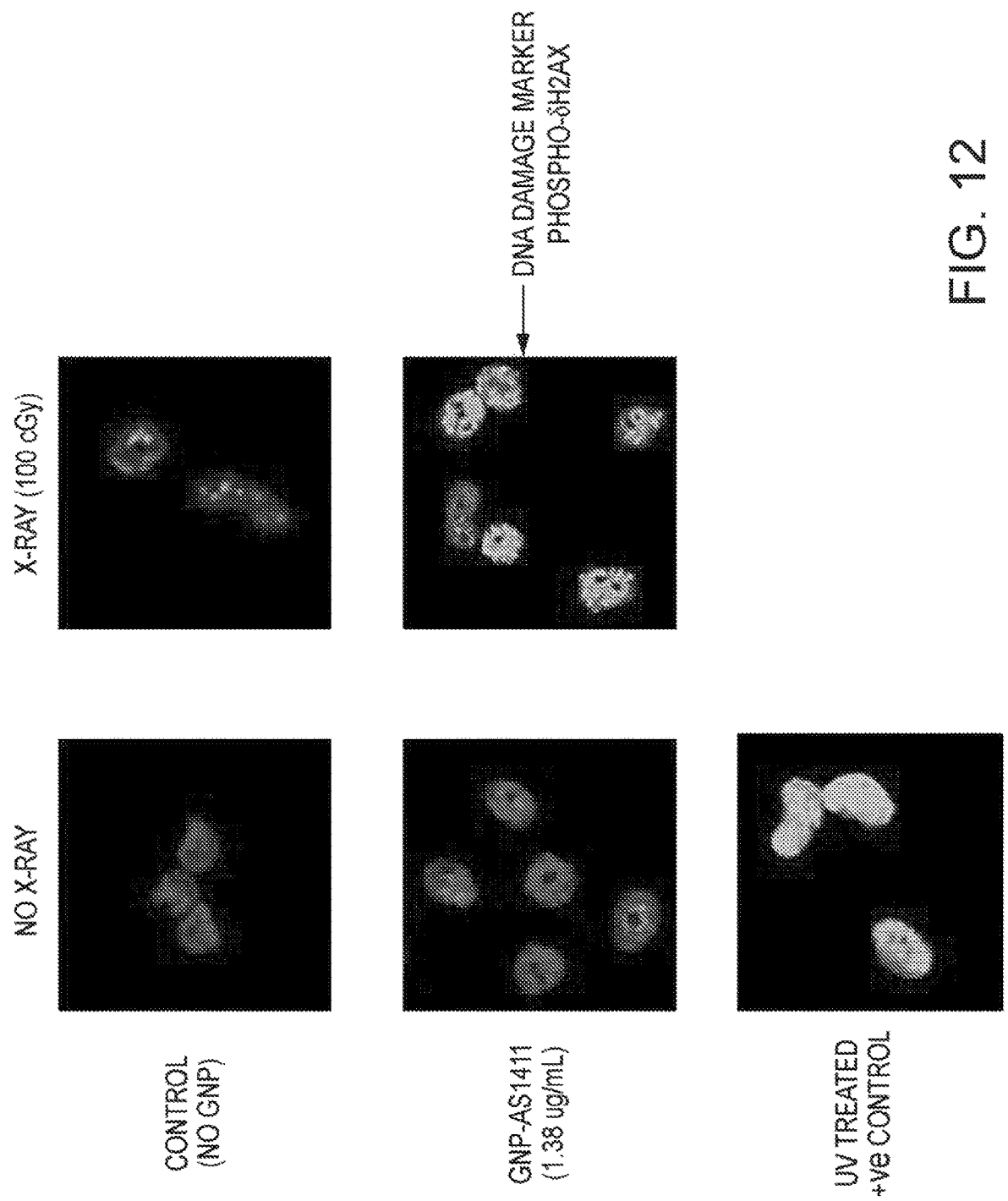
FIG. 12 illustrates confocal microscopy images of breast cancer cells treated with gold nanoparticles conjugated to AS1411 (GNP-AS1411).

Confocal microscopy images are shown in FIG. 12. Breast Cancer Cells (MDA-MB-231) were treated with 1.38 μg/mL gold nanoparticles (GNP) conjugated to AS1411 (GNP-AS1411) for 4 hrs, and treated with 100 cGy X-ray. DNA damage response marker phospho-γH2AX (Bethyl Laboratory) (red) foci was detected in the damage nuclei (blue) of MDA-MB-231 cells. A UV treated +ve control is also shown.

Clonogenic Assay of Breast Cancer Cells

Figure 8:
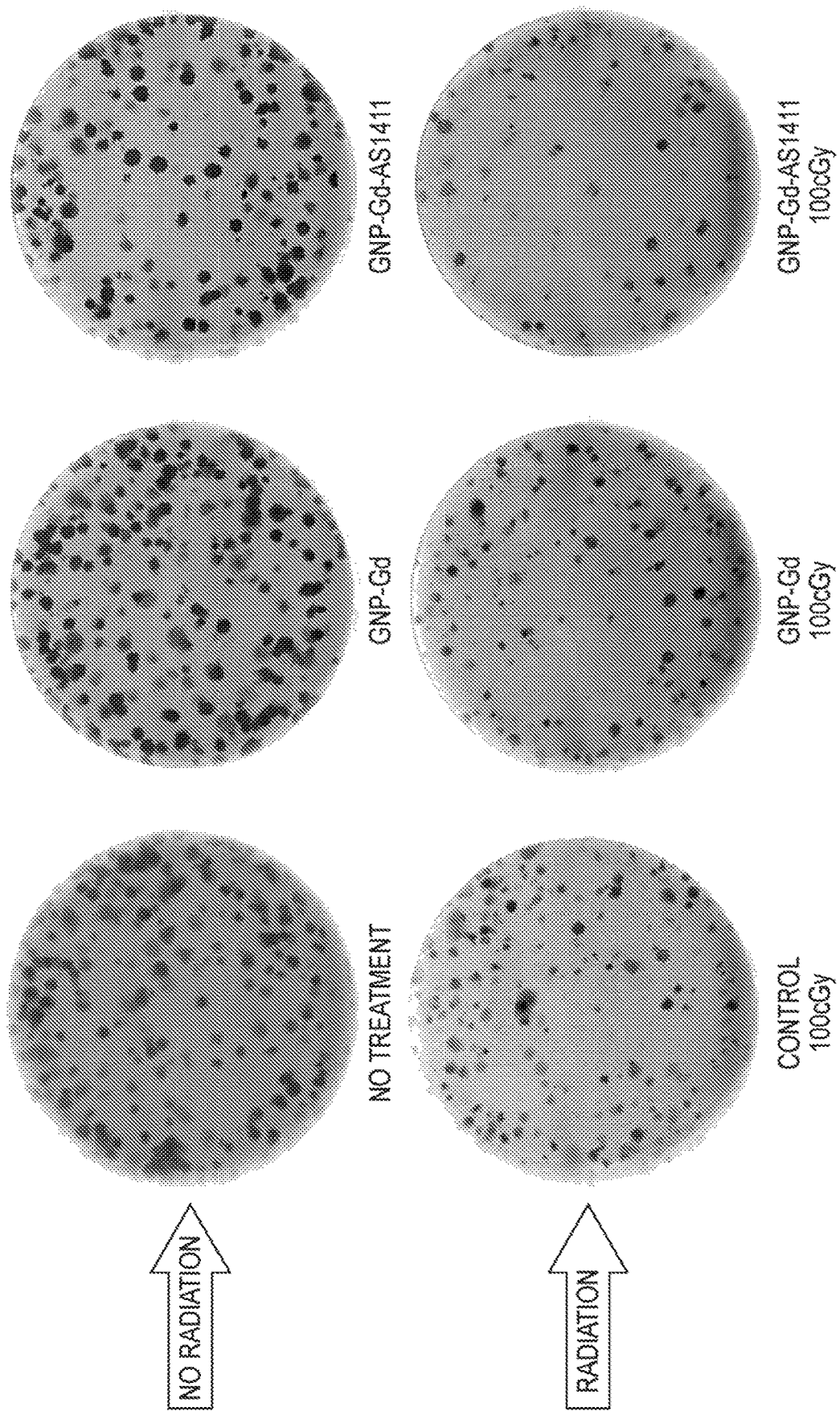
FIG. 8 illustrates Breast Cancer Cells (MDA-MB-231) plated in 35 mm dishes and treated with gold nanoparticle conjugated to gadolinium and AS1411 (0.03 mg/ml gold concentration). After 4 hrs dishes were radiated using X-Rad160/225 radiator at 100 cGy. Dishes were further incubated for 10 days. After incubation the colonies fix with 4% paraformaldehyde in phosphate buffer saline (PBS) and stained with 0.4% crystal violet.
Figure 9A:
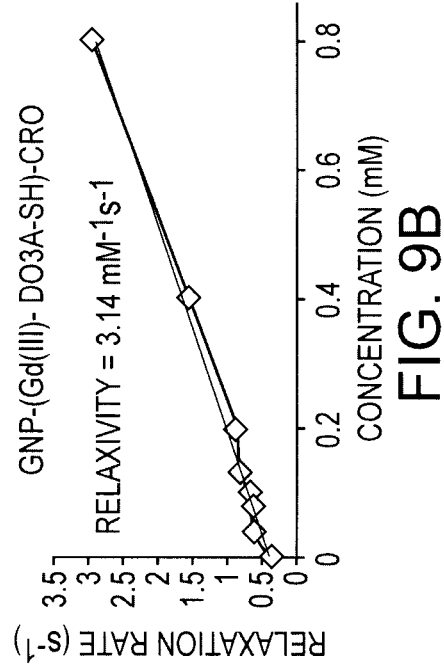
FIG. 9A illustrates the results of relaxivity analysis at 9.4 T for Gold nanoparticles coated with AS1411 and Gd(III)-DO3A-SH (1B).
Figure 9B:
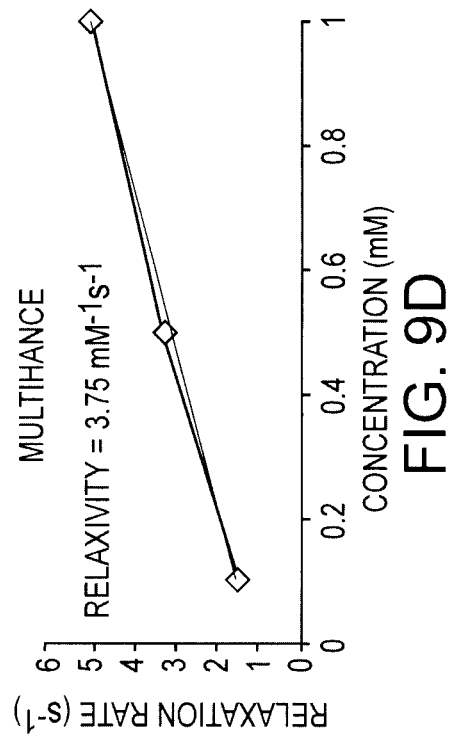
FIG. 9B illustrates the results of relaxivity analysis at 9.4 T for Gold nanoparticles coated with CRO (control) and Gd(III)-DO3A-SH.
Figure 9C:
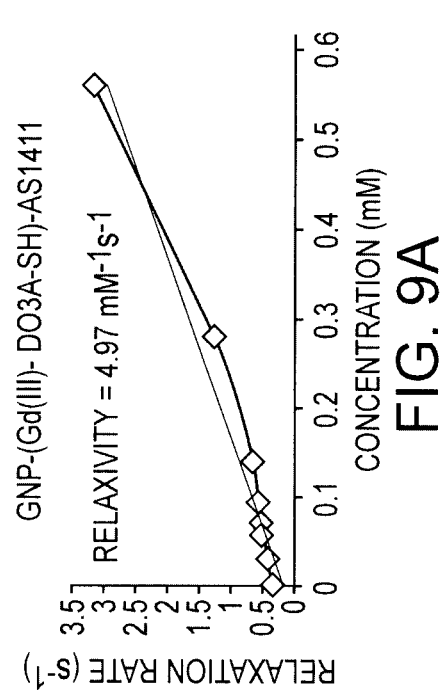
FIG. 9C illustrates the results of relaxivity analysis at 9.4 T for Gold nanoparticles coated with Gd(III)-DO3A-SH.
Figure 9D:
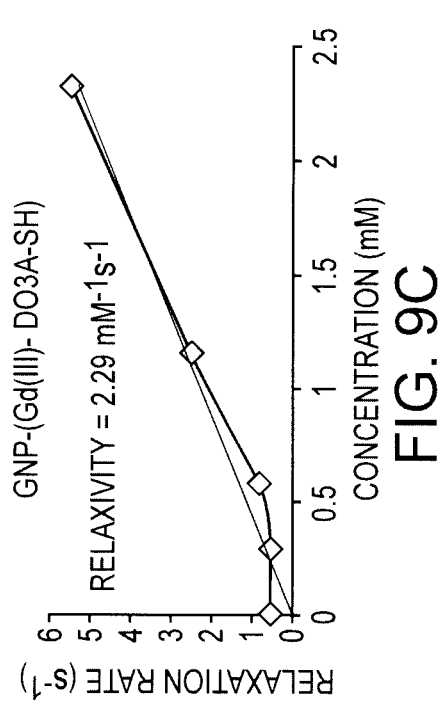
FIG. 9D illustrates the results of relaxivity analysis at 9.4 T for Gold nanoparticles coated with MULTIHANCE® (gadobenate dimeglumine).
Figure 9E:
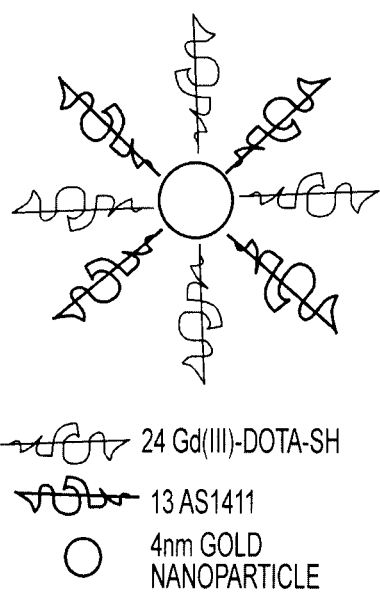
FIG. 9E illustrates a gold Nanoparticle coated with 24 Gd(III)-DO3A-SH and 13 AS1411/CRO.

Breast Cancer Cells (MDA-MB-231) were plated in 35 mm dishes and treated with gold nanoparticle conjugated to gadolinium and AS1411 (0.03 mg/ml gold concentration). After 4 hrs dishes were radiated using X-Rad160/225 radiator at 100 cGy. Dishes were further incubated for 10 days. After incubation the colonies fix with 4% paraformaldehyde in phosphate buffer saline (PBS) and stained with 0.4% crystal violet. The results are shown in FIG. 8.

Relaxivity Analysis

FIG. 9 shows the results of the relaxivity analysis at 9.4 T for: (1A) Gold nanoparticles coated with AS1411 and Gd(III)-DO3A-SH (1B) Gold nanoparticles coated with CRO (control) and Gd(III)-DO3A-SH (1C) Gd(III)-DO3A-SH (1D) MULTIHANCE® (gadobenate dimeglumine). Gold Nanoparticle coated with 24 Gd(III)-DO3A-SH and 13 AS1411/CRO (Middle).

Gadolinium-Functionalized Gold Nanoparticle CT/MRI Contrast Agent with Cancer Targeting Capabilities Gold nanoparticles (GNP) provide contrast in computed tomography (CT) images and other X-ray based imaging techniques due to their high atomic mass, and may be modified with bioactive coatings to increase their functionality. We have tailored spherical GNPs (~4 nm) with a T1 gadolinium-based magnetic resonance imaging (MRI) contrast agent (Gd(III)-DO3A-SH) and therapeutic/cancer-targeting DNA aptamer (AS1411) for cancer imaging and therapy. GNP coated with Gd(III)-DO3A-SH and AS1411 or CRO had hydrodynamic diameters of 13.45±2.11 and 19.01±2.51 nm, respectively, and zeta potentials of −13.83±0.74 and −52.62±1.01 mV. Both solutions were stable for more than 6 months in physiological buffer solutions. EDAX analysis of GNP-Gd(III)-DO3A-AS1411 and GNP Gd(III)-DO3A-CRO yielded 28±5 and 23±4 Gd centers per GNP, respectively, compared to 15±1 Gd centers per GNP for GNP-Gd(III)-DO3A solutions. AS1411 was detected on the gold nanoparticle surface using Quant-iT™ OliGreen® ssDNA reagent via fluorescence imaging studies on purified samples of GNP Gd(III)-DO3A-AS1411, GNP-Gd(III)-DO3A and GNP-AS1411.

The GNP-Gd(III)-DO3A-AS1411/CRO probes have been assessed for their efficacy as CT and/or MRI contrast agents. At both 9.4 and 3.0 Tesla, solutions of GNP-Gd(III)-DO3A-SH-AS1411 and GNP-Gd(III)-DO3A-SH-CRO generate higher relaxivity than GNP-Gd(III)-DO3A, industry standard MULTIHANCE® (gadobenate dimeglumine) or Gd(III)-DO3A-SH, Table 3. In CT scans, solutions of GNP-Gd(III)-DO3A-AS1411 and GNP-Gd(III)-DO3A-CRO yield significantly higher X-Ray attenuation (Hounsefield unit per milligram milliliter) values in comparison to Iopamidol, GNP-Gd(III)-DO3A and citrate capped gold, Table 3.

TABLE 3

Relaxivity and X-ray attenuation data

| Samples | Relaxivity (mM$^{-1}$s$^{-1}$) at 9.4 T | Relaxivity (mM$^{-1}$s$^{-1}$) at 3.0 T | Hounsefield Unit (HU) mg$^{-1}$ ml |
|---|---|---|---|
| GNP-(Gd(III) DO3A SH)-AS1411 | 24.83 | 27.51 | 227.46 |
| GNP-(Gd(III) DO3A SH)-CRO | 15.67 | 31.61 | 250.66 |
| GNP-(Gd(III) DO3A SH) | 5.56 | — | 81.53 |
| Gd(III) DO3A SH | 2.29 | — | — |
| MULTIHANCE® (gadobenate dimeglumine) | 3.75 | — | — |
| GNP AS1411 | — | — | 83.03 |
| GNP CRO | — | — | 113.47 |
| GNP Citrate Capped | — | — | 92.47 |
| Iopamidol | — | — | 71.07 |

CT Contrast

Figures 10A, 10B:
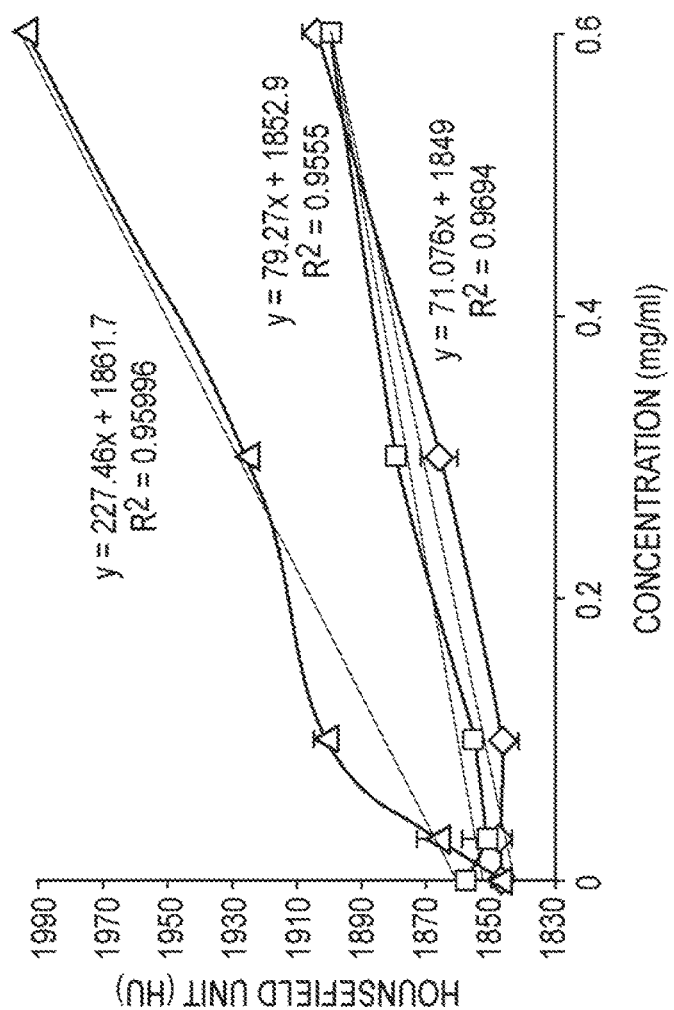
FIG. 10A illustrates X-ray attenuation intensities in Hounsfield Unit (HU) as a function of GNP concentrations for GNS/Gd(III)-DOTA-SH/AS1411 construct (green), GNP/AS1411 (red), and Iopamidol (blue).
FIG. 10B illustrates a table of X-ray attenuation intensities in Hounsfield Unit (HU) for various constructs.

The Hounsfield unit is a normalized index of x-ray attenuation ranging from −1000 (air) to +1000 (bone) with water being 0 and is used in CT imaging to evaluate contrast. We have performed 5 microCT studies using a MicroCAT-II (Siemens, Knoxville, Tenn.) to evaluate various conjugated gold nanospheres. The images acquired at 45 kVp and 80 kVp were observed on the ImageJ software and a mean of five ROI (region of interest) values is obtained for the attenuation values in Hounsfield Unit (HU). The solution of GNS-DO3A-Gd3+ decorated with AS1411 yielded a higher magnitude of X-ray attenuation intensities and Hounsfield units per milligram milliliter (slope) values in comparison to equivalent amounts of the industry standard (Iopamidol) or citrate-capped gold nanoparticles (FIGS. 10A & 10B). In general, the attenuation intensities increase with gold nanoparticle concentration and therefore the GNP-Gd(III)-DO3A-SH-Oligo probes can be used as an contrast agent for CT imaging modality.

Clonogenic Assay of Lung Cancer Cells

Figure 11A:
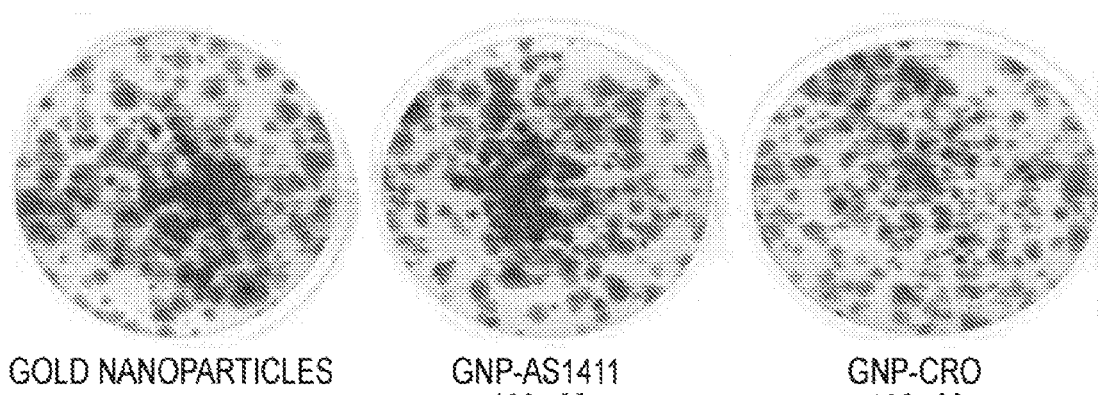
FIG. 11A illustrates lung cancer cells treated with gold nanoparticles and gold nanoparticle-aptamer conjugates without exposure to X-ray radiation.
Figure 11B:
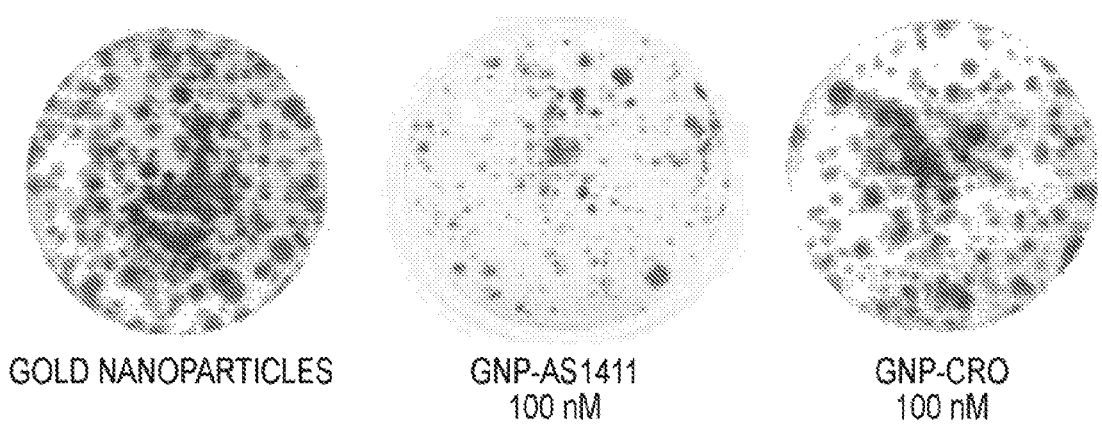
FIG. 11B illustrates treated lung cancer cells with exposure to X-ray radiation.
Figure 11C:
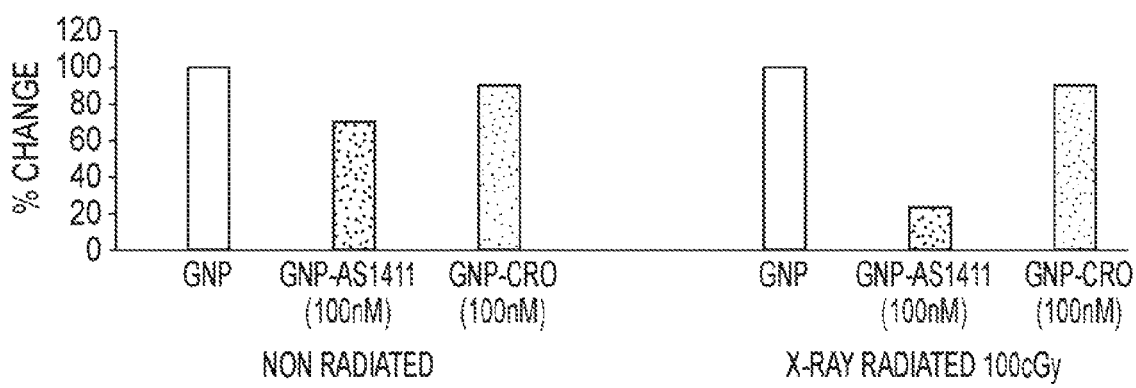
FIG. 11C is a graph illustrating the percent change in absorbance of the cells with and without exposure to X-ray radiation.

Lung cancer cells (A549) were treated with gold nanoparticles (GNP), 100 nM gold nanoparticle-control aptamer conjugates (GNP-CRO) and 100 nM gold-nanoparticle-AS1411 conjugates (GNP-AS1411). After 36 hours, the cells were exposed to 100 cGy X-ray radiation. The cells were further incubated for 7 days and fixed with 4% formalin and stained with 0.4% crystal violet solution. Colonies were de-stained with 10% acetic acid and absorbance was measured at 570 nm. FIG. 11A shows treated lung cancer cells before exposure to radiation. FIG. 11B shows treated lung cancer cells after exposure to radiation. FIG. 11C is a graph illustrating the percent change in absorbance (after de-staining with 10% acetic acid) of the cells before and after exposure to radiation. The results indicate that the AS1411 conjugates enhance the effects of radiation on lung cancer cells.

Concentration Study in Breast Cancer Cells

Figure 13A:
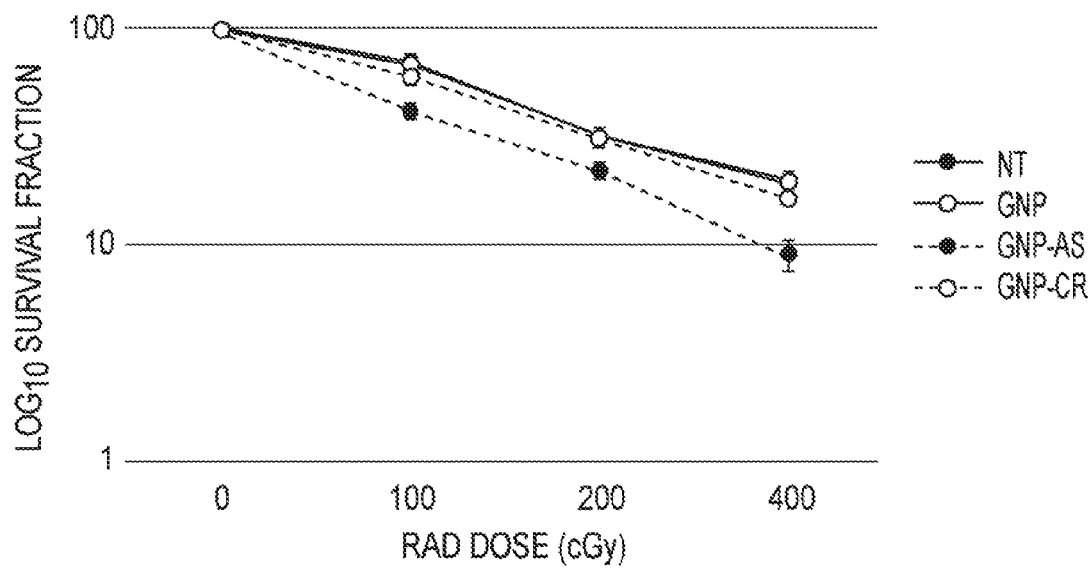
FIG. 13A illustrates the breast cancer cell survival fraction after treatment with 1.38 μg/mL gold nanoparticles and gold nanoparticle-aptamer conjugates.
Figure 13B:
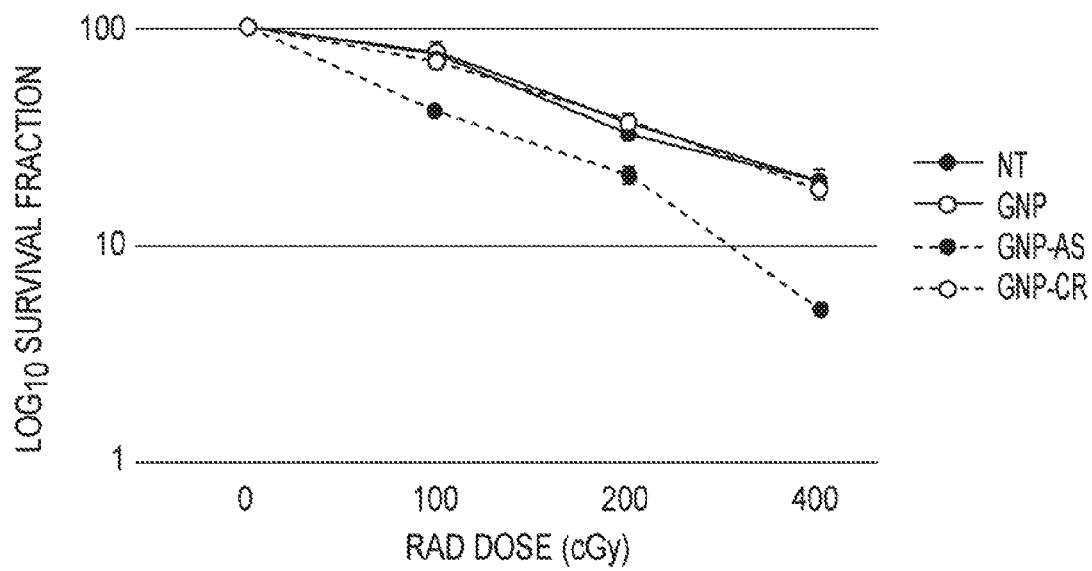
FIG. 13B illustrates the cancer cell survival fraction after treatment with 2.76 μg/mL gold nanoparticles and gold nanoparticle-aptamer conjugates.
Figure 13C:
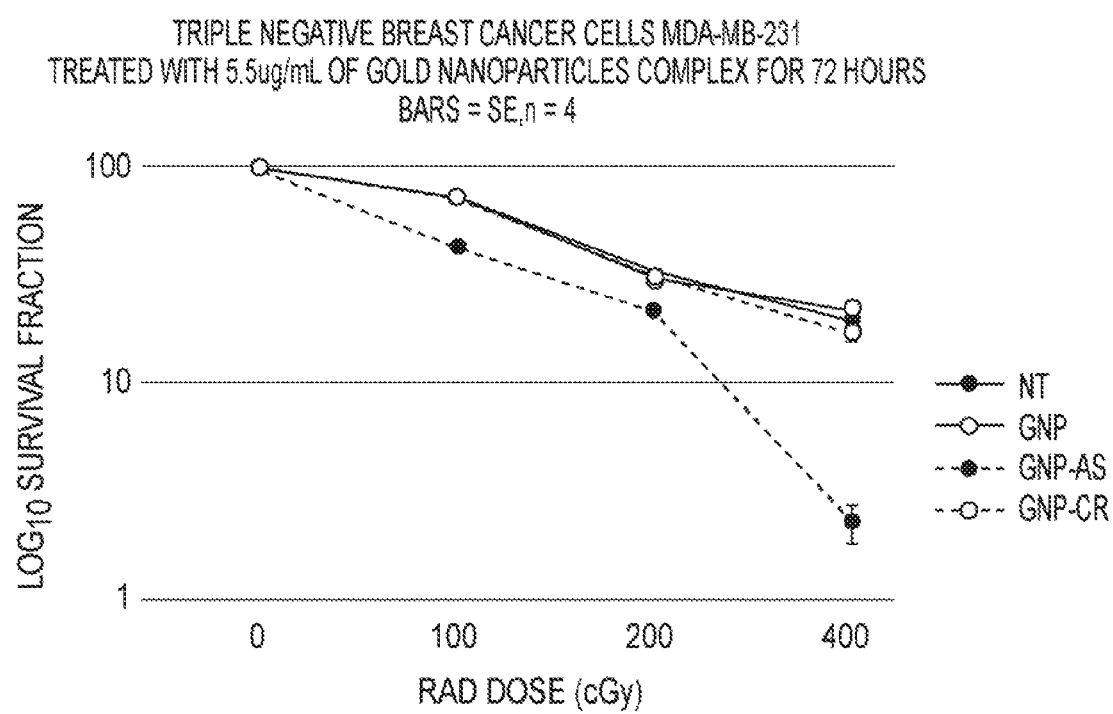
FIG. 13C illustrates the cancer cell survival fraction after treatment with 5.5 μg/mL gold nanoparticles and gold nanoparticle-aptamer conjugates.

Triple negative breast cancer cells (MDA-MB-231) were treated with varying concentrations of gold nanoparticles (GNP), gold nanoparticle-control oligonucleotide conjugates (GNP-CRO) and gold-nanoparticle-AS1411 conjugates (GNP-AS1411) for 72 hours. X-ray radiation was then applied to the cells. The $Log_{10}$ Survival Fraction of the cells after treatment and application of varying doses of X-ray radiation (cGy) was plotted. FIG. 13A shows the cancer cell survival fraction at 1.38 µg/mL. FIG. 13B shows the cancer cell survival fraction at 2.76 µg/mL. FIG. 13C shows the cancer cell survival fraction at 5.5 µg/mL. The results indicate that GNP-AS1411 conjugates become more effective at killing cancer cells at increasing concentrations.

Clonogenic Survival Assay of Breast Cancer Cells

Figure 14A:
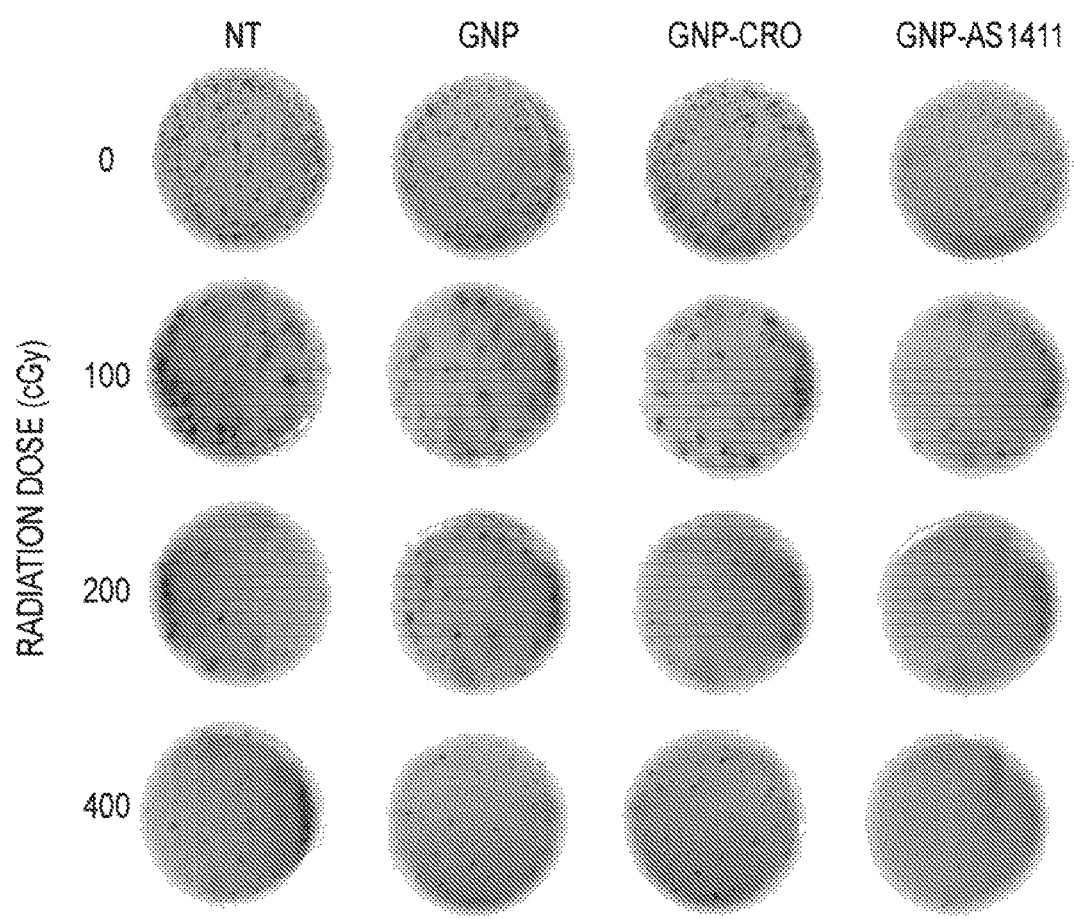
FIG. 14A illustrates breast cancer cells treated with gold nanoparticles and gold nanoparticle-aptamer conjugates.
Figure 14B:
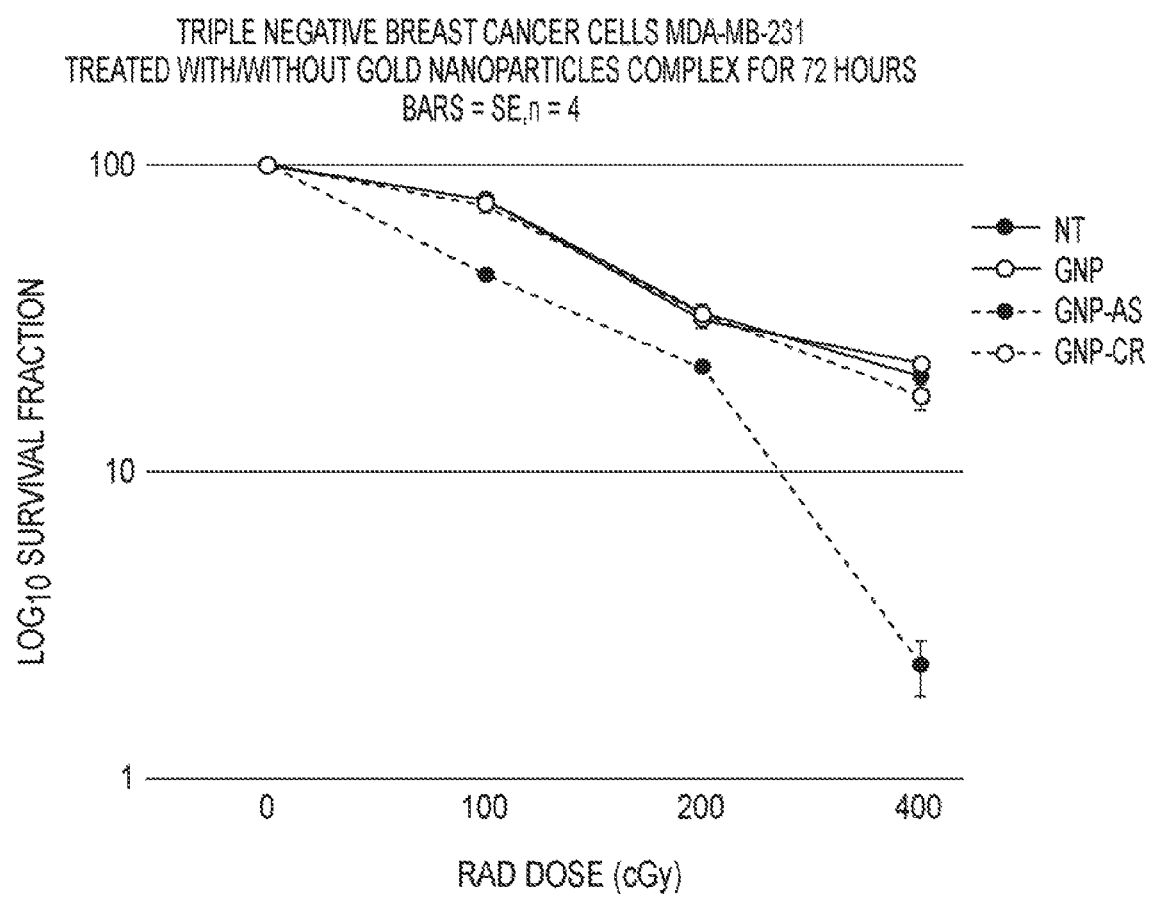
FIG. 14B is a graph illustrating the survival fraction of the cells.

Breast cancer cells (MDA-MB-231) were treated with gold nanoparticles (GNP), gold nanoparticle-control oligonucleotide conjugates (GNP-CRO) and gold-nanoparticle-AS1411 conjugates (GNP-AS1411) for 72 hours. The cells were washed in PBS and radiated at varying doses of γ-rays using a GammaCell-40 irradiator. The cells were trypsinized, counted and plated in six well plates for an additional 10 days. After incubation, the cells were fixed with methanol and stained with 2% crystal violet. The cells were counted and plotted for survival fraction as a function of radiation dose after exposure to γ-radiation. The results of the radiation treatment are shown in FIG. 14A. The $Log_{10}$ Survival Fraction of the cells versus the X-ray radiation dose in cGy is shown in FIG. 14B. The results indicate that the AS1411 conjugates enhance the effects of radiation on breast cancer cells.

Figure 15A:
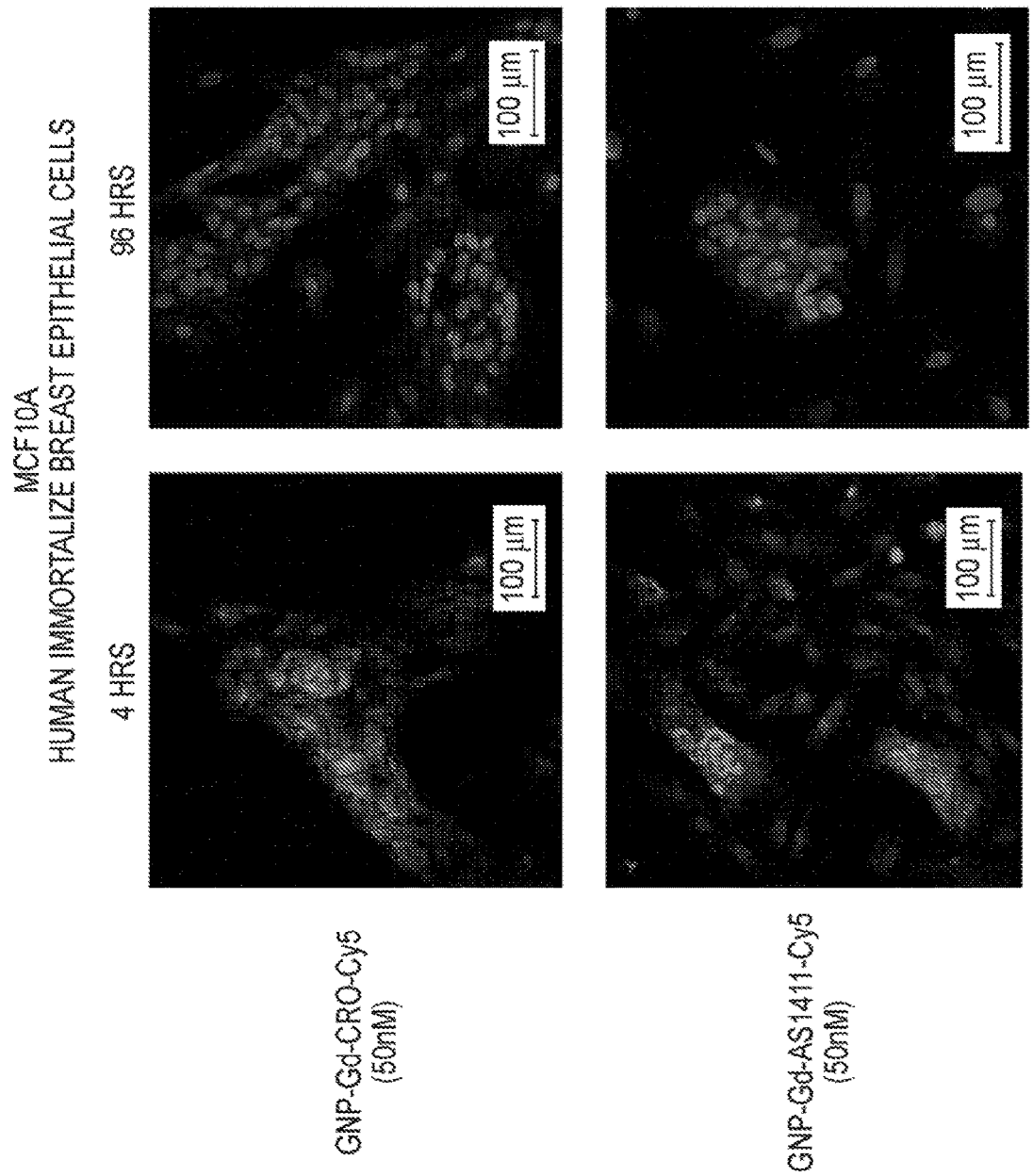
FIG. 15A illustrates uptake of fluorescent-labeled gold nanoparticle-gadolinium-oligomer conjugates in non-malignant breast cells.
Figure 15B:
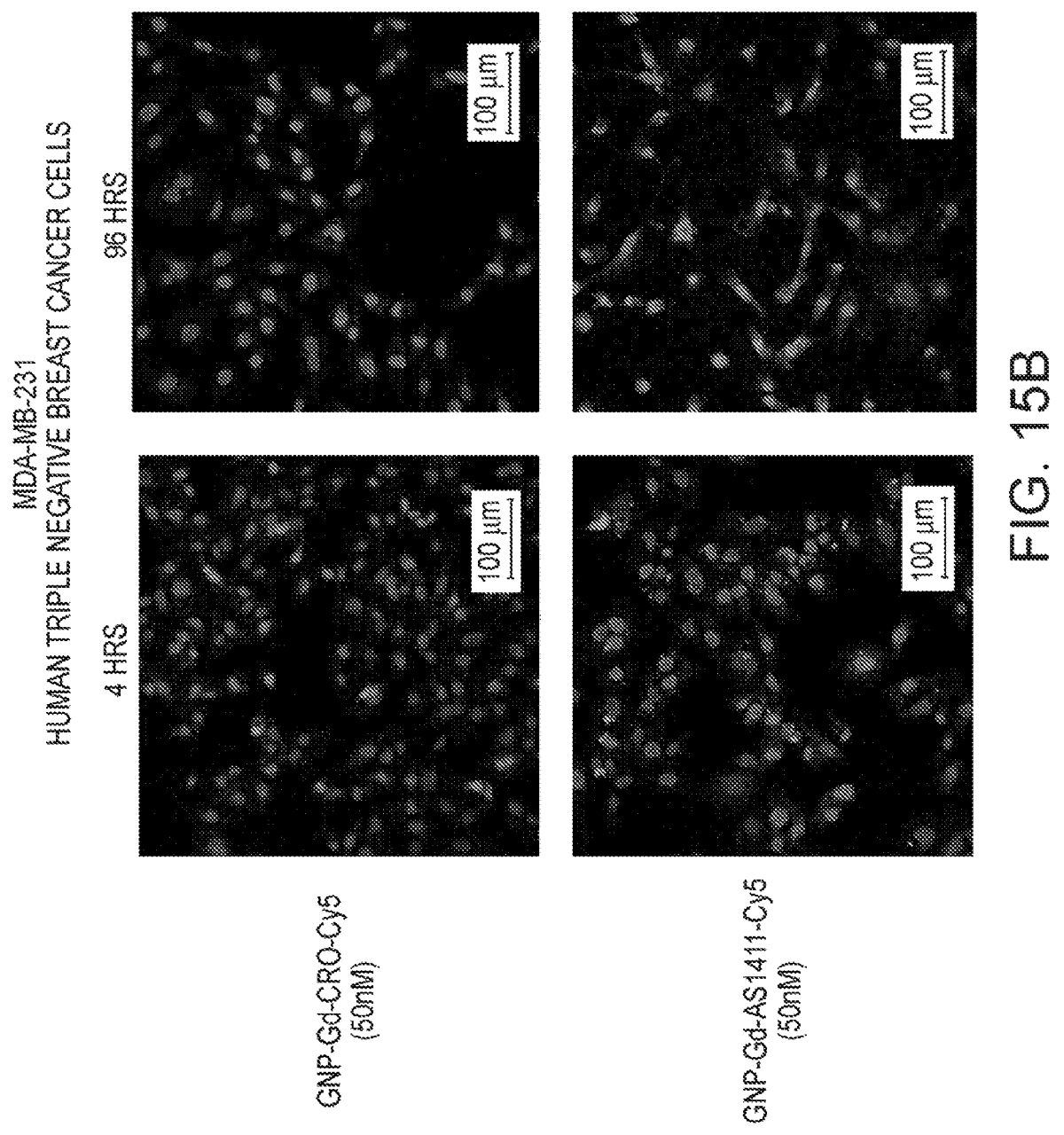

Selective Retention of Gold Nanoparticle-Gadolinium-Oligomer Conjugates in Malignant Cells Human immortalized breast epithelial cells (MCF10A) (non-malignant) and triple negative breast cancer cells (MDA-MB-231) were incubated with of fluorescent-labeled gold nanoparticle-gadolinium-oligomer conjugates for 4 and 96 hours. The cells were incubated with 50 nM GNP-Gd-CRO-Cy5 (control oligomer) or 50 nM GNP-Gd-AS1411-Cy5 using DO3A (1,4,7-tris(carboxymethyl)-1,4,7,10-tetraazacyclododecane) as the ligand to bind Gd and connect it to the GNP surface through a thiol linker. After incubation, the cells were harvested and washed with PBS (2×), counted using a TC-10 Cell Counter (Bio-Rad), plated in a 4 chamber slide (Bio-Tek) at 1,000 cells/well and incubated for an additional 24 hours. The cells were stained with nuclear stain DAPI after incubation and the complete DMEM media was replaced with DMEM without phenol red. Images were acquired using a NIKON® confocal microscope. FIG. 15A shows uptake in non-malignant breast cells. FIG. 15B shows uptake and selective retention of GNP-Gd-AS1411-Cy5 in malignant breast cancer cells at the 96 hours timepoint. The fluorescent-labeled GNP conjugates appear red and the nuclear stain appears blue.

Figure 16A:
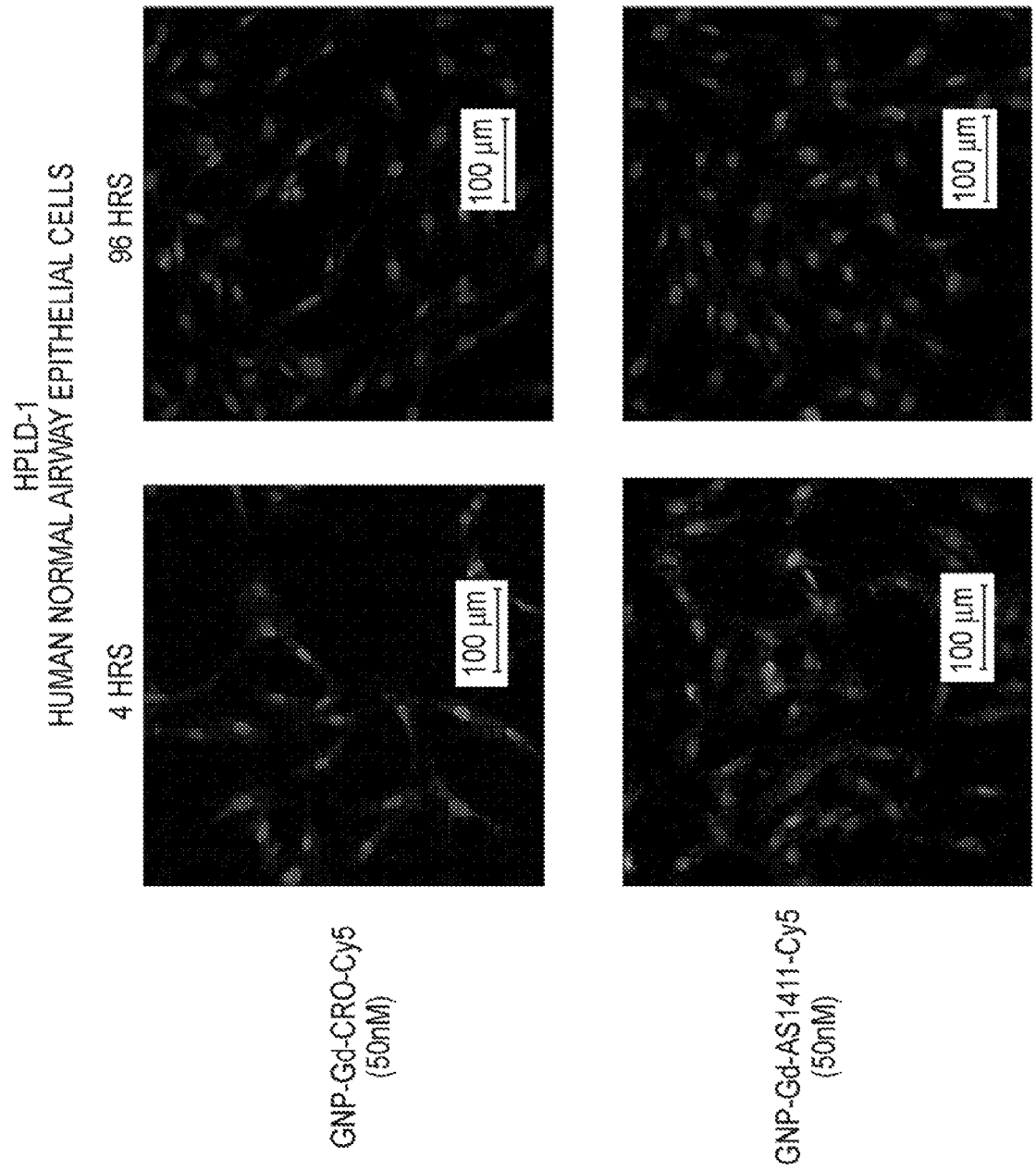
FIG. 16A illustrates uptake of fluorescent-labeled gold nanoparticle-gadolinium-oligomer conjugates in non-malignant lung cells.
Figure 16B:
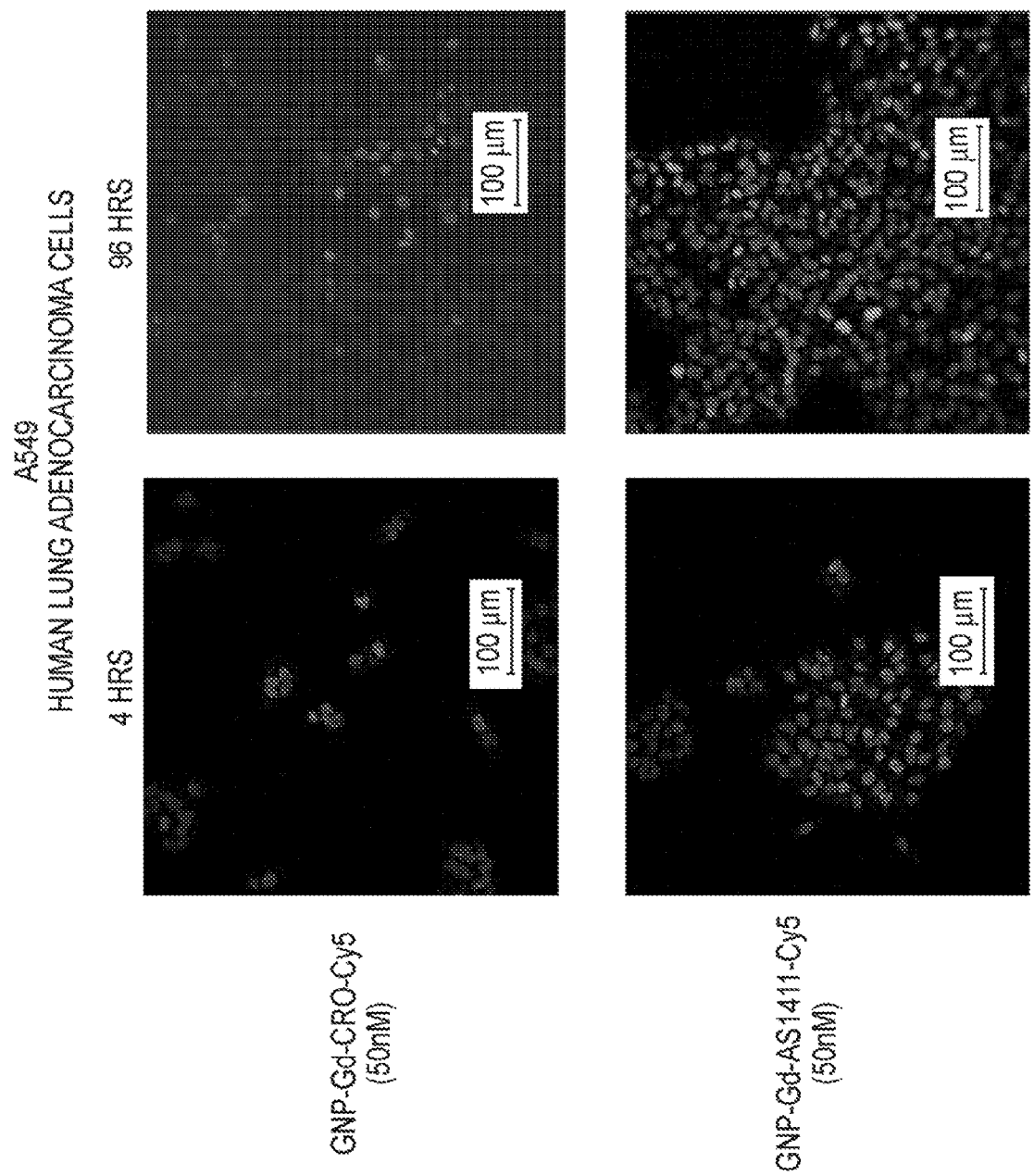
FIG. 16B illustrates uptake and selective retention of fluorescent-labeled gold nanoparticle-gadolinium-oligomer conjugates in malignant lung cancer cells.

Human normal airway epithelial cells (HPLD-1) (non-malignant) and lung adenocarcinoma cells (A549) were incubated with of fluorescent-labeled gold nanoparticle-gadolinium-oligomer conjugates for 4 and 96 hours. The cells were incubated with 50 nM GNP-Gd-CRO-Cy5 (control oligomer) or 50 nM GNP-Gd-AS1411-Cy5 using DO3A as the ligand to bind Gd and connect it to the GNP surface through a thiol linker. After incubation, the cells were harvested and washed with PBS (2×), counted using a TC-10 Cell Counter (Bio-Rad), plated in a 4 chamber slide (Bio-Tek) at 1,000 cells/well and incubated for an additional 24 hours. The cells were stained with nuclear stain DAPI after incubation and the complete DMEM media was replaced with DMEM without phenol red. Images were acquired using a NIKON® confocal microscope. FIG. 16A shows uptake in non-malignant lung cells. FIG. 16B shows uptake and selective retention of GNP-Gd-AS1411-Cy5 in malignant lung cancer cells at the 96 hours timepoint. The fluorescent-labeled GNP conjugates appear red and the nuclear stain appears blue.

The 4 hour images indicate that the uptake of aptamer conjugates in healthy and malignant cells is similar. The 96 hour images indicate that the AS1411 conjugates are only retained in malignant cells.

Gold Nanoparticle-Gadolinium-Oligomer Conjugates as MRI Contrast Agents

Gold nanoparticle-gadolinium-oligomer conjugates were studied as MRI contrast agents in vitro and in cells using a Bruker BioSpec 94/30 USR 9.4T MRI scanner. The change in reflectivity was measured using water to normalize the signals.

In a first experiment, the correlation between the concentration of the gold nanoparticle-oligomer conjugates and the improvement in the reflectivity due to the gadolinium (III) contrast agent was studied. The gold nanoparticle-oligomer conjugates included gold nanoparticles conjugated to AS1411 (5'-d(GGTGGTGGTGGTTGTGGTGGTGGTGG)-3') (GNP-AS1411), gold nanoparticles conjugated to a control oligomer (5'-d(CCTCCTCCTCCTTCTCCTCCTCCTCC)-3') (GNP-CRO) and gold nanoparticles conjugated to a control oligonucleotide (5'd(TTTT)-3) (GNP-CTR). DO3A ligand was used to bind Gd(III) and connected it to the GNP surface through a thiol linker. GNP-AS1411, GNP-CRO and GNP-CTR were used as controls to compare the relaxivity of GNP-Gd-AS1411, GNP-Gd-CRO and GNP-Gd-CTR. The relaxivity was measured at 75 nM, 300 nM and 1200 nM GNP concentrations. Table 4 shows the change in relaxivity after administration of the Gd conjugates:

TABLE 4

| | Change in relaxivity | | |
|---|---|---|---|
| | GNP-Gd-CTR | GNP-Gd-CRO | GNP-Gd-AS1411 |
| 75 nM | 17% | 15% | 19% |
| 300 nM | 33% | 25% | 44% |
| 1200 nM | 59% | 58% | 64% |

Figure 17A:
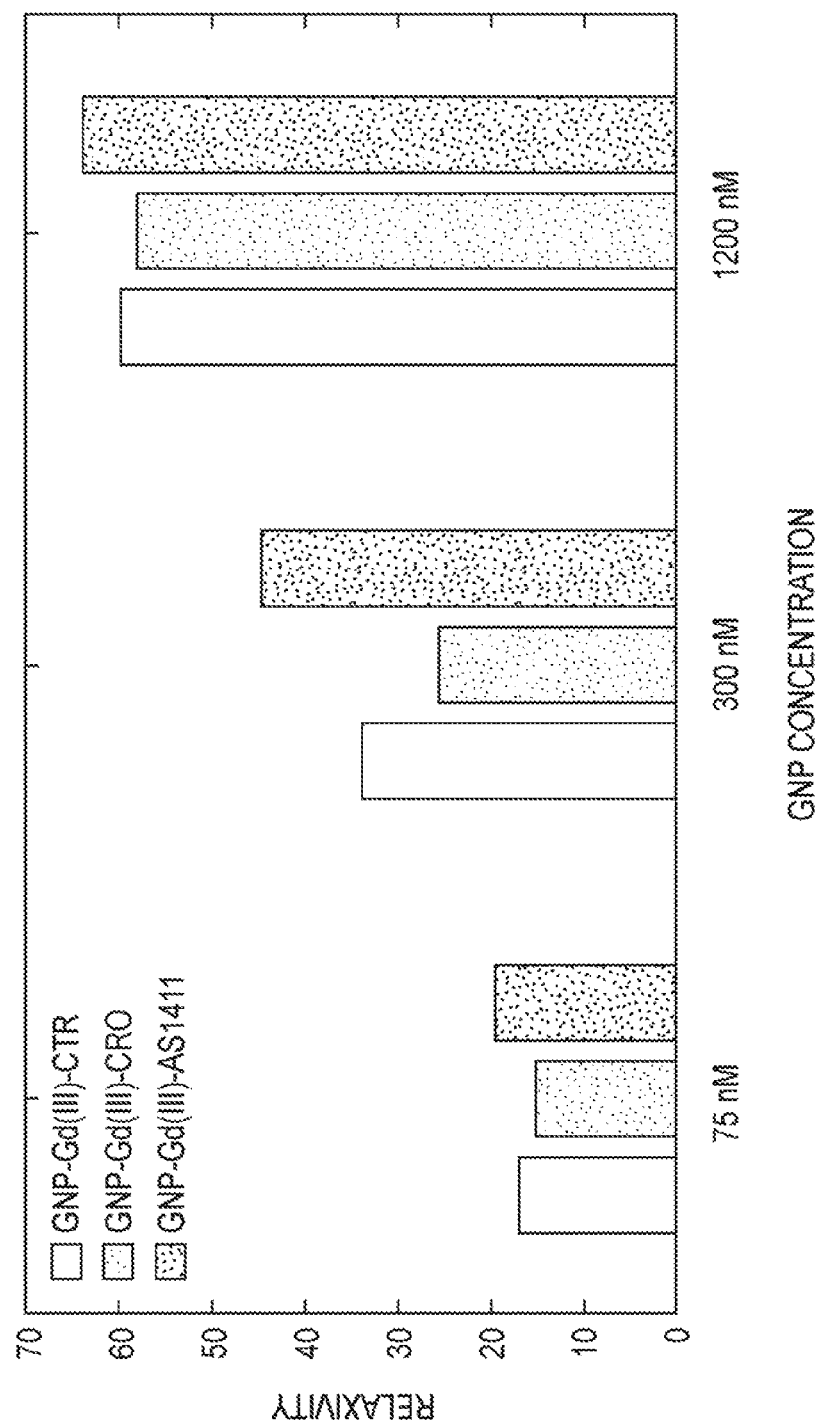
FIG. 17A illustrates the change in relaxivity of gold nanoparticle-oligomer-gadolinium conjugates in water.

These results are shown graphically in FIG. 17A. The results show no significant change in relaxivity between particles for the same concentration.

In a second experiment, the correlation between the concentration of the gold nanoparticle-oligomer conjugates in cells and the improvement in the reflectivity due to the gadolinium (III) contrast agent was studied. 30,000,000 cells were treated with GNP-AS1411, GNP-CRO, GNP-CTR, GNP-Gd-AS1411, GNP-Gd-CRO or GNP-Gd-CTR for 48 hours or 96 hours. The relaxivity was measured at 75 nM, 300 nM and 1200 nM GNP concentrations. Table 5 shows the change in relaxivity after the 48 hour treatment:

TABLE 5

Change in relaxivity after 48 hour treatment

| 48 hour treatment | GNP-Gd-CTR | GNP-Gd-CRO | GNP-Gd-AS1411 |
|---|---|---|---|
| 75 nM | 5.5% | 5% | 6% |
| 300 nM | 5.7% | 8% | 9% |
| 1200 nM | 22% | 19% | 37% |

Table 6 shows the change in relaxivity after the 96 hour treatment:

TABLE 6

Change in relaxivity after 96 hour treatment

| 96 hour treatment | GNP-Gd-CTR | GNP-Gd-CRO | GNP-Gd-AS1411 |
|---|---|---|---|
| 75 nM | 2.2% | 3.5% | 3.6% |
| 300 nM | 4.7% | 7.1% | 8.1% |
| 1200 nM | 15.3% | 17.2% | 36.8% |

Figure 17C:
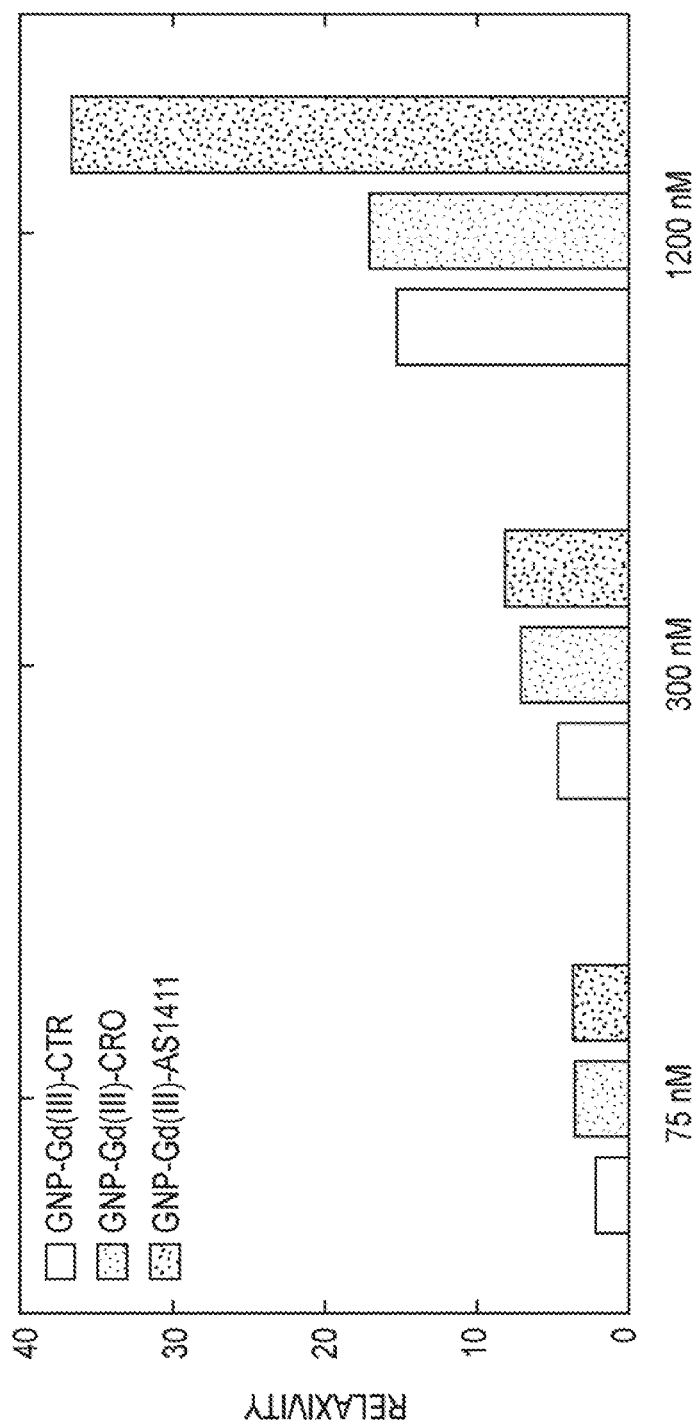
FIG. 17C illustrates the change in relaxivity of gold nanoparticle-oligomer-gadolinium conjugates in cells after 96 hours of treatment.

The 48 hour treatment results are shown graphically in FIG. 17B, and the 96 hour treatment results are shown graphically in FIG. 17C. GNP-AS1411-Gd demonstrated a significant increase in relaxivity at 1200 nM after 48 hours and 96 hours of treatment.

Figure 18:
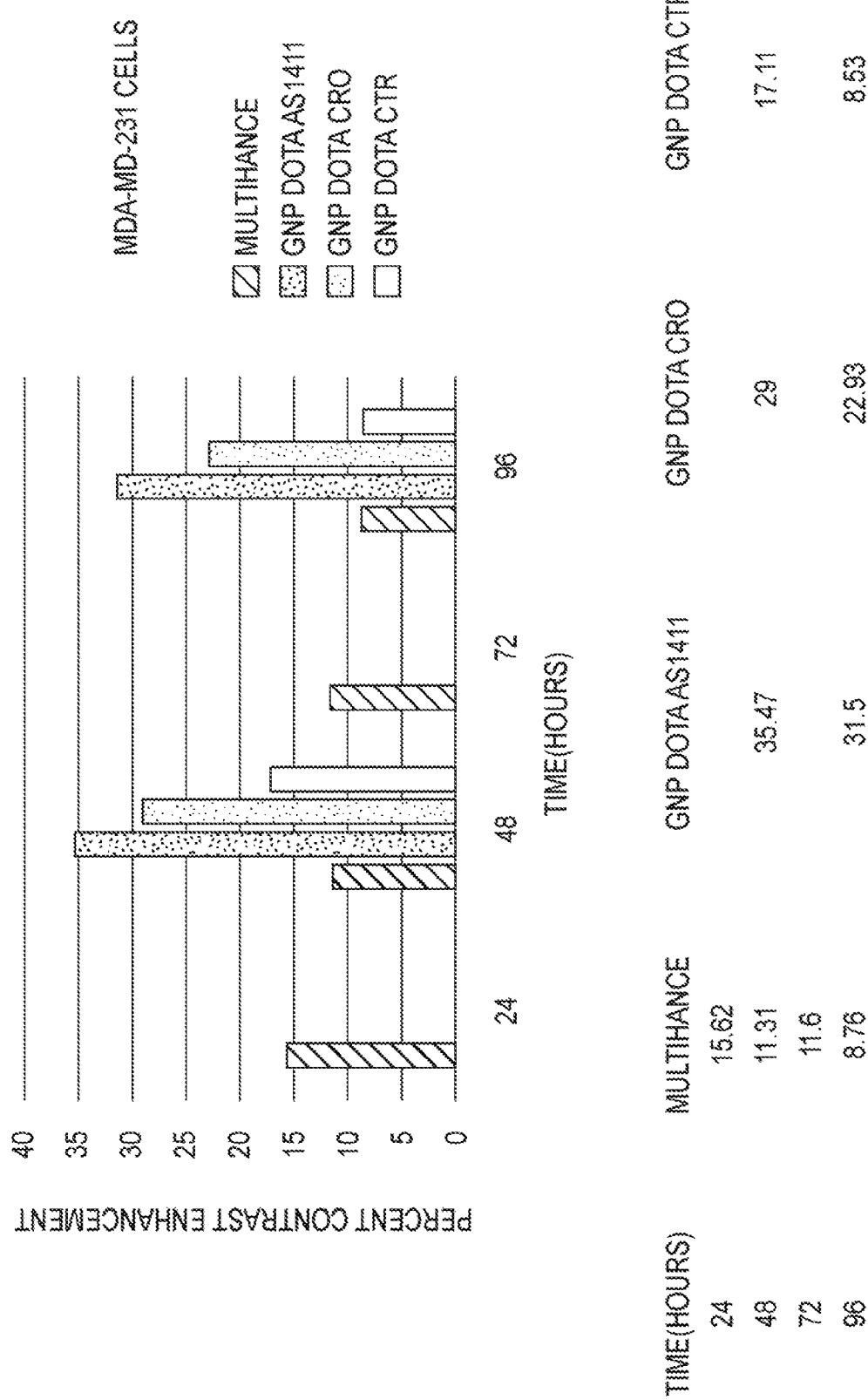
FIG. 18 illustrates the percent contrast enhancement for gold nanoparticle-oligomer conjugates and a commercially-available MRI contrast agent.

Comparison of Gold Nanoparticle-Oligomer Conjugates to Commercially-Available MRI Contrast Agent The MRI contrast enhancement properties of gold nanoparticle-oligomer conjugates were compared to MULTIHANCE® (Bracco), a commercially-available MRI contrast agent. The percent contrast enhancement was measured in breast cancer cells (MDA-MB-231). The gold nanoparticle-oligomer conjugates included gold nanoparticles conjugated to AS1411 (5'-d(GGTGGTGGTGGTTGTGGTGGTGGTGG)-3') (GNP DOTA AS1411), gold nanoparticles conjugated to a control oligomer (5'-d(CCTCCTCCTCCTTCTCCTCCTCCTCC)-3') (GNP DOTA CRO) and gold nanoparticles conjugated to a control oligonucleotide (5'd (TTTT)-3') (GNP DOTA CTR). DOTA (1,4,7,10-tetrakis (carboxymethyl)-1,4,7,10-tetraazacyclododecane) was used as the ligand. The MULTIHANCE® cells were treated for 24 hours, 48 hours, 72 hours and 96 hours, while the gold nanoparticle-oligomer conjugate cells were treated for 48 hours and 96 hours. The results are shown in FIG. 18. GNP DOTA AS1411 demonstrated a contrast enhancement approximately three times greater than MULTIHANCE®.

REFERENCES

[1] Stedman, T. L. 2000. Stedman's medical dictionary. Lippincott Williams & Wilkins, Philadelphia. xxxvi, [127], 2098.
[2] Miller, D., P. Bates, and J. Trent. 2000. Antiproliferative activity of G-rich oligonucleotides and method of using same to bind to nucleolin, Intl Pub. No. WO 00/61597.
[3] Bates P J, Miller D M, Trent J O, Xu X, "A New Method for the Diagnosis and Prognosis of Malignant Diseases" International Application, Intl Pub. No. WO 03/086174 A2 (23 Oct. 2003).
[4] Bates P J, Miller D M, Trent J O, Xu X, "Method for the Diagnosis and Prognosis of Malignant Diseases" U.S. Patent App. Pub., Pub. No. US 2005/0053607 A1 (10 Mar. 2005).
[5] Derenzini M, Sirri V, Trere D, Ochs R L, "The Quantity of Nucleolar Proteins Nucleolin and Protein B23 is Related to Cell Doubling Time in Human Cancer Cells" Lab. Invest. 73:497-502 (1995).
[6] Bates P J, Kahlon J B, Thomas S D, Trent J O, Miller D M, "Antiproliferative Activity of G-rich Oligonucleotides Correlates with Protein Binding" J. Biol. Chem. 274: 26369-77 (1999).
[7] Miller D M, Bates P J, Trent J O, Xu X, "Method for the Diagnosis and Prognosis of Malignant Diseases" U.S. Patent App. Pub., Pub. No. US 2003/0194754 A1 (16 Oct. 2003).
[8] Bandman O, Yue H, Corley N C, Shah P, "Human Nucleolin-like Protein" U.S. Pat. No. 5,932,475 (3 Aug. 1999).
[9] Reyes-Reyes E M, Teng Y, Bates P J, "A New Paradigm for Aptamer Therapeutic AS1411 Action: Uptake by Macropinocytosis and Its Stimulation by a Nucleolin-Dependent Mechanism" Cancer Res 70(21): 8617-29 (2010).
[10] Huang Y, Shi H, Zhou H, Song X, Yuan S, Luo Y, "The Angiogenic Function of Nucleolin is Mediated by Vascular Endothelial Growth Factor and Nonmuscle Myosin" Blood 107(9): 3564-71 (2006).
[11] Jain, K. K., *Advances in the field of nanooncology.* BMC medicine, 2010. 8: p. 83.
[12] Portney, N. G. and M. Ozkan, *Nano-oncology: drug delivery, imaging, and sensing.* Analytical and bioanalytical chemistry, 2006. 384(3): p. 620-30.
[13] Bates, P. J., E. W. Choi, and L. V. Nayak, *G-rich oligonucleotides for cancer treatment.* Methods in molecular biology, 2009. 542: p. 379-92.
[14] Bates, P. J., et al., *Discovery and development of the G-rich oligonucleotide AS1411 as a novel treatment for cancer.* Experimental and molecular pathology, 2009. 86(3): p. 151-64.
[15] Soundararajan, S., et al., *The nucleolin targeting aptamer AS1411 destabilizes Bcl-2 messenger RNA in human breast cancer cells.* Cancer research, 2008. 68(7): p. 2358-65.
[16] Javier, D. J., et al., *Aptamer-targeted gold nanoparticles as molecular-specific contrast agents for reflectance imaging.* Bioconjugate chemistry, 2008. 19(6): p. 1309-12.
[17] Euhus, D. M., et al., *Tumor measurement in the nude mouse.* Journal of surgical oncology, 1986. 31(4): p. 229-34.
[18] Tomayko, M. M. and C. P. Reynolds, *Determination of subcutaneous tumor size in athymic (nude) mice.* Cancer chemotherapy and pharmacology, 1989. 24(3): p. 148-54.
[19] Girvan, A. C., et al., *AGRO100 inhibits activation of nuclear factor-kappaB (NF-kappaB) by forming a complex with NF-kappaB essential modulator (NEMO) and nucleolin.* Molecular cancer therapeutics, 2006. 5(7): p. 1790-9.
[20] Mosmann, T., *Rapid colorimetric assay for cellular growth and survival: application to proliferation and cytotoxicity assays.* Journal of immunological methods, 1983. 65(1-2): p. 55-63.
[21] Vermes, I., et al., A novel assay for apoptosis. *Flow cytometric detection of phosphatidylserine expression on early apoptotic cells using fluorescein labelled Annexin V.* Journal of immunological methods, 1995. 184(1): p. 39-51.
[22] Sprague, J. E., et al., *Noninvasive imaging of osteoclasts in parathyroid hormone-induced osteolysis using a 64Cu labeled RGD peptide.* Journal of nuclear medicine: official publication, Society of Nuclear Medicine, 2007. 48(2): p. 311-8.
[23] Morgan D. M., *Methods Mol. Biol.* 1998. 79:179-183.

[24] Zhang, Y. et al., *A surface-charge study on cellular-uptake behavior of F3-peptide-conjugated iron oxide nanoparticles*. Small, 2009 5(17): p. 1990-6.

[25] Orringer, D. A., et al. *In vitro characterization of a targeted, dye-loaded nanodevice for intraoperative tumor delineation*. Neurosurgery, 2009 64(5): p. 965-72.

[26] Cooper et al. [2014], *Front. Chem.* 14, 2, 86.

[27] Alkilany, A. M. and C. J. Murphy, *Toxicity and cellular uptake of gold nanoparticles: what we have learned so far?* Journal of Nanoparticle Research, 2010. 12(7): p. 2313-2333.

[28] National Lung Screening Trial Research, T., et al., *Reduced lung-cancer mortality with low-dose computed tomographic screening*. N Engl J Med, 2011. 365(5): p. 395-409.

What is claimed is:

1. A method of treating cancer, comprising administering an effective amount of a pharmaceutical composition comprising an anti-nucleolin agent conjugated to nanoparticles, to a patient in need thereof, followed by radiation therapy, wherein the anti-nucleolin agent is AS1411, the nanoparticles comprise gold, and the radiation therapy is selected from the group consisting of X-rays, Brachy therapy, proton radiation, neutron radiation and gamma rays.

2. The method of treating cancer of claim 1, wherein the cancer is selected from the group consisting of melanoma, lymphoma, plasmocytoma, sarcoma, glioma, thymoma, leukemia, breast cancer, prostate cancer, colon cancer, liver cancer, esophageal cancer, brain cancer, lung cancer, ovary cancer, cervical cancer and hepatoma.

3. The method of treating cancer of claim 1, wherein the cancer is selected from the group consisting of breast cancer, prostate cancer, colon cancer and lung cancer.

4. The method of treating cancer of claim 1, further comprising administering a second cancer treatment selected from the group consisting of vinorelbine, mitomycin, camptothecin, cyclophosphamide, methotrexate, tamoxifen citrate, 5-fluorouracil, irinotecan, doxorubicin, flutamide, paclitaxel, docetaxel, vinblastine, imatinib mesylate, anthracycline, letrozole, arsenic trioxide, anastrozole, triptorelin pamoate, ozogamicin, irinotecan hydrochloride, BCG live, leuprolide acetate implant (VIADUR®), bexarotene, exemestane, topotecan hydrochloride, gemcitabine HCL, daunorubicin hydrochloride, toremifene citrate (FARESTON®), carboplatin, cisplatin, oxaliplatin, trastuzumab, lapatinib, gefitinib, cetuximab, panitumumab, temsirolimus, everolimus, vandetanib, vemurafenib, crizotinib, vorinostat, bevacizumab, hyperthermia, gene therapy and photodynamic therapy.

5. The method of treating cancer of claim 1, wherein the nanoparticles have an average diameter of 1 to 50 nm.

6. The method of treating cancer of claim 1, wherein the nanoparticles have an average diameter of 1 to 20 nm.

7. The method of treating cancer of claim 4, wherein the second cancer treatment comprises 5-fluorouricil.

8. A method of treating breast cancer, comprising administering an effective amount of a pharmaceutical composition comprising an anti-nucleolin agent conjugated to nanoparticles, to a patient in need thereof, followed by radiation therapy, wherein the anti-nucleolin agent is AS1411, the nanoparticles comprise gold, and the radiation therapy is selected from the group consisting of X-rays, Brachy therapy, proton radiation, neutron radiation and gamma rays.

9. The method of claim 8, wherein the breast cancer is triple negative breast cancer.

10. A method of treating lung cancer, comprising administering an effective amount of a pharmaceutical composition comprising an anti-nucleolin agent conjugated to nanoparticles, to a patient in need thereof, followed by radiation therapy, wherein the anti-nucleolin agent is AS1411, the nanoparticles comprise gold, and the radiation therapy is selected from the group consisting of X-rays, Brachy therapy, proton radiation, neutron radiation and gamma rays.

11. The method of claim 10, wherein the lung cancer is non-small cell lung cancer.

12. The method of treating breast cancer of claim 8, further comprising administering a second cancer treatment selected from the group consisting of vinorelbine, mitomycin, camptothecin, cyclophosphamide, methotrexate, tamoxifen citrate, 5-fluorouracil, irinotecan, doxorubicin, flutamide, paclitaxel, docetaxel, vinblastine, imatinib mesylate, anthracycline, letrozole, arsenic trioxide, anastrozole, triptorelin pamoate, ozogamicin, irinotecan hydrochloride, BCG live, leuprolide acetate implant (VIADUR®), bexarotene, exemestane, topotecan hydrochloride, gemcitabine HCL, daunorubicin hydrochloride, toremifene citrate (FARESTON®), carboplatin, cisplatin, oxaliplatin, trastuzumab, lapatinib, gefitinib, cetuximab, panitumumab, temsirolimus, everolimus, vandetanib, vemurafenib, crizotinib, vorinostat, bevacizumab, hyperthermia, gene therapy and photodynamic therapy.

13. The method of treating breast cancer of claim 8, wherein the nanoparticles have an average diameter of 1 to 50 nm.

14. The method of treating breast cancer of claim 8, wherein the nanoparticles have an average diameter of 1 to 20 nm.

15. The method of treating breast cancer of claim 8, wherein the radiation therapy comprises X-rays.

16. The method of treating lung cancer of claim 10, further comprising administering a second cancer treatment selected from the group consisting of vinorelbine, mitomycin, camptothecin, cyclophosphamide, methotrexate, tamoxifen citrate, 5-fluorouracil, irinotecan, doxorubicin, flutamide, paclitaxel, docetaxel, vinblastine, imatinib mesylate, anthracycline, letrozole, arsenic trioxide, anastrozole, triptorelin pamoate, ozogamicin, irinotecan hydrochloride, BCG live, leuprolide acetate implant (VIADUR®), bexarotene, exemestane, topotecan hydrochloride, gemcitabine HCL, daunorubicin hydrochloride, toremifene citrate (FARESTON®), carboplatin, cisplatin, oxaliplatin, trastuzumab, lapatinib, gefitinib, cetuximab, panitumumab, temsirolimus, everolimus, vandetanib, vemurafenib, crizotinib, vorinostat, bevacizumab, hyperthermia, gene therapy and photodynamic therapy.

17. The method of treating lung cancer of claim 10, wherein the nanoparticles have an average diameter of 1 to 50 nm.

18. The method of treating lung cancer of claim 10, wherein the nanoparticles have an average diameter of 1 to 20 nm.

19. The method of treating lung cancer of claim 10, wherein the radiation therapy comprises X-rays.

20. The method of treating cancer of claim 1, wherein the radiation therapy comprises X-rays.

* * * * *